(12) United States Patent
Moradei et al.

(10) Patent No.: US 9,187,415 B2
(45) Date of Patent: Nov. 17, 2015

(54) SULFONAMIDES AS HIV PROTEASE INHIBITORS

(75) Inventors: Oscar M. Moradei, Burlington, MA (US); Sheldon Crane, Ile-Perrot (CA); Daniel J. McKay, Ottawa (CA); Marie-Eve Lebrun, Dollard-des-Ormeaux (CA); Vouy Linh Truong, Pierrefonds (CA)

(73) Assignee: Merck Canada Inc., Kirkland, Province of Quebec (CA)

( * ) Notice: Subject to any disclaimer, the term of this patent is extended or adjusted under 35 U.S.C. 154(b) by 293 days.

(21) Appl. No.: 13/882,329

(22) PCT Filed: Oct. 27, 2011

(86) PCT No.: PCT/CA2011/001206
§ 371 (c)(1),
(2), (4) Date: Oct. 1, 2013

(87) PCT Pub. No.: WO2012/055034
PCT Pub. Date: May 3, 2012

(65) Prior Publication Data
US 2014/0018326 A1    Jan. 16, 2014

Related U.S. Application Data

(60) Provisional application No. 61/408,006, filed on Oct. 29, 2010.

(51) Int. Cl.
| | | |
|---|---|---|
| C07C 311/41 | (2006.01) | |
| C07C 311/42 | (2006.01) | |
| C07D 231/12 | (2006.01) | |
| C07D 261/08 | (2006.01) | |
| C07D 277/64 | (2006.01) | |
| C07D 239/26 | (2006.01) | |
| C07D 417/12 | (2006.01) | |
| C07D 417/14 | (2006.01) | |
| A61K 31/428 | (2006.01) | |
| A61K 31/42 | (2006.01) | |
| A61K 31/415 | (2006.01) | |
| A61K 31/4439 | (2006.01) | |
| A61K 31/4412 | (2006.01) | |
| A61K 31/506 | (2006.01) | |
| A61K 31/18 | (2006.01) | |
| C07C 311/18 | (2006.01) | |
| C07C 311/29 | (2006.01) | |
| C07C 317/40 | (2006.01) | |
| C07C 323/49 | (2006.01) | |
| C07D 213/75 | (2006.01) | |
| A61K 31/63 | (2006.01) | |
| A61K 31/635 | (2006.01) | |
| A61K 45/06 | (2006.01) | |
| C07D 277/62 | (2006.01) | |

(52) U.S. Cl.
CPC ............ *C07C 311/18* (2013.01); *A61K 31/428* (2013.01); *A61K 31/4439* (2013.01); *A61K 31/506* (2013.01); *A61K 31/63* (2013.01); *A61K 31/635* (2013.01); *A61K 45/06* (2013.01); *C07C 311/29* (2013.01); *C07C 311/41* (2013.01); *C07C 317/40* (2013.01); *C07C 323/49* (2013.01); *C07D 213/75* (2013.01); *C07D 231/12* (2013.01); *C07D 239/26* (2013.01); *C07D 261/08* (2013.01); *C07D 277/62* (2013.01); *C07D 277/64* (2013.01); *C07D 417/12* (2013.01); *C07D 417/14* (2013.01); *C07C 2101/02* (2013.01)

(58) Field of Classification Search
None
See application file for complete search history.

(56) References Cited

U.S. PATENT DOCUMENTS

| 7,388,008 | B2 | 6/2008 | Stranix et al. |
| 8,497,383 | B2 | 7/2013 | Coburn et al. |

FOREIGN PATENT DOCUMENTS

| WO | 0168593 | A2 | 9/2001 |
| WO | 02064551 | A1 | 8/2002 |
| WO | 03074467 | A2 | 9/2003 |
| WO | 2004056764 | A1 | 7/2004 |
| WO | 2006012725 | A1 | 2/2006 |
| WO | 2006114001 | A1 | 11/2006 |
| WO | 2008023273 | A2 | 2/2008 |
| WO | 2008078200 | A2 | 7/2008 |
| WO | 2009042093 | A1 | 4/2009 |
| WO | 2009042094 | A2 | 4/2009 |
| WO | 2009148600 | A2 | 12/2009 |
| WO | 2012055031 | A1 | 5/2012 |
| WO | 2013059928 | A1 | 5/2013 |

*Primary Examiner* — Michael Barker
(74) *Attorney, Agent, or Firm* — Carol S. Quagliato; Laura M. Ginkel

(57) ABSTRACT

Compounds of Formula I are disclosed: wherein L, A, $R^1$, $R^2$, $R^{3A}$, $R^{3B}$, $R^{4A}$, $R^{4B}$, $R^5$, $R^6$ and $R^7$ are defined herein. The compounds encompassed by Formula I include compounds which are HIV protease inhibitors and other compounds which can be metabolized in vivo to HIV protease inhibitors. The compounds and their pharmaceutically acceptable salts are useful for the prophylaxis or treatment of infection by HIV and the prophylaxis, treatment, or delay in the onset of AIDS. The compounds and their salts can be employed as ingredients in pharmaceutical compositions, optionally in combination with other antivirals, immunomodulators, antibiotics or vaccines.

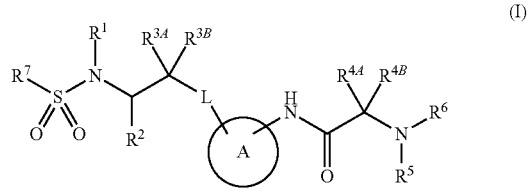

(I)

20 Claims, No Drawings

SULFONAMIDES AS HIV PROTEASE INHIBITORS

CROSS-REFERENCE TO RELATED APPLICATION

This application claims the benefit of U.S. provisional application No. 61/408,006 filed on Oct. 29, 2010.

FIELD OF THE INVENTION

The present invention is directed to certain compounds and their pharmaceutically acceptable salts. Some of these derivatives are compounds which are HIV protease inhibitors. The compounds are useful for the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., Proc. Nat'l Acad. Sci. 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame Ratner et al., Nature 1985, 313: 277. Amino acid sequence homology provides evidence that the pol sequence encodes reverse transcriptase, an endonuclease, HIV protease and gag, which encodes the core proteins of the virion (Toh et al., EMBO J. 1985, 4: 1267; Power et al., Science 1986, 231: 1567; Pearl et al., Nature 1987, 329: 351. Wensing A. M., van Maarseveen N. M., Nijhuis M. "Fifteen years of HIV Protease Inhibitors: raising the bather to resistance". Antiviral Res. 2010, 85, 59-74.

Ramos J. "Boosted protease inhibitors as a therapeutic option in the treatment of HIV-infected children". HIV Med. 2009, 10(9):536-47.

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitor also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., New England J. Med. 1997, 337: 725-733 and Gulick et al., New England J. Med. 1997, 337: 734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

References disclosing amino acid derivatives with HIV aspartyl protease inhibiting properties, processes for preparing the derivatives, and/or therapeutic uses of the derivatives include: WO 01/68593, WO 02/064551 A1, WO 03/074467 A2, WO 2004/056764 A1, WO 2006/012725 A1, WO 2006/114001 A1, WO 2007/062526 A1, WO 2008/023273 A2, WO 2008/078200 A2, and U.S. Pat. No. 7,388,008 B2.

SUMMARY OF THE INVENTION

The present invention is directed to certain compounds and their use in the inhibition of HIV protease, the prophylaxis of infection by HIV, the treatment of infection by HIV, and the prophylaxis, treatment, and delay in the onset or progression of AIDS. More particularly, the present invention includes compounds of Formula I:

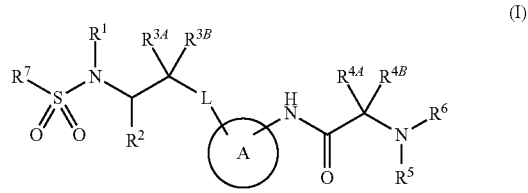

(I)

and pharmaceutically salts thereof, wherein:
$R^1$ is selected from the group consisting of $C_{1-6}$ alkyl, $C_{1-6}$ fluoroalkyl, CycA, $C_{1-6}$ alkyl substituted with CyCA, HetA and $C_{1-6}$ alkyl substituted with HetA;
$R^2$ is selected from the group consisting of C(O)OH, C(O)NH$_2$ or CH($R^J$)—Z, wherein:
Z is OH or OR$^P$;
$R^J$ is selected from the group consisting of H, $C_1$ alkyl and $C_1$ fluoroalkyl
$R^P$ is selected from the group consisting of PO(OH)O$^-$.M$^+$; PO(O$^-$)$_2$.2M$^+$; PO(O$^-$)$_2$.M$^{2+}$ and C(O)R$^Q$;
M$^+$ is a pharmaceutically acceptable monovalent counterion;
M$^{2+}$ is a pharmaceutically acceptable divalent counterion; and
$R^Q$ is selected from the group consisting of:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl, (5) O—C$_{1-6}$ alkyl substituted with O—C$_{1-6}$ alkyl,
(6) O—C$_{1-6}$ fluoroalkyl,
(7) C(O)—C$_{1-6}$ alkylene-N(H)—C$_{1-6}$ alkyl,
(8) C(O)—C$_{1-6}$ alkylene-N(—C$_{1-6}$ alkyl)$_2$,
(9) C$_{1-6}$ alkyl substituted with C(O)O—C$_{1-6}$ alkyl,
(10) C$_{1-6}$ alkyl substituted with C(O)OH,
(11) C$_{1-6}$ alkyl substituted with C(O)—C$_{1-6}$ alkyl,
(12) N(H)—C$_{1-6}$ alkyl,
(13) N(—C$_{1-6}$ alkyl)$_2$,
(14) C$_{1-6}$ alkyl substituted with NH$_2$, N(H)—C$_{1-6}$ alkyl, or N(—C$_{1-6}$ alkyl)$_2$,
(15) AryA,
(16) C$_{1-6}$ alkyl substituted with AryA,
(17) O—C$_{1-6}$ alkyl substituted with AryA,
(18) HetA,
(19) C$_{1-6}$ alkyl substituted with HetA,
(20) O—C$_{1-6}$ alkyl substituted with HetA,
(21) HetB and
(22) O-HetB;

R$^{3A}$ and R$^{3B}$ are each independently selected from the group consisting of H, F or C$_{1-6}$ alkyl;

L is selected from the group consisting of CH(R$^E$), N(R$^E$), O, S, S(O), S(O)$_2$ and a single bond;

R$^E$ is selected from the group consisting of H, F and C$_{1-6}$ alkyl;

Ring A is:
(i) a carbocyclic aromatic ring selected from the group consisting of benzene and naphthalene, wherein, in addition to the two moieties attached to the ring as shown in Formula I, the ring is unsubstituted, or substituted with from 1 to 3 substituents X$^E$, wherein each X$^E$ independently has the same definition as X$^A$; or
(ii) a 6-membered heteroaromatic ring containing a total of from 1 to 3 heteroatoms selected from 1 to 3 N, zero or 1 O, and zero or 1 S, wherein, in addition to the two moieties attached to the ring as shown in Formula 1, the ring is unsubstituted, or substituted with from 1 to 3 substituents X$^E$;

R$^{4A}$ is selected from the group consisting of:

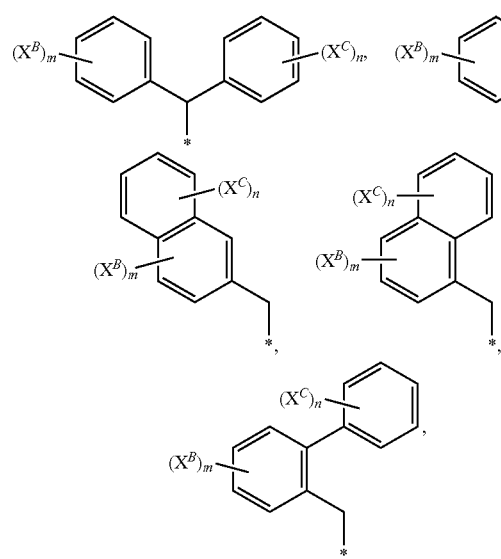

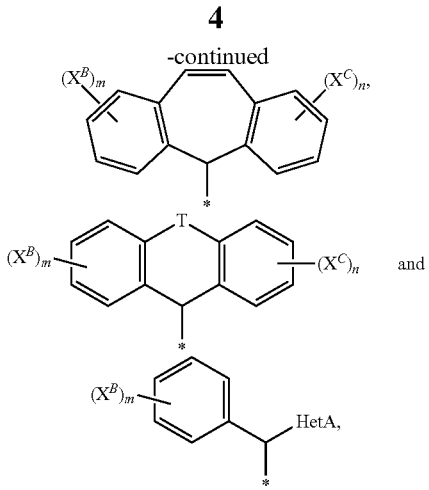

wherein the asterisk (*) denotes the point of attachment to the rest of the compound;

R$^{4B}$ is H or C$_{1-6}$ alkyl;

alternatively, R$^{4A}$ and R$^{4B}$ together with the carbon to which they are attached form a C$_{3-6}$ cycloalkyl which is unsubstituted, or substituted with phenyl, wherein the phenyl is unsubstituted, or substituted with from 1 to 3 X$^B$;

each X$^B$ and each X$^C$ are independently selected from the group consisting of:
(1) C$_{1-6}$ alkyl,
(2) C$_{3-6}$ cycloalkyl,
(3) C$_{1-6}$ haloalkyl,
(4) OH,
(5) O—C$_{1-6}$ alkyl,
(6) O—C$_{1-6}$ haloalkyl,
(7) O—C$_{3-6}$ cycloalkyl,
(8) SH,
(9) S—C$_{1-6}$ alkyl,
(10) S—C$_{1-6}$ haloalkyl,
(11) S—C$_{3-6}$ cycloalkyl,
(12) halo,
(13) CN,
(14) NO$_2$,
(15) NH$_2$,
(16) N(H)—C$_{1-6}$ alkyl,
(17) N(—C$_{1-6}$ alkyl)$_2$,
(18) N(H)C(O)—C$_{1-6}$ alkyl,
(19) N(H)CH(O),
(20) CH(O),
(21) C(O)—C$_{1-6}$ alkyl,
(22) C(O)OH,
(23) C(O)O—C$_{1-6}$ alkyl,
(24) SO$_2$H,
(25) SO$_2$—C$_{1-6}$ alkyl; and
(26) C$_{1-6}$ alkyl substituted with a moiety selected from the group consisting of:
(a) C$_{1-6}$ haloalkyl,
(b) OH
(c) O—C$_{1-6}$ alkyl,
(d) O—C$_{1-6}$ haloalkyl,
(e) O—C$_{3-6}$ cycloalkyl,
(f) SH,
(g) S—C$_{1-6}$ alkyl,
(h) halo,
(i) CN,
(j) NO$_2$,
(k) NH$_2$,
(l) N(H)—C$_{1-6}$ alkyl, (m) N(—C$_{1-6}$ alkyl)$_2$,
(n) C(O)—C$_{1-6}$ alkyl,
(o) C(O)OH,
(p) C(O)O—C$_{1-6}$ alkyl and
(q) SO$_2$—C$_{1-6}$ alkyl;

T is selected from the group consisting of O, S, S(O) and SO$_2$;

m is an integer equal to 0, 1, 2, or 3;

n is an integer equal to 0, 1, 2, or 3;

R$^5$ is selected from the group consisting of H, C$_{1-6}$ alkyl, C$_{3-6}$ cycloalkyl and C$_{1-6}$ alkyl substituted with C$_{3-6}$ cycloalkyl, or C(O)—R$^K$;

R$^6$ is H or C$_{1-6}$ alkyl;

R$^K$ is selected from the group consisting of:
(1) C$_{1-6}$ alkyl,
(2) C$_{3-6}$ cycloalkyl,
(3) C$_{1-6}$ alkyl substituted with C$_{3-6}$ cycloalkyl,
(4) O—C$_{1-6}$ alkyl,
(5) O—C$_{1-6}$ alkyl substituted with O—C$_{1-6}$ alkyl,
(6) O—C$_{1-6}$ fluoroalkyl,
(8) C$_{1-6}$ alkyl substituted with C(O)O—C$_{1-6}$ alkyl,
(9) C$_{1-6}$ alkyl substituted with C(O)OH,
(10) C$_{1-6}$ alkyl substituted with C(O)—C$_{1-6}$ alkyl,
(11) N(H)—C$_{1-6}$ alkyl,
(12) N(—C$_{1-6}$ alkyl)$_2$,
(13) C$_{1-6}$ alkyl substituted with NH$_2$, N(H)—C$_{1-6}$ alkyl, or N(—C$_{1-6}$ alkyl)$_2$,
(14) AryA,
(15) C$_{1-6}$ alkyl substituted with AryA,
(16) O—C$_{1-6}$ alkyl substituted with AryA,
(17) HetA,
(18) C$_{1-6}$ alkyl substituted with HetA,
(19) O—C$_{1-6}$ alkyl substituted with HetA,
(20) HetB,
(21) O-HetB and
(22) O—C$_{1-6}$ alkyl substituted with HetB;

R$^7$ is AryQ or HetQ;

AryQ is an aryl which is independently phenyl or naphthyl, wherein the phenyl or naphthyl is unsubstituted, or substituted with from 1 to 4 X$^A$ each of which is independently selected from the group consisting of:
(1) C$_{1-6}$ alkyl,
(2) C$_{3-6}$ cycloalkyl,
(3) C$_{1-6}$ haloalkyl,
(4) OH
(5) O—C$_{1-6}$ alkyl,
(6) O—C$_{1-6}$ haloalkyl,
(7) O—C$_{3-6}$ cycloalkyl,
(8) SH,
(9) S—C$_{1-6}$ alkyl,
(10) S—C$_{1-6}$ haloalkyl,
(11) S—C$_{3-6}$ cycloalkyl,
(12) halo,
(13) CN,
(14) NO$_2$,
(15) NH$_2$,
(16) N(H)—C$_{1-6}$ alkyl,
(17) N(—C$_{1-6}$ alkyl)$_2$,
(18) N(H)C(O)—C$_{1-6}$ alkyl,
(19) N(H)CH(O),
(20) CH(O),
(21) C(O)—C$_{1-6}$ alkyl,
(22) C(O)OH,
(23) C(O)O—C$_{1-6}$ alkyl,
(24) SO$_2$H,
(25) SO$_2$—C$_{1-6}$ alkyl and
(26) C$_{1-6}$ alkyl substituted with a moiety selected from the group consisting of:
(a) C$_{3-6}$ cycloalkyl,
(b) C$_{1-6}$ haloalkyl,
(c) OH
(d) O—C$_{1-6}$ alkyl,
(e) O—C$_{1-6}$ haloalkyl,
(f) O—C$_{3-6}$ cycloalkyl,
(g) SH,
(h) S—C$_{1-6}$ alkyl,
(i) S—C$_{1-6}$ haloalkyl,
(j) S—C$_{3-6}$ cycloalkyl,
(k) halo,
(l) CN,
(m) NO$_2$,
(n) NH$_2$,
(o) N(H)—C$_{1-6}$ alkyl,
(p) N(—C$_{1-6}$ alkyl)$_2$,
(q) N(H)C(O)—C$_{1-6}$ alkyl,
(r) N(H)CH(O),
(s) CH(O),
(t) C(O)—C$_{1-6}$ alkyl,
(u) C(O)OH,
(v) C(O)O—C$_{1-6}$ alkyl,
(w) SO$_2$H and
(x) SO$_2$—C$_{1-6}$ alkyl;

HetQ is a heteroaryl which is independently (i) a 5- or 6-membered heteroaromatic ring containing from 1 to 4 heteroatoms independently selected from N, O and S, wherein each N is optionally in the form of an oxide or (ii) a 9- or 10-membered bicyclic, fused ring system containing from 1 to 4 heteroatoms independently selected from N, O and S, and wherein at least one of the rings is aromatic, each N in a ring is optionally in the form of an oxide, and each S is optionally S(O) or S(O)$_2$; and wherein the heteroaryl is unsubstituted, or substituted with from 1 to 4 X$^A$ substituents each of which is independently as set forth in the definition of AryQ.

CycA is a C$_{3-7}$ cycloalkyl which is unsubstituted, or substituted with from 1 to 4 substituents each of which is independently halo or C$_{1-6}$ alkyl;

each AryA is an aryl which is independently phenyl or naphthyl, wherein the phenyl or naphthyl is unsubstituted, or substituted with from 1 to 4 Y$^B$ wherein each Y$^B$ independently has the same definition as X$^B$;

each HetA is a heteroaryl which is independently (i) a 5- or 6-membered heteroaromatic ring containing from 1 to 4 heteroatoms independently selected from N, O and S, or (ii) is a fused, 9- or 10-membered heterobicyclic ring containing from 1 to 4 heteroatoms independently selected from N, O and S, and wherein at least one of the rings is aromatic, each N in a ring is optionally in the form of an oxide, and each S is optionally S(O) or S(O)$_2$; wherein the heteroaromatic ring (i) or the heterobicyclic ring (ii) is unsubstituted, or substituted with from 1 to 4 Y$^C$ wherein each Y$^C$ independently has the same definition as X$^B$;

each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is unsubstituted, or substituted with from 1 to 4 substituents each of which is independently selected from the group consisting of halogen, CN, C$_{1-6}$ alkyl, OH, oxo, O—C$_{1-6}$ alkyl, C$_{1-6}$ haloalkyl, O—C$_{1-6}$ haloalkyl, C(O)NH$_2$, C(O)N(H)—C$_{1-6}$ alkyl, C(O)N(—C$_{1-6}$ alkyl)$_2$, C(O)H, C(O)—C$_{1-6}$ alkyl, CO$_2$H, CO$_2$—C$_{1-6}$ alkyl, SO$_2$H and SO$_2$—C$_{1-6}$ alkyl.

In some embodiments, the invention is directed to compounds of Formula I, or pharmaceutically acceptable salts thereof, wherein $R^7$ is:

(i) AryQ, wherein AryQ is phenyl which is unsubstituted, or substituted with from 1 to 4 $X^A$; or (ii) HetQ, wherein HetQ is a 9- or 10-membered bicyclic, fused ring system which is phenyl with a 5- or 6-membered, saturated or unsaturated heterocycle fused thereto, wherein the heterocycle contains from 1 to 2 heteroatoms independently selected from N, O and S, and wherein the fused ring system is unsubstituted, or substituted with from 1 to 4 $X^A$.

In some embodiments, the invention is directed to compounds of Formula I, or pharmaceutically acceptable salts thereof, wherein $R^1$ is selected from the group consisting of $C_{1-6}$ alkyl, $C_{1-6}$ fluoroalkyl, CycA, $CH_2$-CycA and $CH_2$-HetA;

$R^2$ is selected form the group consisting of C(O)OH, C(O)NH$_2$, $CH_2$—Z, CH(CH$_3$)—Z, CH(CF$_3$)—Z; wherein Z is OH, NH$_2$, or OR$^P$; and wherein $R^P$ is P(O)(OH)$_2$, P(O)(ONa)$_2$, P(O)(OK)$_2$, C(O)—$C_{1-6}$ alkyl, C(O)O—$C_{1-6}$ alkyl, C(O)N(—$C_{1-6}$ alkyl)$_2$, C(O)-pyridyl and C(O)—$C_{1-6}$ alkylene-NH$_2$;

$R^{3A}$ is H, or $C_{1-4}$ alkyl;

$R^{3B}$ is H;

L is selected from the group consisting of CH$_2$, NH, O, S, S(O), S(O)$_2$ and a single bond;

Ring A is:

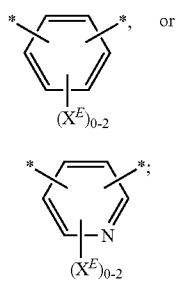

the asterisks (*) denote the points of attachment to the rest of the compound;

each $X^E$ independently has the same definition as $X^A$ below;

$R^{4A}$ is selected from the group consisting of:

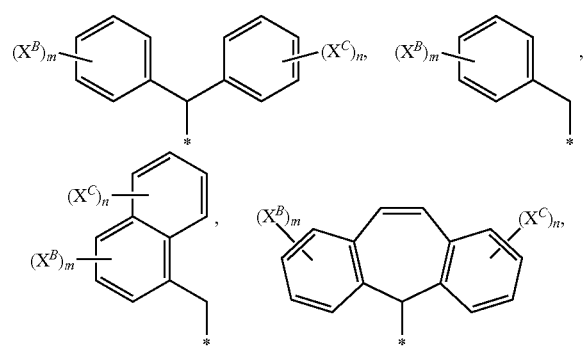

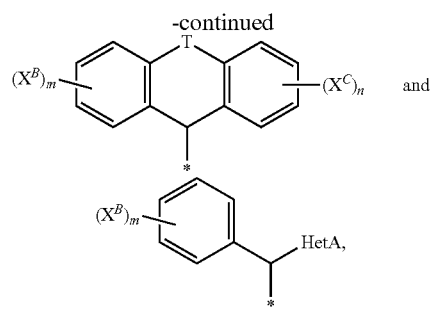

wherein the asterisk (*) denotes the point of attachment to the rest of the compound;

$R^{4B}$ is H or $C_{1-4}$ alkyl;

alternatively, $R^{4A}$ and $R^{4B}$ together with the carbon to which they are attached form a $C_{3-5}$ cycloalkyl which is unsubstituted, or substituted with phenyl, wherein the phenyl is unsubstituted, or substituted with from 1 to 2 $X^B$;

each $X^B$ and each $X^C$ are independently selected from the group consisting of:

(1) $C_{1-3}$ alkyl,
(2) cyclopropyl,
(3) CF$_3$,
(4) OH,
(5) O—$C_{1-3}$ alkyl,
(6) OCF$_3$,
(7) Cl,
(8) Br,
(9) F,
(10) CN,
(11) NO$_2$,
(12) NH$_2$,
(13) N(H)—$C_{1-3}$ alkyl,
(14) N(—$C_{1-3}$ alkyl)$_2$,
(15) C(O)—$C_{1-3}$ alkyl,
(16) CO$_2$H,
(17) C(O)O—$C_{1-3}$ alkyl,
(18) CH$_2$OH and
(19) CH$_2$O—$C_{1-3}$ alkyl;

wherein m is an integer equal to 0, 1, or 2;

wherein n is an integer equal to 0, 1, or 2;

$R^5$ is selected form the group consisting of H, $C_{1-6}$ alkyl, C(O)—$C_{1-6}$ alkyl, C(O)O—$C_{1-6}$ alkyl, C(O)N(—$C_{1-6}$ alkyl)$_2$, C(O)-HetA, C(O)OCH$_2$-HetA, C(O)-HetB and C(O)OCH$_2$-HetB;

$R^6$ is H or $C_{1-4}$ alkyl;

$R^7$ is phenyl or benzothiazolyl, either of which is unsubstituted, or substituted with 1 or 2 $X^A$, each of which is independently selected from the group consisting of:

(1) $C_{1-3}$ alkyl,
(2) cyclopropyl,
(3) CF$_3$,
(4) OH,
(5) O—$C_{1-3}$ alkyl,
(6) OCF$_3$,
(7) Cl,
(8) Br,
(9) F,
(10) CN,
(11) NO$_2$,
(12) NH$_2$,
(13) N(H)—$C_{1-3}$ alkyl,
(14) N(—$C_{1-3}$ alkyl)$_2$,
(15) C(O)—$C_{1-3}$ alkyl,
(16) CO$_2$H,

(17) C(O)O—$C_{1-3}$ alkyl and
(18) $C_{1-3}$ alkyl substituted with
  (a) cyclopropyl,
  (b) $CF_3$,
  (c) OH,
  (d) O—$C_{1-3}$ alkyl,
  (e) $OCF_3$,
  (f) Cl,
  (g) Br,
  (h) F,
  (i) CN,
  (j) $NO_2$,
  (k) $NH_2$,
  (l) N(H)—$C_{1-3}$ alkyl,
  (m) N(—$C_{1-3}$ alkyl)$_2$,
  (n) C(O)—$C_{1-3}$ alkyl,
  (o) $CO_2H$ or
  (p) C(O)O—$C_{1-3}$ alkyl;
CycA is a $C_{3-6}$ cycloalkyl which is unsubstituted, or substituted with from 1 to 3 substituents each of which is independently F or $C_{1-4}$ alkyl;
each HetA is independently a heteroaryl selected from the group consisting of pyrrolyl, pyrazolyl, imidazolyl, triazolyl, tetrazolyl, pyridyl, pyrazinyl, quinolyl, isoquinolyl, and quinoxalinyl, wherein the heteroaryl is unsubstituted, or substituted with from 1 to 3 substituents each of which is independently selected from the group consisting of $CH_3$, $CF_3$, OH, $OCH_3$, $OCF_3$, Cl, Br, F, CN, $NH_2$, N(H)$CH_3$, N($CH_3$)$_2$, C(O)$CH_3$, $CO_2CH_3$ and $SO_2CH_3$; and
HetB is a saturated heterocyclic ring selected from the group consisting of tetrahydrofuranyl, pyrrolidinyl, piperidinyl, piperazinyl, morpholinyl, or thiomorpholinyl in which the S is optionally oxidized to S(O) or S(O)$_2$, and wherein the ring is unsubstituted, or substituted with 1 or 2 substituents each of which is independently selected from the group consisting of $CH_3$, $CH_2CH_3$, oxo, C(O)N($CH_3$)$_2$, C(O)$CH_3$, $CO_2CH_3$, and S(O)$_2CH_3$.

In some embodiments, the invention is directed to a pharmaceutical composition comprising an effective amount of any compound described above and pharmaceutically salts thereof, and a pharmaceutically acceptable carrier.

In some embodiments, the invention is directed to a method for the treatment or prophylaxis of infection by HIV or for the treatment, prophylaxis, or delay in the onset of AIDS in a subject in need thereof, which comprises administering to the subject an effective amount of any compound described above or a pharmaceutically acceptable salt thereof.

In some embodiments, the invention is directed to any compound described above, and pharmaceutically salts thereof, for use in the preparation of a medicament for the inhibition of HIV protease, for the treatment or prophylaxis of infection by HIV, or for the treatment, prophylaxis, or delay in the onset of AIDS in a subject in need thereof.

In some embodiments, the invention is directed to a pharmaceutical composition comprising an effective amount of a any compound described above and pharmaceutically salts thereof, and a pharmaceutically acceptable carrier.

In some embodiments, the invention is directed to a method for the treatment or prophylaxis of infection by HIV or for the treatment, prophylaxis, or delay in the onset of AIDS in a subject in need thereof, which comprises administering to the subject an effective amount of any compound described above or a pharmaceutically acceptable salt thereof.

Other embodiments, aspects and features of the present invention are either further described in or will be apparent from the ensuing description, examples and appended claims.

DETAILED DESCRIPTION OF THE INVENTION

The present invention includes sulfonamide compounds of Formula I above and pharmaceutically acceptable salts thereof. The compounds encompassed by Formula I include compounds which are HIV protease inhibitors.

Unless expressly stated to the contrary or clear from the context, a reference to compounds of the present invention refers to all compounds encompassed by Formula I, whether or not they act as prodrugs.

A first embodiment of the present invention (alternatively referred to herein as "Embodiment E1) is a compound of Formula I, or pharmaceutically acceptable salt thereof, wherein $R^1$ is selected from the group consisting of $CH_3$, $CH_2CH_3$, CH($CH_3$)$_2$, $CH_2CH_2CH_3$, $CH_2CH_2CH_2CH_3$, $CH_2CH(CH_3)_2$, $CH_2CH_2CH(CH_3)_2$, $CH_2CH_2CH_2F$, CycA, $CH_2$-CycA and $CH_2$-HetA, and all other variables are as originally defined (i.e., as defined for Compound I in the Summary of the Invention).

A second embodiment of the present invention ("Embodiment E 2") is a compound of Formula I, or pharmaceutically acceptable salt thereof, wherein $R^2$ is selected from the group consisting of $CH_2OH$, CH($CH_3$)OH, $CH_2NH_2$, CH($CH_3$)$NH_2$, $CH_2OR^P$ and CH($CH_3$)—$OR^P$, wherein $R^P$ is selected from the group consisting of P(O)(OH)$_2$, P(O)(ONa)$_2$ and C(O)$CH_3$, A sixth embodiment of the present invention ("Embodiment E 6") is a compound of Formula I, or pharmaceutically acceptable salt thereof, wherein all other variables are as defined in the first embodiment, or as originally defined (i.e., as defined for Compound I in the Summary of the Invention).

A third embodiment of the present invention ("Embodiment E 3") is a compound of Formula I, or pharmaceutically acceptable salt thereof, wherein $R^{3A}$ is H, wherein all other variables are as defined in either the first or second embodiments, or as originally defined (i.e., as defined for Compound I in the Summary of the Invention).

A fourth embodiment of the present invention ("Embodiment E 4") is a compound of Formula I, or pharmaceutically acceptable salt thereof, wherein L is selected from the group consisting of $CH_2$, NH, O, S and a single bond, wherein all other variables are as defined in any of the first through third embodiments, or as originally defined (i.e., as defined for Compound I in the Summary of the Invention).

A fifth embodiment of the present invention ("Embodiment E 5") is a compound of Formula I, or pharmaceutically acceptable salt thereof, wherein Ring A is selected from the group consisting of:

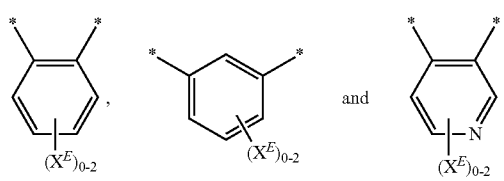

each $X^E$ is independently selected from the group consisting of:
(1) $CH_3$,
(2) $CH_2CH_3$,
(3) $CF_3$,
(4) OH,
(5) $OCH_3$,
(6) $OCF_3$,
(7) Cl, (8) Br,
(9) F and
(10) CN,
wherein all other variables are as defined in any of the first through fourth embodiments, or as originally defined (i.e., as defined for Compound I in the Summary of the Invention).

A sixth embodiment of the present invention ("Embodiment E 6") is a compound of Formula I, or pharmaceutically acceptable salt thereof, wherein $R^{4A}$ is selected from the group consisting of:

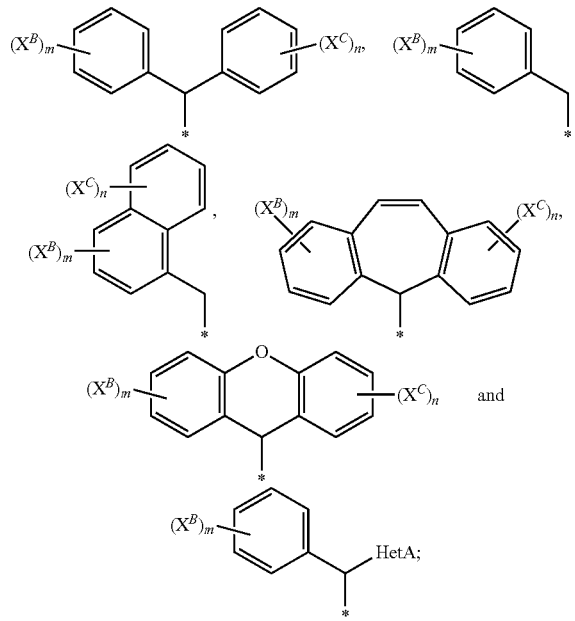

$R^{4B}$ is H;
each $X^B$ and each $X^C$ are independently selected from the group consisting of:
(1) $CH_3$,
(2) $CH_2CH_3$,
(3) $CF_3$,
(4) OH,
(5) $OCH_3$,
(6) $OCF_3$,
(7) Cl,
(8) Br,
(9) F,
(10) CN,
(11) $NH_2$,
(12) $N(H)CH_3$,
(13) $N(CH_3)_2$,
(14) $C(O)CH_3$,
(15) $C(O)OCH_3$,
(16) $CH_2OH$, and
(17) $CH_2OCH_3$,
wherein all other variables are as defined in any of the first through fifth embodiments, or as originally defined (i.e., as defined for Compound I in the Summary of the Invention).

A seventh embodiment of the present invention ("Embodiment E 7") is a compound of Formula I, or pharmaceutically acceptable salt thereof, wherein R5 is selected from the group consisting of H, $CH_3$, $C(O)CH_3$, $C(O)OCH_3$, $C(O)OC(CH_3)_3$, $C(O)N(CH_3)_2$, $C(O)$-morpholinyl, $C(O)$-pyridyl and $C(O)O—CH_2$-pyridyl,
wherein all other variables are as defined in any of the first through sixth embodiments, or as originally defined (i.e., as defined for Compound I in the Summary of the Invention).

An eighth embodiment of the present invention ("Embodiment E 8") is a compound of Formula I, or pharmaceutically acceptable salt thereof, wherein $R^6$ is H or $CH_3$, wherein all other variables are as defined in any of the first through seventh embodiments, or as originally defined (i.e., as defined for Compound I in the Summary of the Invention).

A ninth embodiment of the present invention ("Embodiment E 9") is a compound of Formula I, or pharmaceutically acceptable salt thereof, wherein $R^7$ is phenyl or benzothiaolyl, wherein the benzothioazolyl is unsubstituted and the phenyl is unsubstituted, or substituted with 1 or 2 $X^A$, each of which is independently selected from the group consisting of:
(1) $CH_3$,
(2) $CH_2CH_3$,
(3) $CF_3$,
(4) OH,
(5) $OCH_3$,
(6) $OCF_3$,
(7) Cl,
(8) Br,
(9) F,
(10) CN,
(11) $NH_2$,
(12) $N(H)CH_3$,
(13) $N(CH_3)_2$,
(14) $C(O)CH_3$,
(15) $C(O)OCH_3$,
(16) $CH_2OH$,
(17) $CH_2OCH_3$,
(18) $CH_2NH_2$,
(19) $CH_2N(H)CH_3$,
(20) $CH_2N(CH_3)_2$,
(21) $CH(CH_3)OH$,
(22) $CH(CH_3)OCH_3$,
(23) $CH(CH_3)NH_2$,
(24) $CH(CH_3)N(H)CH_3$ and
(25) $CH(CH_3)N(CH_3)_2$,
wherein all other variables are as defined in any of the first through eighth embodiments, or as originally defined (i.e., as defined for Compound I in the Summary of the Invention).

A tenth embodiment of the present invention ("Embodiment E 10") is a compound of Formula I, or pharmaceutically acceptable salt thereof, wherein CycA is cyclopropyl or cyclobutyl, wherein the cyclopropyl or cyclobutyl is unsubstituted, or substituted with 1 or 2 F,
wherein all other variables are as defined in any of the first through ninth embodiments, or as originally defined (i.e., as defined for Compound I in the Summary of the Invention).

An eleventh embodiment of the present invention ("Embodiment E11") is a compound of Formula I, or pharmaceutically acceptable salt thereof, wherein HetA is a heteroaryl selected from the group consisting of pyrrolyl, pyrazolyl, imidazolyl, and pyridyl, wherein the heteroaryl is unsubstituted, or substituted with from 1 or 2 substituents each of which is independently selected from the group consisting of $CH_3$, $CF_3$, OH, $OCH_3$, $OCF_3$, Cl, Br, F and CN, wherein all other variables are as defined in any of the first through tenth embodiments, or as originally defined (i.e., as defined for Compound I in the Summary of the Invention).

A twelfth embodiment of the present invention ("Embodiment E12") is a compound of Formula I, or pharmaceutically acceptable salt thereof, wherein:
$R^1$ is selected from the group consisting of $CH_3$, $CH_2CH_3$, $CH(CH_3)_2$, $CH_2CH_2CH_3$, $CH_2CH_2CH_2CH_3$, $CH_2CH$ (CH$_3$)$_2$, CH$_2$CH$_2$CH(CH$_3$)$_2$, CH$_2$CH$_2$CH$_2$F, cyclobutyl, CH$_2$-cyclopropyl, CH$_2$-cyclobutyl in which the cyclobutyl is substituted with 1 or 2 F, CH$_2$-pyrazolyl in which the pyrazolyl is substituted with 0-2 CH$_3$; and CH$_2$-isoxazolyl;

R$^2$ is selected from the group consisting of CH$_2$OH, CH(CH$_3$)OH, and CH$_2$NH$_2$;

L is selected from the group consisting of CH$_2$, S and a single bond;

Ring A is selected from the group consisting of:

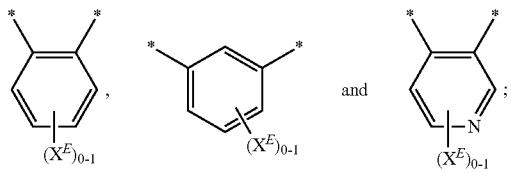

X$^E$ is selected from the group consisting of:
(1) CH$_3$,
(2) CF$_3$,
(4) OH,
(5) OCH$_3$,
(6) OCF$_3$, and
(7) F;

R$^{4A}$ is selected from the group consisting of:

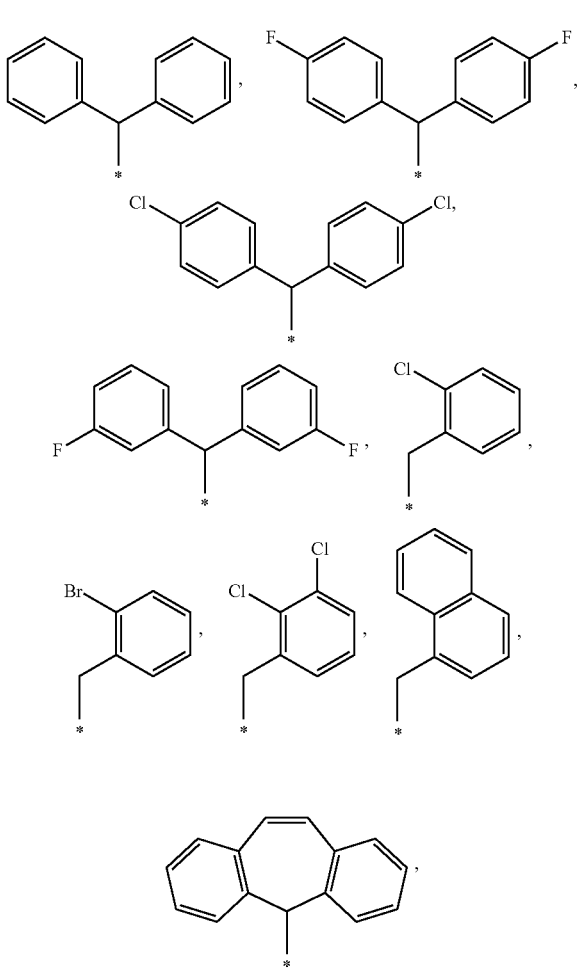

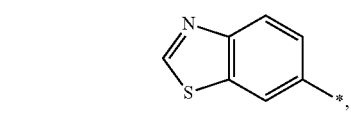

and

R$^5$ is selected from the group consisting of H, CH$_3$, C(O)OCH$_3$, C(O)OC(CH$_3$)$_3$ and C(O)O—CH$_2$-pyridyl; and R$^6$ is H or CH$_3$; and R$^7$ is:
(i) phenyl substituted with 1 or 2 X$^A$, wherein one X$^A$ is in the para position on the phenyl ring and is CH$_3$, Cl, Br, F, NH$_2$, C(O)CH$_3$, CH$_2$OH, or CH(CH$_3$)OH; and the other, optional X$^A$ is in the meta position on the phenyl ring and is Cl, Br, or F; or (ii)

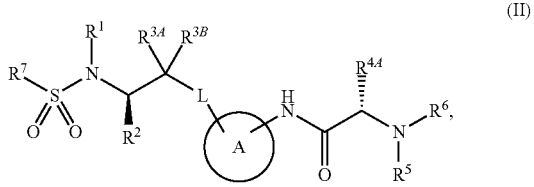

wherein all other variables are as defined in any of the first through eleventh embodiments, or as originally defined (i.e., as defined for Compound I in the Summary of the Invention).

A thirteenth embodiment of the present invention ("Embodiment E13") is a compound of Formula I, or pharmaceutically acceptable salt thereof, wherein:
R$^2$ is CH$_2$OH;
R$^5$ is C(O)OCH$_3$ and
R$^6$ is H,
wherein all other variables are as defined in any of the first through twelfth embodiments, or as originally defined (i.e., as defined for Compound 1 in the Summary of the Invention).

A fourteenth embodiment of the present invention ("Embodiment E14") is a compound of Formula II, and pharmaceutically salts thereof, (II)

wherein all other variables are as originally defined (i.e., as defined for Compound I in the Summary of the Invention).

A fifteenth embodiment of the present invention ("Embodiment E15") is a compound of of Formula III, and pharmaceutically salts thereof,

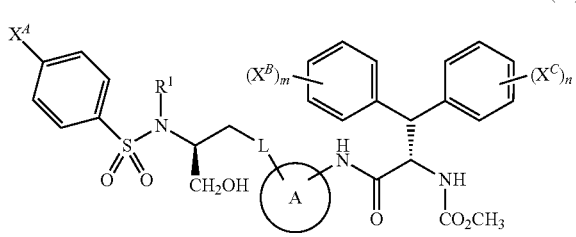

(III)

wherein:
$R^1$ is selected from the group consisting of $CH_3$, $CH_2CH_3$, $CH(CH_3)_2$, $CH_2CH_2CH_3$, $CH_2CH_2CH_2CH_3$, $CH_2CH(CH_3)_2$, $CH_2CH_2CH(CH_3)_2$, $CH_2CH_2CH_2F$, cyclobutyl, $CH_2$-cyclopropyl, $CH_2$-cyclobutyl in which the cyclobutyl is substituted with 1 or 2 F and $CH_2$-pyrazolyl in which the pyrazolyl is substituted with 0-2 $CH_3$, $CH_2$-isoxazolyl 1 or 2 $CH_3$;
L is selected from the group consisting of $CH_2$, S and a single bond;
Ring A is selected from the group consisting of:

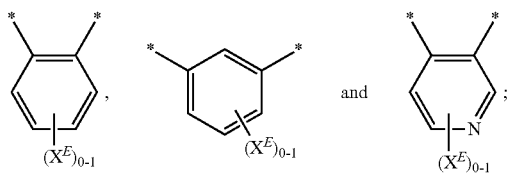

Wherein the asterisks (*) denote the points of attachment to the rest of the compound;
$X^E$ is selected from the group consisting of:
(1) $CH_3$;
(2) $CF_3$;
(4) OH;
(5) $OCH_3$;
(6) $OCF_3$; and,
(7) F;
$X^A$ is selected from the group consisting of $NH_2$, $C(O)CH_3$, $CH_2OH$ and $CH(CH_3)OH$;
each $X^B$ and each $X^C$ are independently selected from the group consisting of:
(1) $CH_3$;
(2) $CH_2CH_3$;
(3) $CF_3$;
(4) OH;
(5) $OCH_3$;
(6) $OCF_3$;
(7) Cl;
(8) Br;
(9) F;
(10) CN;
(11) $NH_2$;
(12) $N(H)CH_3$;
(13) $N(CH_3)_2$;
(14) $C(O)CH_3$;
(15) $C(O)OCH_3$;
(16) $CH_2OH$; and,
(17) $CH_2OCH_3$;
wherein m is an integer equal to 0, 1, or 2; and
n is an integer equal to 0, 1, or 2, and wherein all other variables are as originally defined (i.e., as defined for Compound I in the Summary of the Invention).

A sixteenth embodiment of the present invention ("Embodiment E16") is a compound of of Formula I, or a pharmaceutically acceptable salt thereof wherein:
$R^1$ is selected from the group consisting of $CH_2CH(CH_3)_2$ and $CH_2CH_2CH(CH_3)_2$; and
Ring A is selected from the group consisting of:

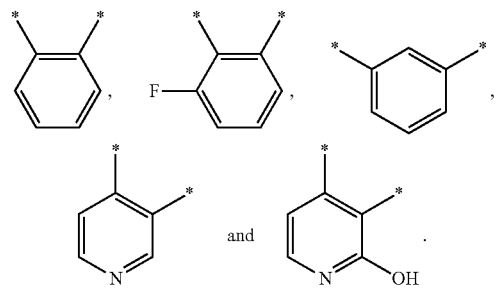

and wherein all other variables are as defined in any of the first through thirteenth embodiments, or as originally defined (i.e., as defined for Compound I in the Summary of the Invention).

A seventeenth embodiment of the present invention ("Embodiment E17") is a compound of of Formula 1, or a pharmaceutically acceptable salt thereof wherein m and n are either both 0 or both 1; and $X^B$ and $X^C$ are (i) both F and both para substituents, (ii) both F and both meta substituents, or (iii) both Cl and both para substituents and wherein all other variables are as defined in any of the first through thirteenth embodiments, the sixteenth embodiment, or as originally defined (i.e., as defined for Compound I in the Summary of the Invention).

An eighteenth embodiment of the present invention ("Embodiment E18") is a compound of of Formula I, or a pharmaceutically acceptable salt thereof wherein:
$R^1$ is selected from the group consisting of propyl-d9; isopropyl; isobutyl; isobutyl-d9; cyclopropylmethyl; isoamyl, (3,3-difluorocyclobutyl)methyl; (1,3-dimethyl-1H-pyrazol-4-yl)methyl; (1H-pyrazol-4-yl)methyl; (isoxazol-4-yl)methyl and (4-methylpyrimidin-5-yl)methyl;
$R^2$ is $CH_2OH$;
$R^{3A}$ and $R^{3B}$ are independently selected from the group consisting of H and D;
L is selected from the group consisting of $-CH_2-$; $-CD_2-$; $-S-$; $-S(O)-$; and $-S(O)_2-$;
A is selected from the group consisting of

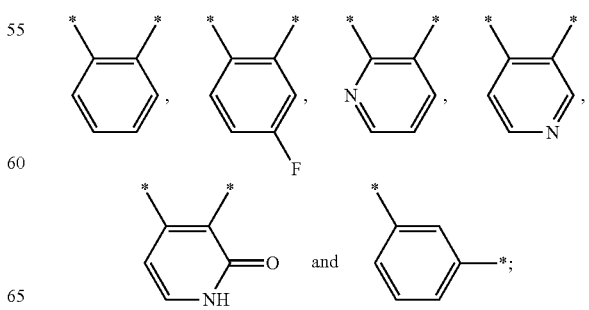

$R^{4A}$ is selected from the group consisting of

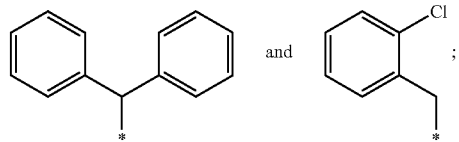 [SMILES: *C(c1ccccc1)c1ccccc1 ; *Cc1ccccc1Cl]

and $R^{4B}$ is H;
$R^5$ is —C(O)OCH;
$R^6$ is H; and,
$R^7$ is selected from the group consisting of

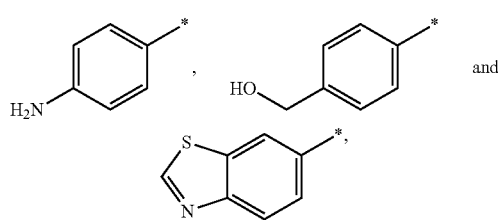

and wherein all other variables are as defined in any of the first through thirteenth embodiments, the sixteenth embodiment, the seventeenth embodiment or as originally defined (i.e., as defined for Compound I in the Summary of the Invention).

A nineteenth embodiment of the present invention ("Embodiment E19") is a compound of of Formula I, or a pharmaceutically acceptable salt thereof wherein:
$R^1$ is is selected from the group consisting of isobutyl, isoamyl, (3,3-difluorocyclobutyl)methyl, (1,3-dimethyl-1H-pyrazol-4-yl)methyl, (1H-pyrazol-4-yl)methyl and (isoxazol-4-yl)methyl;
$R^2$ is CH$_2$OH;
$R^{3A}$ and $R^{3B}$ are H;
L is —CH$_2$—;
A is

$R^{4B}$ is H;
$R^5$ is —C(O)OCH;
$R^6$ is H; and,
$R^7$ is

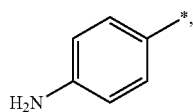

and wherein all other variables are as defined in any of the first through thirteenth embodiments, the sixteenth through the eighteenth embodiments, or as originally defined (i.e., as defined for Compound I in the Summary of the Invention).

A twentieth embodiment of the present invention ("Embodiment E20") is a compound selected from the group consisting of:

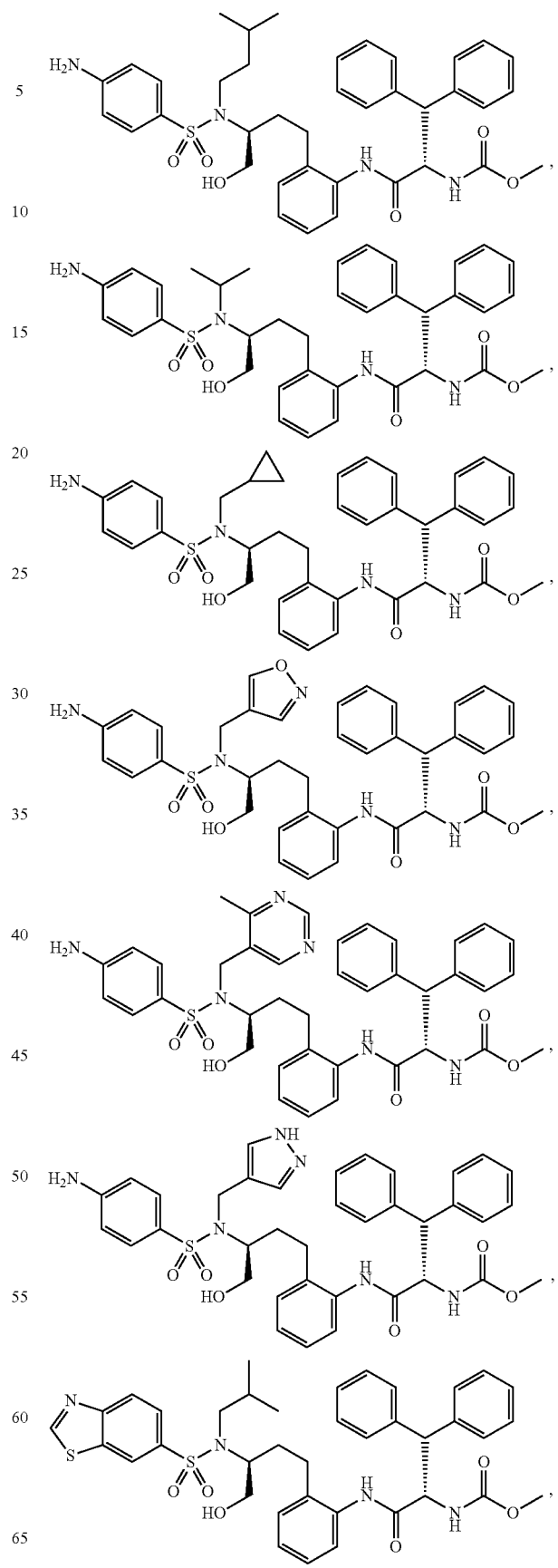

19
-continued
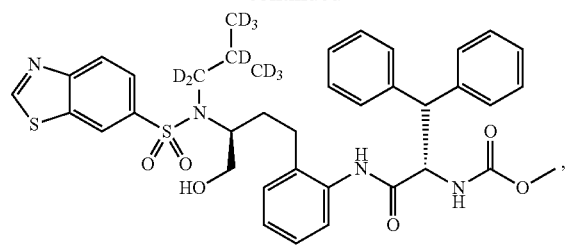
,
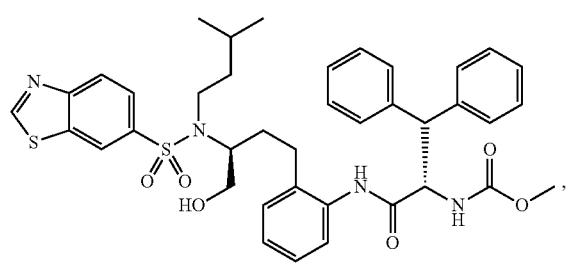
,
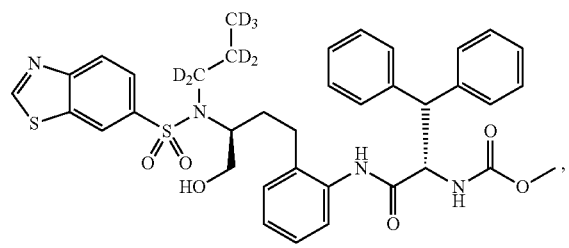
,
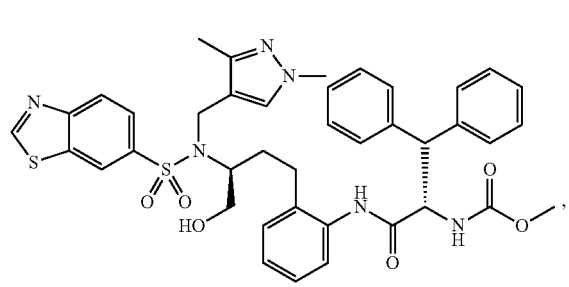
,
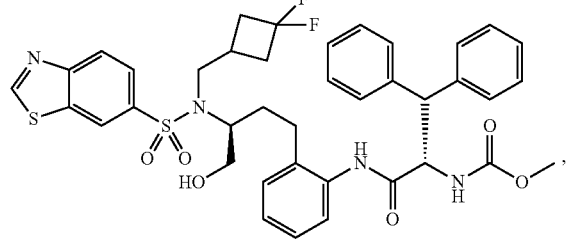
,
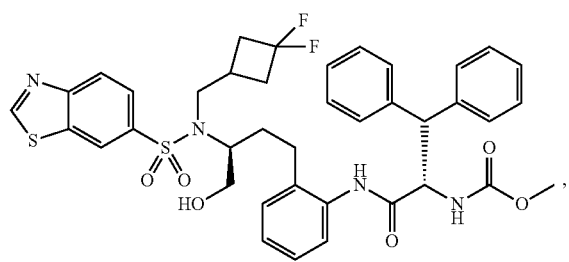
,
20
-continued
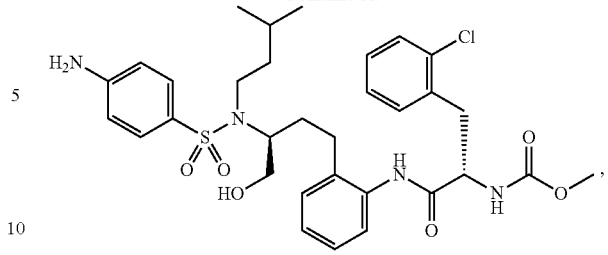
,
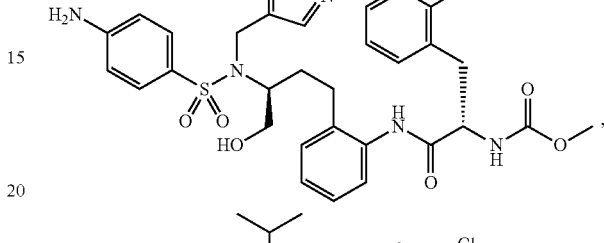
,
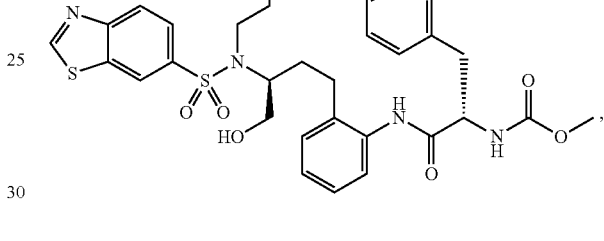
,
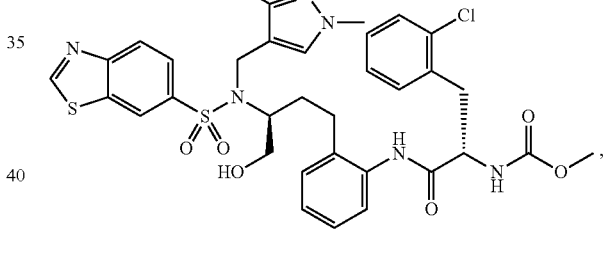
,
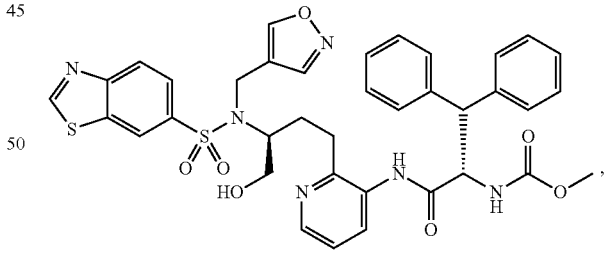
,
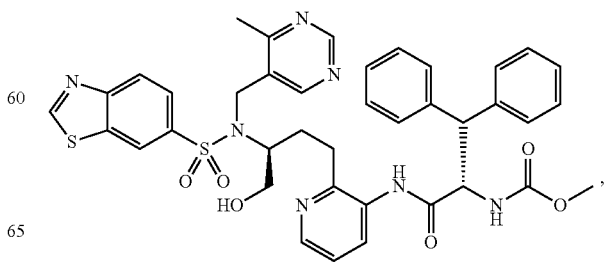
,

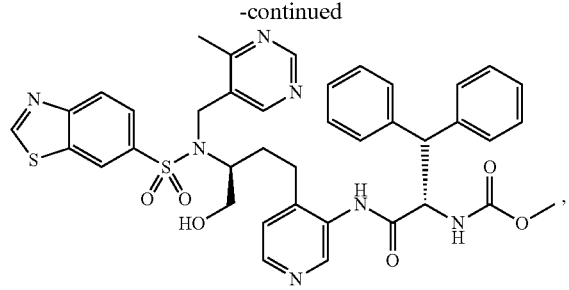
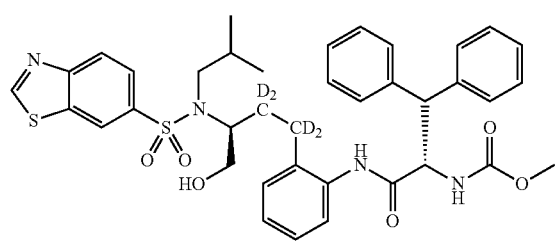
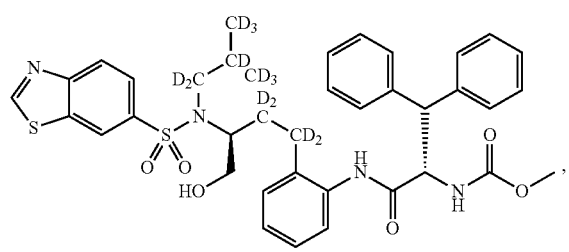
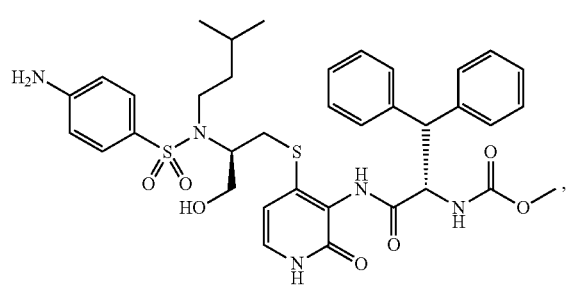
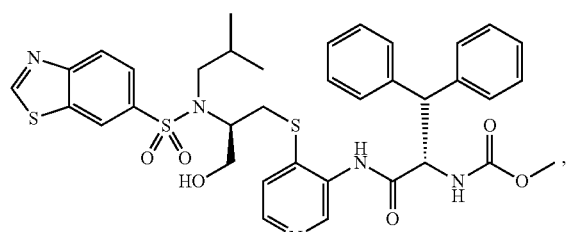
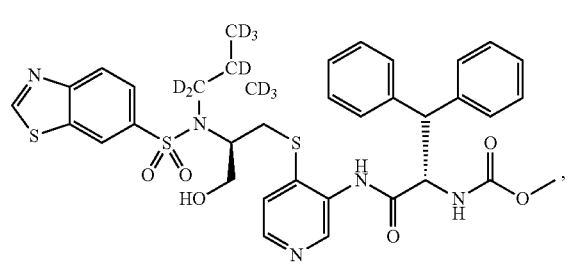
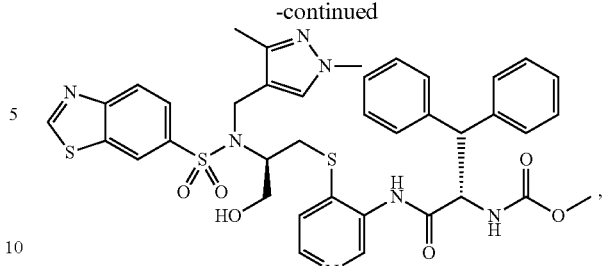
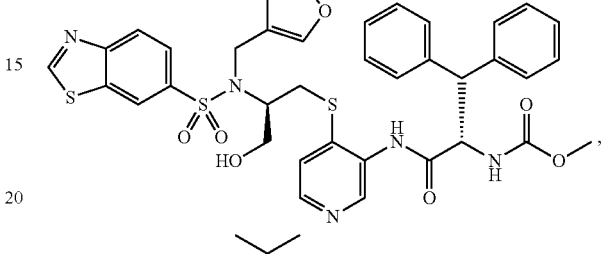
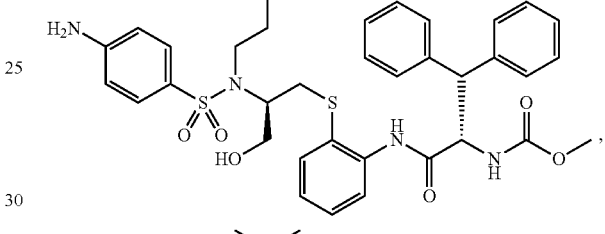
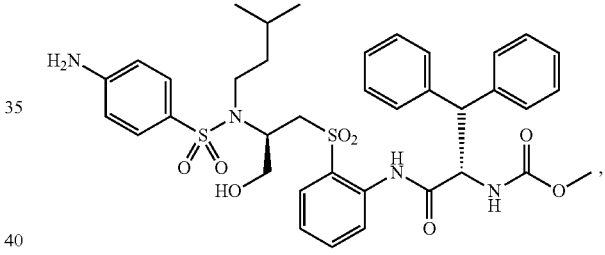
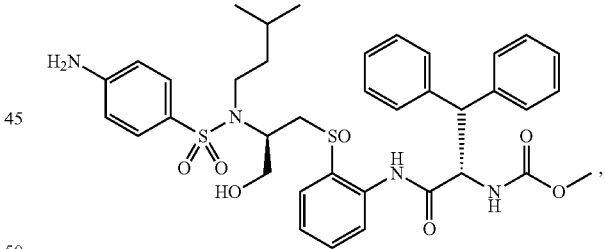
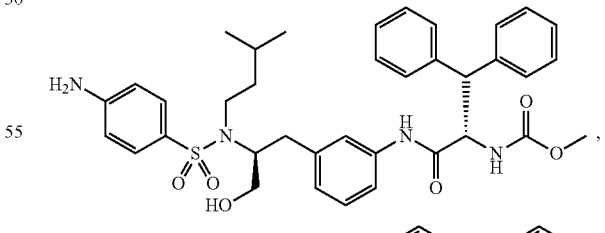
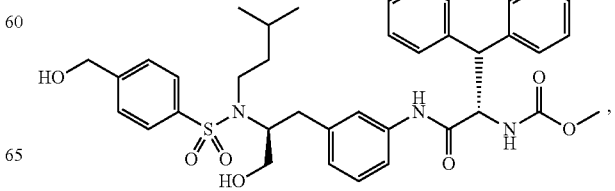

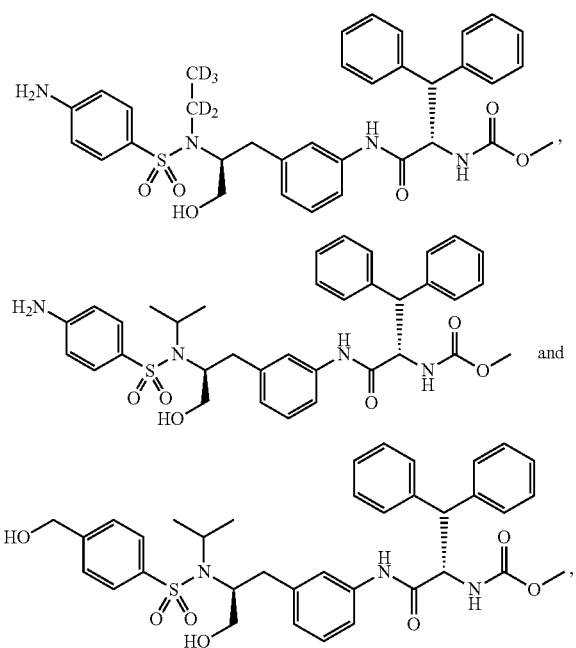

and pharmaceutically acceptable salts thereof.

A twenty-first embodiment of the present invention ("Embodiment E21") is a compound selected from the group consisting of:

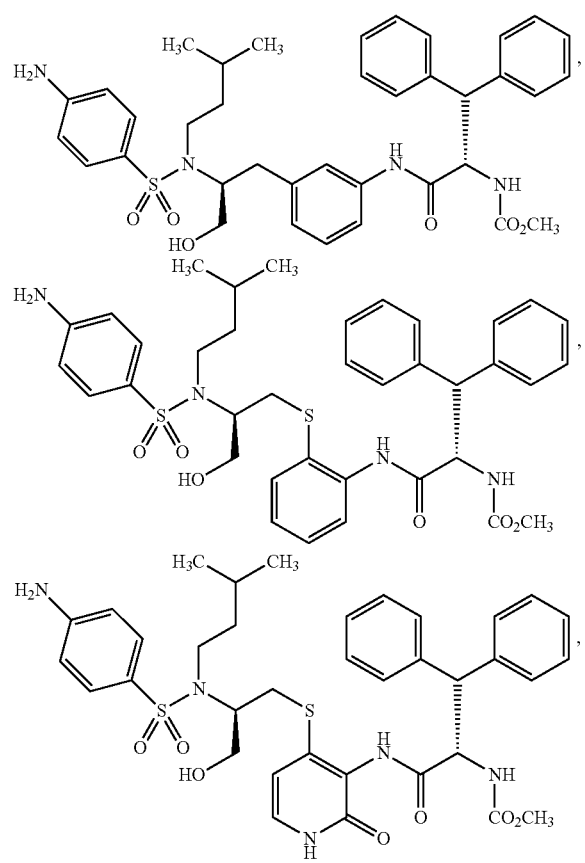

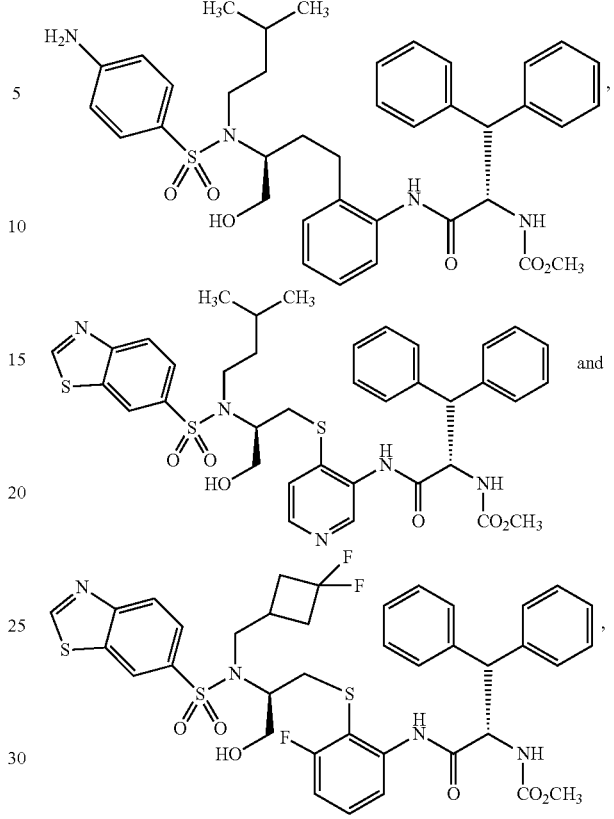

and pharmaceutically acceptable salts thereof.

A twenty-second embodiment of the present invention ("Embodiment E22") is a compound of Formula I, or a pharmaceutically acceptable salt thereof, (i) for use in, (ii) for use as a medicament for, or (iii) for use in the manufacture/preparation of a medicament for:
(a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of the free base or pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (i.e., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including via subcutaneous injections, intravenous, intramuscular, intrastemal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences,* 18$^{th}$ edition, edited by A. R. Gennaro, Mack Publishing Co., 1990 and in *Remington—The Science and Practice of Pharmacy,* 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/ or post-exposure, in combination with effective amounts of one or more anti-HIV agents selected from HIV antiviral agents, imunomodulators, antiinfectives, or vaccines useful for treating HIV infection or AIDS, such as those disclosed in Table 1 of WO 01/38332 or in the Table in WO 02/30930.

Suitable HIV antivirals for use in combination with the compounds of the present invention include, for example, those listed in Table A as follows:

TABLE A

Antiviral Agents for Treating HIV infection or AIDS

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T,didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), or the 59$^{th}$ edition (2005). The dosage ranges for a compound of the invention in these combinations are the same as those set forth above.

Additional embodiments of the invention include the pharmaceutical compositions, combinations and methods and uses set forth in the preceding paragraphs, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso- propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

An asterisk ("*") as the end of an open bond in a chemical group denotes the point of attachment of the group to the rest of the compound.

The term "aryl" refers to phenyl and naphthyl. The aryl of particular interest is phenyl.

The term "heteroaryl" refers to (i) a 5- or 6-membered heteroaromatic ring containing from 1 to 3 heteroatoms independently selected from N, O and S, or (ii) a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydropyranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as unsubstituted, or substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

The compounds of the present invention can form salts which are also within the scope of this invention, and reference to a compound of any of Formulas I, II, or III, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of any of Formulas I, II, or III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. Salts of the Compounds of Formulas I, II, or III may be formed, for example, by reacting a compound of Formulas I, II, or III with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. For example, if a compound of Formula (I) incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

Polymorphic forms of the compounds of formula I, and of the salts, solvates and prodrugs of the compounds of formula I, are intended to be included in the present invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

Abbreviations employed herein include the following: Bn=benzyl; BOC (or Boc)=t-butyloxycarbonyl; Boc$_2$O=di-t-butyl carbonate; BOP=benzotriazol-1-yloxytris-(dimethylamino)phosphonium; BSA=bovine serum albumin; CBS=Corey, Bakshi, Shibata chiral oxazaborolidine mediated ketone reduction; Cbz=benzyloxycarbonyl; DBU=1,8-diazabicyclo[5.4.0]undec-7-one; DCAD=di-(4-chlorobenzyl)azodicarboxylate; DCE=1,2-dichloroethane; DCM=dichloromethane; DEAD=diethyl azodicarboxylate; DIAD=diisopropylazodicarboxylate; Dibal-H=diisobutylaluminum hydride; DMAP=4-dimethylaminopyridine; DMF=dimethylformamide; DMSO=dimethyl sulfoxide; EDC=1-ethyl-3-(3-dimethylaminopropyl)carbodiimide; Et=ethyl; EtOAc=ethyl acetate; EtOH=ethanol; G-2G=Grubbs catalyst, 2$^{nd}$ generation; HOAt=1-hydroxy-7-azabenzotriazole; HPLC=high performance liquid chromatography; HSU=hydroxysuccinimide; i-PrOH=isopropanol; LAH=lithium aluminum hydride; LC-MS=liquid chromatography-mass spectroscopy; Me=methyl; MeOH=methanol; MOC=methoxycarbonyl; Ms=mesyl or methanesulfonyl; NMR=nuclear magnetic resonance; Ph=phenyl; RCM=ring closing metathesis; Piv=pivaloyl; PPTS=pyridinium p-toluene sulfonate; PyBrOP=bromo-tris-pyrrolidinophosphonium hexafluorophosphate; SCX=strong cation exchange resin; STP=standard temperature and pressure (i.e., 25° C. & 1 atmosphere); TBS=tert-butyldimethylsilyl; TBDPS=tert-butyl(diphenyl) silyl; TBDPSCl=tert-butyl(dimethyl)silyl chloride; TEA=triethylamine; TFA=trifluoroacetic acid; THF=tetrahydrofuran; TLC=thin layer chromatography; TMAF=tetramethyl ammonium fluoride; TMSCHN$_2$=trimethylsilyl diazomethane; TPAP=tetrapropylammonium perruthenate; TPP=triphenylphosphine.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl unsubstituted, or substituted with one or more $X^A$.

PREPARATIVE EXAMPLES

Schemes

Compounds of the present invention can be prepared according to Scheme 1, as indicated below. Thus the carboxylic acid group of a suitable substituted D-serine derivative can be reduced to an aldehyde. Alternatively, the same aldehyde can be prepared by oxidation of the primary alcohol of a suitable substituted L-serine derivative. The resulting aldehyde can then be used to couple with a phosphonium salt, such as triphenyl(2-nitrobenzyl) phosphonium bromide in the presence of a base under Witting reaction conditions to render an olefine. The olefine and the nitro group can be then hydrogenated in the presence of a palladium catalyst and hydrogen The resulting free amine can be coupled to a carboxylic acid using different coupling agents such as PyBOP, HBTU or HATU. The protecting group on the aliphatic amine in the amino-alcohol moiety can be cleaved in the presence of a strong acid like TFA, then the primary amino group can be reacted with a sulfonyl chloride to render a sulfonamide or alkylated to afford a secondary amine. The sulfonamide is then alkylated using an alcohol under Mitsunobu conditions or a suitable alkylating reagent such as an alkyl bromide in the presence of a base to obtain a tertiary sulfonamide. Alternatively, the secondary amine can be reacted with a sulfonyl chloride to obtain the tertiary sulfonamide. The protecting group on the primary alcohol in the amino-alcohol moiety is then removed in the presence of a fluoride bearing reagent, such as HF or TBAF, to free the phamacophoric moiety. Further optional manipulations, such as functional group conversion, can also be considered.

Scheme 1

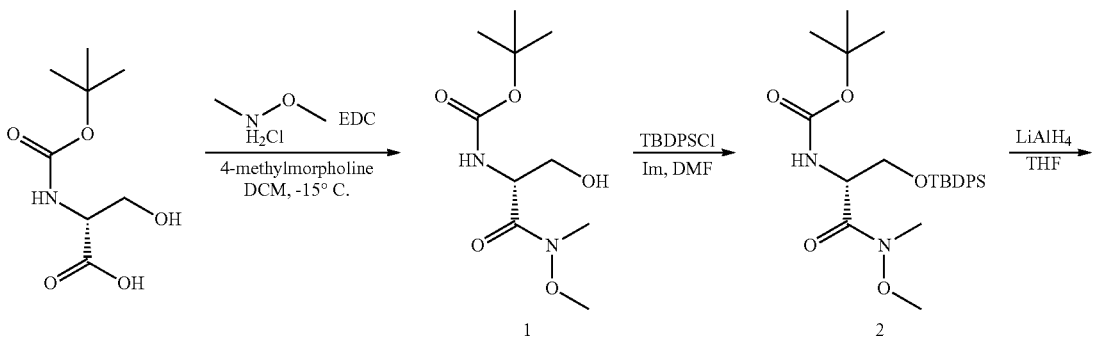

-continued
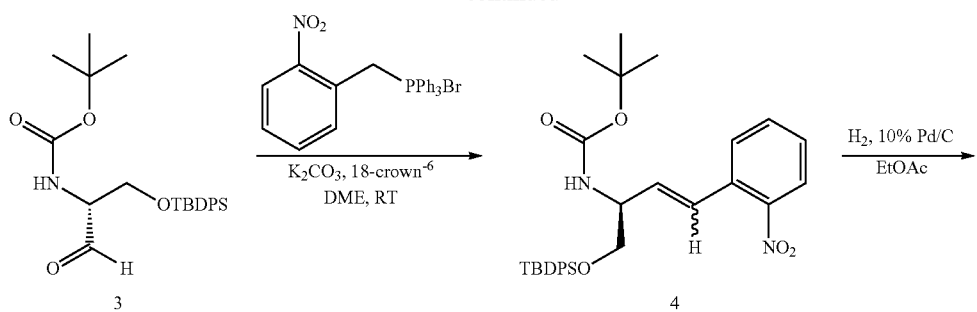
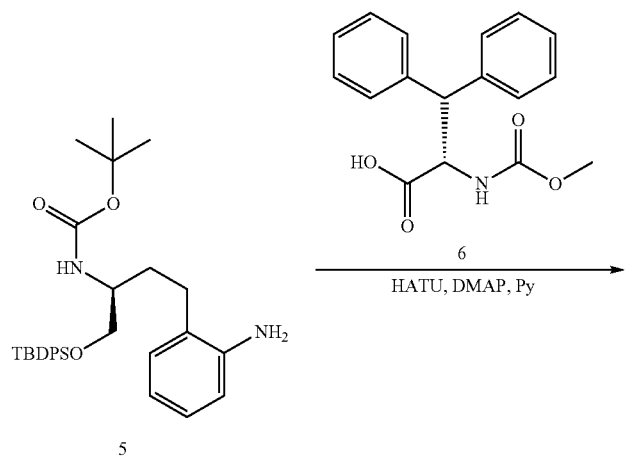
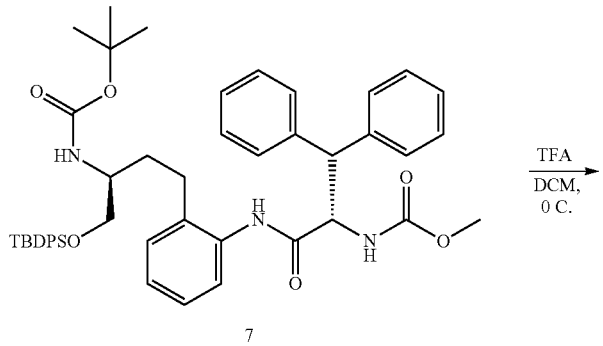
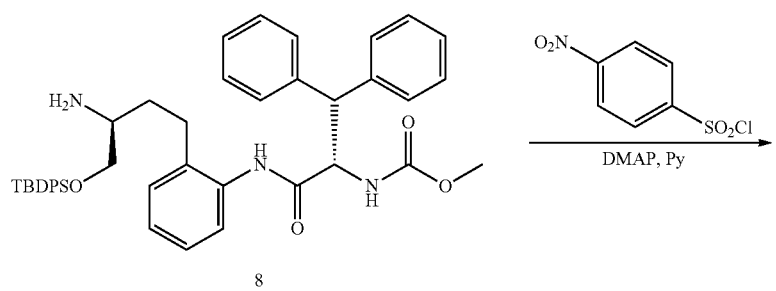

-continued
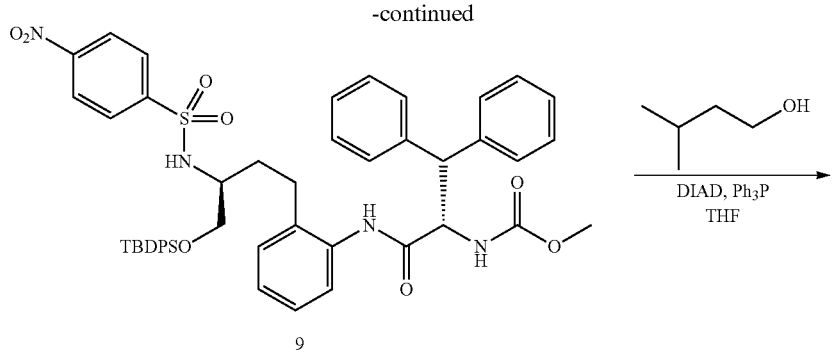
9
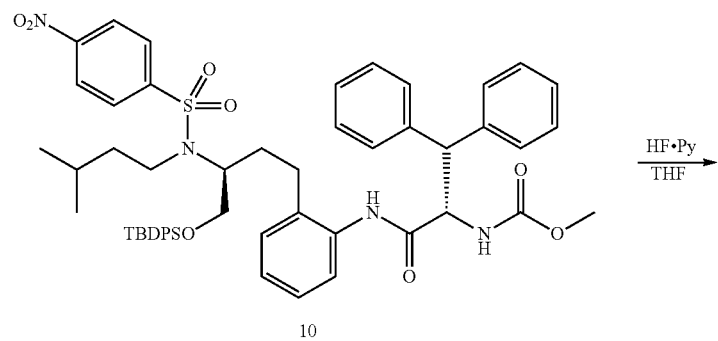
10
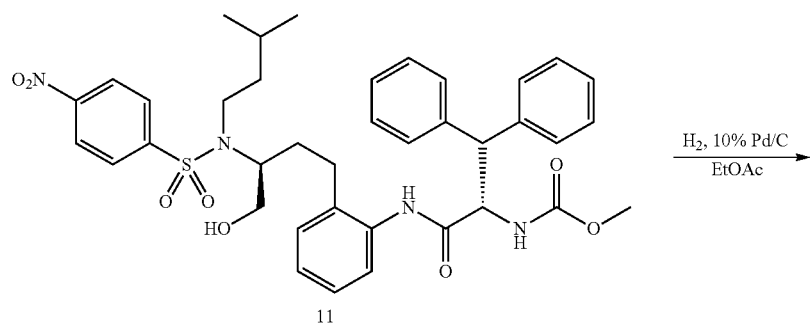
11
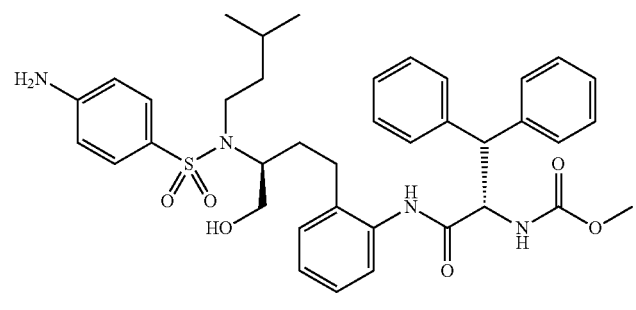
12

Example 1

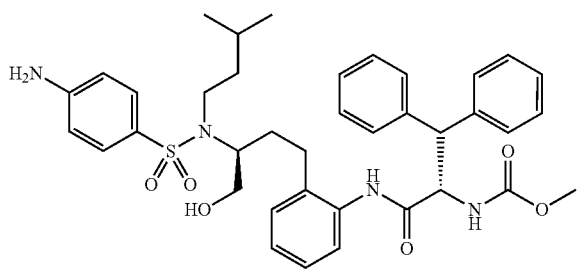 [SMILES: COC(=O)N[C@H](C(=O)Nc1ccccc1CC[C@@H](CO)N(CCC(C)C)S(=O)(=O)c1ccc(N)cc1)C(c1ccccc1)c1ccccc1]

N-{2-[(3S)-3-{[(4-aminophenyl)sulfonyl](3-methyl-butyl)amino}-4-hydroxybutyl]phenyl}-Nα-(methoxycarbonyl)-β-phenyl-L-phenylalaninamide (12)

Step 1: $N^2$-(tert-butoxycarbonyl)-N-methoxy-N-methyl-D-serinamide (1)

A suspension of N-(tert-butoxycarbonyl)-D-serine (2.06 g, 10.05 mol) in dry DCM (40 ml), stirred at −15° C. (ice/salt bath) under $N_2$ atmosphere was treated with solid N,O hydroxylamine hydrochloride (1.104 g, 11 mmol) followed by N-methylmorpholine (1.202 g, 11.9 mmol). EDC (2011 mg, 10.49 mmol) was then added to the reaction flask in five equal portions over the first 40 min, after completely charged with EDC, the reaction mixture was further stirred at the same temperature for extra 1.5 h. Diluted with DCM, washed with aqueous 5% $KHSO_4$ followed by saturated solution of $NaHCO_3$, dried over $Na_2SO_4$ and stored under vacuum to give 1.93 g (7.78 mmol, 77% yield) of the title compound as a white solid. MS m/z=271.1 (MNa+).

Step 2: $N^2$-(tert-butoxycarbonyl)-O-[tert-butyl(diphenyl)silyl]-N-methoxy-N-methyl-D-serinamide (2)

A solution of $N^2$-(tert-butoxycarbonyl)-N-methoxy-N-methyl-D-serinamide (1, 1.93 g, 7.78 mmol) and imidazole (1.21 g, 17.81 mmol) in DMF (9 ml) stirred under $N_2$ at room temperature, was treated with neat tert-butyl(chloro)diphenylsilane (2.2 ml, 8.56 mmol) and further stirred for 17 h. Diluted with EtOAc, washed with 5% $KHSO_4$ in water, then sat $NaHCO_3$, dried over $Na_2SO_4$, filtered and concentrated. Purified through a chromatographic cartridge of silicagel (50 g) eluted with 10% to 60% EtOAc in hexane to give 3.55 g (94% yield) of title compound as colorless oil. MS: m/z=509.2 (MNa+).

Step 3: tert-butyl[(2R)-1-{[tert-butyl(diphenyl)silyl]oxy}-3-oxopropan-2-yl]carbamate (3)

A solution of $N^2$-(tert-butoxycarbonyl)-O-[tert-butyl(diphenyl)silyl]-N-methoxy-N-methyl-D-serinamide (2, 3.55 g, 7.30 mmol) in THF (70 ml) stirred at 0° C. under $N_2$ was treated with a 1M solution of $LiAlH_4$ in THF (10 mL, 10 mmol) (dropwise addition) and further stirred at the same temperature for 2 h. Quenched with slow addition of water, then diluted with EtOAc and washed with 5% $KHSO_4$ solution in water followed by saturated $NaHCO_3$; dried over $Na_2SO_4$, filtered and concentrated to give a colorless oil (3.12 g, 100% yield) characterized as the title compound. Submitted to the next reaction without further purification. MS: m/z=450.2 (MNa+).

Step 4: tert-butyl[(2S,3E)-1-{[tert-butyl(diphenyl)silyl]oxy}-4-(2-nitrophenyl)but-3-en-2-yl]carbamate (4)

A solution of tert-butyl[(2R)-1-{[tert-butyl(diphenyl)silyl]oxy}-3-oxopropan-2-yl]carbamate (3, 3.12 g, 7.3 mmol) in DME (30 ml) was treated with solid (2-nitrobenzyl)(triphenyl)phosphonium bromide(3.76 g, 7.86 mmol) (or any other suitable phosphonium salt), the mixture stirred at room temperature under $N_2$ atmosphere for 30 min and then the reaction flask was charged with a solid mixture of potassium carbonate (1.78 g, 12.86 mmol) and 18-crown-6 (219 mg, 0.83 mmol). The purple mixture was further stirred at the same temperature for 14 h; diluted with DCM, washed with saturated $NaHCO_3$, dried over $MgSO_4$, filtered and concentrated Purified through a chromatographic cartridge of silicagel (50 g) eluted with 10% to 35% EtOAc in hexane to get 1.52 g (38% yield) of title compound as light yellow oil. MS: m/z=569.2 (MNa+).

Step 5: tert-butyl[(2S)-4-(2-aminophenyl)-1-{[tert-butyl(diphenyl)silyl]oxy}butan-2-yl]carbamate (5)

A solution of tert-butyl[(2S,3E)-1-[tert-butyl(diphenyl)silyl]oxy}-4-(2-nitrophenyl)but-3-en-2-yl]carbamate (4, 1.525 g, 2.79 mmol) in EtOAc (50 ml) was stirred under $H_2$ atmosphere (balloon) in the presence of 10% Pd/C (721 mg, 24% mol) for 2 h, filtered through a pad of Celite and concentrated to render a colorless thick oil (1.44 g, 100% yield) characterized as the title compound. MS: m/z=519.2 (MH+).

Step 6: methyl[(2S)-1-({2-[(3S)-3-[(tert-butoxycarbonyl)amino]-4-{[tert-butyl(diphenyl)silyl]oxy}butyl]phenyl}amino)-1-oxo-3,3-diphenylpropan-2-yl]carbamate (7)

A mixture of tert-butyl[(2S)-4-(2-aminophenyl)-1-{[tert-butyl(diphenyl)silyl]oxy}butan-2-yl]carbamate (5, 242 mg, 0.466 mmol), N-(methoxycarbonyl)-β-phenyl-L-phenylalanine (6, 225 mg, 0.752 mmol) (or any other suitable carboxylic acid), HATU (318 mg, 0.836 mmol) and DMAP (50 mg, 0.409 mmol) was dissolved in dry Py (2 ml) and the mixture was stirred at room temperature under $N_2$ for 13 h. Quenched with water (0.5 mL), then diluted (DCM), washed with 5% $KHSO_4$ in water, then saturated $NaHCO_3$, dried over $MgSO_4$, filtered and concentrated. Purified through a chromatographic cartridge of silicagel (12 g) eluted with 10% to 30% EtOAc in hexane to give 305 mg (82% yield) of title compound as white foam, MS: m/z=822.2 (MNa+).

N-(methoxycarbonyl)-β-phenyl-L-phenylalanine (6)

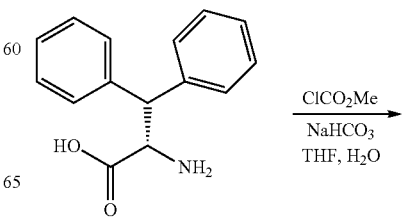

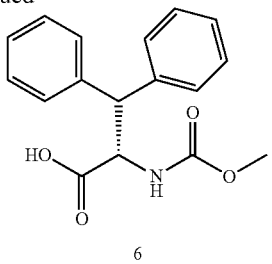

A suspension of L-diphenylalanine (13.87 g, 57.5 mmol) in THF (100 ml), and saturated NaHCO₃ (3 mL) stirred at 0° C. was treated with neat methyl chloroformate (11.81 g, 125 mmol) (slow addition), stirred at the same temperature for 10 min and then at room temperature for 14 h, made acidic by addition of 1M HCl and extracted with DCM, dried over MgSO4 filtered and concentrated to give title compound (17.1 g, 99% yield) as white solid. Used without further purification. MS: m/z=322.1 (MNa+).

Step 7: N-{2-[(3S)-3-amino-4-{[tert-butyl(diphenyl)silyl]oxy}butyl]phenyl}-Nα-(methoxycarbonyl)-β-phenyl-L-phenylalaninamide (8)

Compound methyl[(2S)-1-({2-[(3S)-3-[(tert-butoxycarbonyl)amino]-4-{[tert-butyl(diphenyl)silyl]oxy}butyl]phenyl}amino)-1-oxo-3,3-diphenylpropan-2-yl]carbamate (7, 305.4 mg, 0.382 mmol) was dissolved in a cold mixture of DCM (3 ml) and TFA (1 mL, 12.98 mmol) and the final solution stirred at 0° C. for 1.5 h, quenched at 0° C. by slow addition of saturated NaHCO₃, then diluted with DCM, washed with saturated NaHCO₃, dried over MgSO₄, filtered and concentrated to afford 255 mg (95% yield) of the title compound as white foam submitted to the next step without further purification. MS: m/z=700.3 (MH+).

Step 8: N-{2-[(3S)-4-{[tert-butyl(diphenyl)silyl]oxy}-3-{[(4-nitrophenyl)sulfonyl]amino}butyl]phenyl}-Nα-(methoxycarbonyl)-β-phenyl-L-phenylalaninamide (9)

A solution of N-{2-[(3S)-3-amino-4-{[tert-butyl(diphenyl)silyl]oxy}butyl]phenyl}-Nα-(methoxycarbonyl)-β-phenyl-L-phenylalaninamide (8, 255.1 mg, 0.364 mmol) in pyridine (2 mL) was treated with solid p-nitro benzenesulfonyl chloride (247 mg, 1.115 mmol) (or any other suitable sulfonyl chloride) and the mixture stirred at room temperature for 13 h, quenched with sat. NaHCO₃ (0.5 mL), diluted with DCM, washed with sat. NaHCO₃ then aqueous 5% KHSO₄ then saturated NaHCO₃, dried over MgSO4, filtered and concentrated to get 326 mg (100% yield) of the title compound, which was used without further purification for the next step. MS: m/z=885.3 (MH+).

Step 9: N-{2-[(3S)-4-{[tert-butyl(diphenyl)silyl]oxy}-3-{(3-methylbutyl)[(4-nitrophenyl)sulfonyl]amino}butyl]phenyl}-Nα-(methoxycarbonyl)-β-phenyl-L-phenylalaninamide (10)

A solution of N-{2-[(3S)-4-{[tert-butyl(diphenyl)silyl]oxy}-3-{[(4-nitrophenyl)sulfonyl]amino}butyl]phenyl}-Nα-(methoxycarbonyl)-β-phenyl-L-phenylalaninamide (9, 160 mg, 0.181 mmol), Ph₃P (149 mg, 0.568 mmol) and isoamyl alcohol (89 mg, 1.01 mmol) (or any other suitable alcohol) in THF (1.5 ml) stirred at external temperature of 0° C. under N₂ atmosphere, was treated with neat DIAD (150 μL, 0.771 mmol) and the mixture stirred at the same temperature for 30 min and then at room temperature in the dark for 16 h, concentrated and purified in a cromatographic cartridge of silicagel (24 g) eluted with 10% to 40% EtOAc in hexane, to get 143 mg (83%) of the title compound as white foam MS: m/z=955.3 (MH+).

Step10: N-{2-[(3S)-4-hydroxy-3-{(3-methylbutyl)[(4-nitrophenyl)sulfonyl]amino}butyl]phenyl}-Nα-(methoxycarbonyl)-β-phenyl-L-phenylalaninamide (11)

A solution of N-{2-[(3S)-4-{[tert-butyl(diphenyl)silyl]oxy}-3-{(3-methylbutyl)[(4-nitrophenyl)sulfonyl]amino}butyl]phenyl}-Nα-(methoxycarbonyl)-β-phenyl-L-phenyl alaninamide (10, 141.3 mg, 0.148 mmol) in THF (1.5 ml) stirred at 0° C. in a plastic vial, was treated with a 70% solution of HF in pyridine (1.5 mL, 5.8 mmol), the plastic bottle was capped and the final mixture stirred at room temperature for 4 h. Diluted with EtOAc, washed with water followed by saturated NaHCO₃, dried over MgSO₄, filtered and concentrated. Purification made by passage through a chromatographic cartridge of silicagel (12 g) eluted with 20% to 60% EtOAc in hexane to give 74 g (69% yield) of title compound as white foam. MS: m/z=717.3 (MH+).

Step 11: N-{2-[(3S)-3-{[(4-aminopbenyl)sulfonyl](3-methylbutyl)amino}-4-hydroxybutyl]phenyl}-Nα-(methoxycarbonyl)-β-phenyl-L-phenylalaninamide (12)

A solution of N-{2-[(3S)-4-hydroxy-3-{(3-methylbutyl)[(4-nitrophenyl)sulfonyl]amino}butyl]phenyl}-Nα-(methoxycarbonyl)-β-phenyl-Lphenylalaninamide (11, 74 mg, 0.103 mmol) in EtOAc (15 ml) was stirred under H₂ atmosphere (balloon) in the presence of 10% Pd/C (62 mg, 56% mol) for 1.5 h, filtered through a pad of Celite and concentrated to render an white solid (59 mg, 83% yield) characterized as the title compound. MS: m/z=717.3 (MH+).

¹H NMR δ (ppm)(CH₃ CN-d₃): 8.13 (1 H, s), 7.55 (2 H, d, J=8.52 Hz), 7.45 (4 H, dd, J=7.39, 3.69 Hz), 7.39-7.18 (6 H, m), 7.10-7.05 (3 H, m), 7.00 (1 H, s), 6.71 (2 H, d, J=8.56 Hz), 5.13 (1 H, dd, J=11.45, 8.72 Hz), 4.82 (2 H, s), 4.45 (1 H, d, J=11.39 Hz), 3.67 (1 H, t, J=6.73 Hz), 3.65-3.60 (1 H, m), 3.60 (3H, s), 3.55-3.50 (1H, m), 3.26-3.15 (2 H, m), 3.12-3.03 (1 H, m), 2.45-2.20 (2H, m), 1.75-1.60 (1H, m), 1.60-1.49 (3 H, m), 1.45-1.35 (1H, m), 1.30 (1 H, s), 0.92 (6 H, d, J=6.00 Hz).

TABLE 1

Examples made following synthetic procedures analogous to those described for example 1

| Example number | Compound number | Structure | Characterization data MS : m/z |
|---|---|---|---|
| 2 | 13 | N-{2-[(3S)-3-{[(4-aminophenyl)sulfonyl](propan-2-yl)amino}-4-hydroxybutyl]phenyl}-Nα-(methoxycarbonyl)-β-phenyl-L-phenylalaninamide | 659.3 (MH+) |
| 3 | 14 | N-{2-[(3S)-3-{[(4-aminophenyl)sulfonyl](cyclopropylmethyl)amino}-4-hydroxybutyl]phenyl}-Nα-(methoxycarbonyl)-β-phenyl-L-phenylalaninamide | 671.2 (MH+) |
| 4 | 15 | N-{2-[(3S)-3-{[(4-aminophenyl)sulfonyl(isoxazol-4-ylmethyl)amino}-4-hydroxybutyl]phenyl}-Nα-(methoxycarbonyl)-β-phenyl-L-phenylalaninamide | 698.2 (MH+) |
| 5 | 16 | N-{2-[(3S)-3-{[(4-aminophenyl)sulfonyl][(4-methylpyrimidin-5-yl)methyl]amino}-4-hydroxybutyl]phenyl}-Nα-(methoxycarbonyl)-β-phenyl-L-phenylalaninamide | 723.2 (MH+) |

TABLE 1-continued

Examples made following synthetic procedures analogous to those described for example 1

| Example number | Compound number | Structure | Characterization data MS : m/z |
|---|---|---|---|
| 6 | 17 | N-{2-[(3S)-3-{[(4-aminophenyl)sulfonyl](1H-pyrazol-4-ylmethyl)amino}-4-hydroxybutyl]phenyl}-Nα-(methoxycarbonyl)-β-phenyl-L-phenylalaninamide | 697.3 (MH+) |
| 7 | 18 | N-(2-{(3S)-3-[(1,3-benzothiazol-6-ylsulfonyl)(2-methylpropyl)amino]-4-hydroxybutyl}phenyl)-Nα-(methoxycarbonyl)-β-phenyl-L-phenylalaninamide | 715.2 (MH+) |
| 8 | 19 | N-(2-{(3S)-3-[(1,3-benzothiazol-6-ylsulfonyl)(2-methylpropyl-d9)amino]-4-hydroxybutyl}phenyl)-Nα-(methoxycarbonyl)-β-phenyl-L-phenylalaninamide | 724.3 (MH+) |
| 9 | 20 | N-(2-{(3S)-3-[(1,3-benzothiazol-6-ylsulfonyl)(3-methylbutyl)amino]-4-hydroxybutyl}phenyl)-Nα-(methoxycarbonyl)-β-phenyl-L-phenylalaninamide | 729.2 (MH+) |

TABLE 1-continued

Examples made following synthetic procedures analogous to those described for example 1

| Example number | Compound number | Structure | Characterization data MS : m/z |
|---|---|---|---|
| 10 | 21 | N-(2-{(3S)-3-[(1,3-benzothiazol-6-ylsulfonyl)(propyl-d7)amino]-4-hydroxybutyl}phenyl)-Nα-(methoxycarbonyl)-β-phenyl-L-phenylalaninamide | 708.3 (MH+) |
| 11 | 22 | N-{2-[(3S)-3-{(1,3-benzothiazol-6-ylsulfonyl)[(1,3-dimethyl-1H-pyrazol-4-yl)methyl]amino}-4-hydroxybutyl]phenyl}-Nα-(methoxycarbonyl)-β-phenyl-L-phenylalaninamide | 767.2 (MH+) |
| 12 | 23 | N-{2-[(3S)-3-{(1,3-benzothiazol-6-ylsulfonyl)[(3,3-difluorocyclobutyl)methyl]amino}-4-hydroxybutyl]phenyl}-Nα-(methoxycarbonyl)-β-phenyl-L-phenylalaninamide | 763.2 (MH+) |
| 13 | 24 | N-{2-[(3S)-3-{(1,3-benzothiazol-6-ylsulfonyl)[(3,3-difluorocyclobutyl)methyl]amino}-4-hydroxybutyl]-5-fluorophenyl}-Nα-(methoxycarbonyl)-β-phenyl-L-phenylalaninamide | 781.2 (MH+) |

TABLE 1-continued

Examples made following synthetic procedures analogous to those described for example 1

| Example number | Compound number | Structure | Characterization data MS : m/z |
|---|---|---|---|
| 14 | 25 | N-{2-[(3S)-3-{[(4-aminophenyl)sulfonyl](3-methylbutyl)amino}-4-hydroxybutyl]phenyl}-2-chloro-Nα-(methoxycarbonyl)-L-phenylalaninamide | 645.3 (MH+) |
| 15 | 26 | N-{2[(3S)-3-{[(4-aminophenyl)sulfonyl](1H-pyrazol-4-ylmethyl)amino}-4-hydroxybutyl]phenyl}-2-chloro-Nα-(methoxycarbonyl)-L-phenylalaninamide | 655.2 (MH+) |
| 16 | 27 | N-(2-{(3S)-3-[(1,3-benzothiazol-6-ylsulfonyl)(3-methylbutyl)amino]-4-hydroxybutyl}phenyl)-2-chloro-Nα-(methoxycarbonyl)-L-phenylalaninamide | 687.1 (MH+) |
| 17 | 28 | N-{2-[(3S)-3-{(1,3-benzothiazol-6-ylsulfonyl)[(1,3-dimethyl-1H-pyrazol-4-yl)methyl]amino}-4-hydroxybutyl]phenyl}-2-chloro-Nα-(methoxycarbonyl)-L-phenylalaninamide | 725.2 (MH+) |

Compounds of the present invention may also be prepared according to Scheme 2, as indicated below. The aldehyde obtained in Scheme 1 can be directly converted to a terminal alkyne using, for example, Seyferth protocol, which in turn can be coupled with a suitable functionalized aryl group using Sonogashira coupling conditions. Then the disubstituted alkyne obtained can be subjected to the sequence of reactions described in scheme 1 (starting with hydrogenation of the triple bond) to provide the compounds of the invention.

Scheme 2
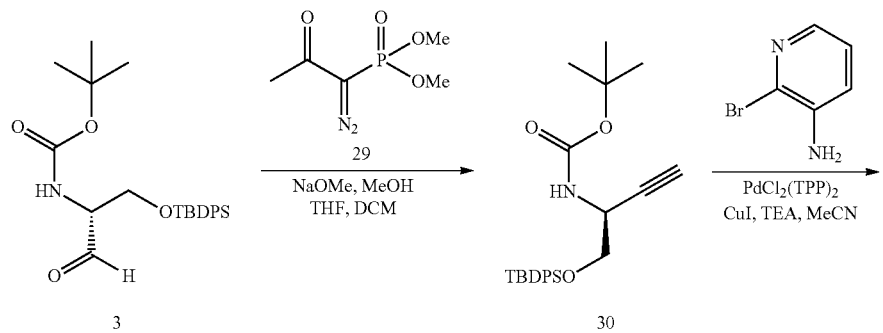
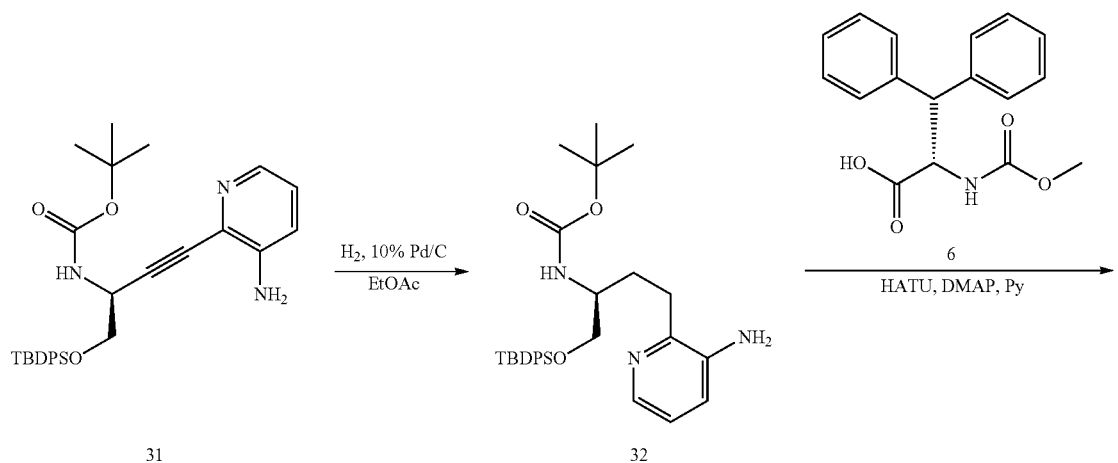
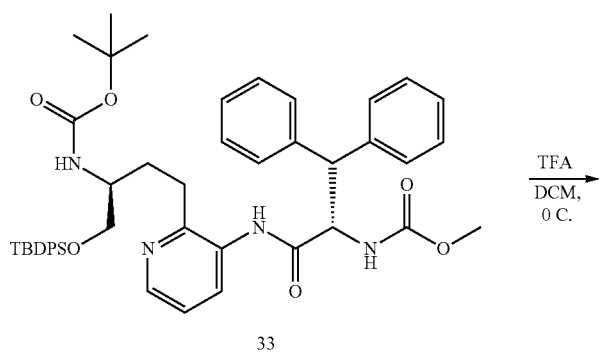
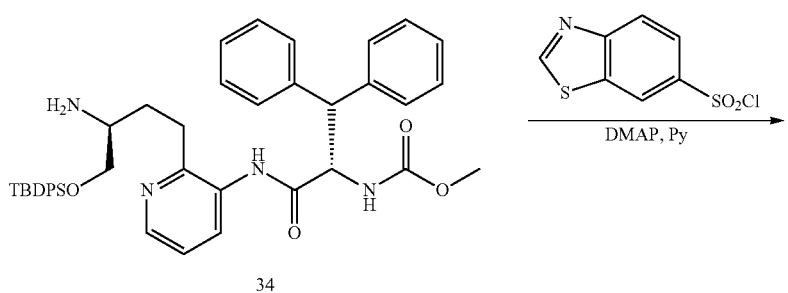

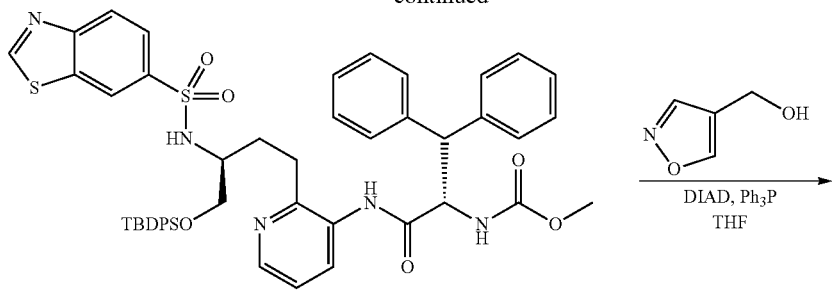

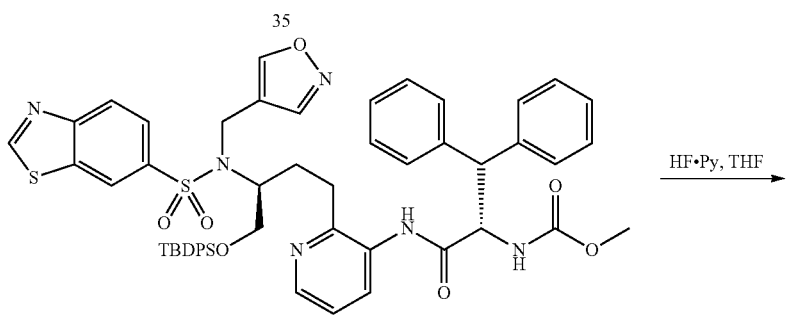

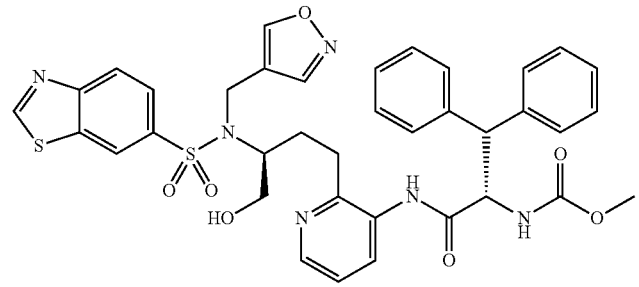

Example 18

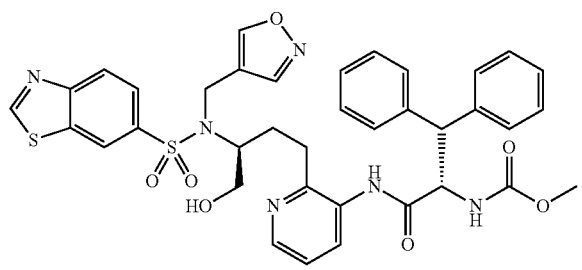 [SMILES: COC(=O)N[C@H](C(=O)Nc1cccnc1CC[C@@H](CO)N(Cc1cnoc1)S(=O)(=O)c1ccc2ncsc2c1)C(c1ccccc1)c1ccccc1]

N-(2-{(3S)-3-[(1,3-benzothiazol-6-ylsulfonyl)(isoxazol-4-ylmethyl)amino]-4-hydroxy butyl}pyridin-3-yl)-Nα-(methoxycarbonyl)-β-phenyl-L-phenylalaninamide (37)

Step 1: tert-butyl[(2S)-1-{[tert-butyl(diphenyl)silyl]oxy}but-3-yl]-2-yl]carbamate (30)

A solution of dimethyl(1-diazo-2-oxopropyl)phosphonate (29, 1.32 g, 6.9 mmol) in dry THF (15 ml) stirred at −78° C. under N₂ was treated with 25% solution of NaOMe in MeOH (1.7 mL, 7.4 mmol) and the mixture stirred at the same temperature for 14 min; then a solution of tert-butyl[(2R)-1-{[tert-butyl(diphenyl)silyl]oxy}-3-oxopropan-2-yl]carbamate (3, 1.51 g, 3.53 mmol) in DCM (15 mL+3 mL rinse) was slowly added with syringe over 5 min. After addition was completed, the solution was stirred at −78° C. for 12 min, the dry-ice bath removed and the system stirred at room temperature for 90 min. Diluted (DCM) washed with sat. NaHCO₃, dried over MgSO₄, filtered and concentrated. Purification made by passage through a cartridge of silicagel (40 g) eluted with 1.5% to 15% EtOAc in hexanes (UV detection at 254 nm) to afford title compound (955 mg, 64% yield) as a white solid. MS: m/z=446.2 (MNa+).

Dimethyl(1-diazo-2-oxopropyl)phosphonate (29)

A suspension of dimethyl(2-oxopropyl)phosphonate (2.1 g, 12.9 mmol) and potassium carbonate (2.2 g, 15.9 mmol) in dry MeCN (40 mL) was treated with slow addition of a solution of 4-dodecylbenzenesulfonyl azide (5.7 g, 16.2 mmol) in dry MeCN (90 mL) for over 30 min. After being stirred for 2.5 h under N₂ atmosphere at room temperature, the mixture was treated with saturated NH₄Cl (100 mL), poured into a separatory funnel and extracted with EtOAc (3×100 mL), dried over Na₂SO₄, filtered, solvent evaporated and the residue chromatographed in a cartridge of silicagel (40 g) eluted with 15% to 100% EtOAc in hexane (UV detection at 254 nm), to afford reagent 29 as a light yellow oil.

Step 2: tert-butyl[(2S)-4-(3-aminopyridin-2-yl)-1-{[tert-butyl(diphenyl)silyl]oxy}but-3-yn-2-yl]carbamate (31)

A mixture of tert-butyl[(2S)-1-{[tert-butyl(diphenyl)silyl]oxy}but-3-yn-2-yl]carbamate (30, 144 mg, 0.340 mmol), 2-bromopyridin-3-amine (53 mg, 0.306 mmol) (or any other suitable halide or triflate ester) and bis(triphenylphosphine)palladium(II) dichloride (18 mg, 0.026 mmol) was dissolved in degassed dry TEA (1.2 mL, 8.61 mmol) and acetonitrile (0.6 ml), stirred for 5 minutes at room temperature and treated with copper(I) iodide (7 mg, 0.037 mmol). The final mixture was placed in a preheated oil bath at +52° C. and further stirred under $N_2$ in the dark for 4.5 h, concentrated and submitted to purification through a chromatographic cartridge of silicagel (12 g) eluted with 0.5% to 12% MeOH in DCM (UV detection at 254 nm) to give title compound (157 mg, 99% yield) as a brown solid. MS: m/z=516.3 (MH+).

Step 3: tert-butyl[(2S)-4-(3-aminopyridin-2-yl)-1-{[tert-butyl(diphenyl)silyl]oxy}butan-2-yl]carbamate (32)

The title compound was prepared in 87% yield from intermediate 31 following the procedure described for the step 5 in scheme 1 corresponding to the synthesis of example 1, MS: m/z=520.3 (MH+).

Step 4: N-{2-[(3S)-3-[(tert-butoxycarbonyl)amino]-4-{[tert-butyl(diphenyl)silyl]oxy}butyl)pyridin-3-yl}-Nα-(methoxycarbonyl)-β-phenyl-L-phenylalaninamide (33)

The title compound was prepared in 100% yield from intermediate 32 following the procedure described for the step 6 in scheme 1 corresponding to the synthesis of example 1, MS: m/z=801.2 (MH+).

Step 5: N-{2-[(3S)-3-amino-4-{[tert-butyl(diphenyl)silyl]oxy}butyl]pyridin-3-yl}-Nα-(methoxycarbonyl)-β-phenyl-L-phenylalaninamide (34)

The title compound was prepared in 100% yield from intermediate 33 following the procedure described for the step 7 in scheme 1 corresponding to the synthesis of example 1, MS: m/z=701.3 (MH+).

Step 6: N-{2-[(3S)-3-[(1,3-benzothiazol-6-ylsulfonyl)amino]-4-{[tert-butyl(diphenyl)silyl]oxy}butyl]phenyl}-Nα-(methoxycarbonyl)-β-phenyl-L-phenylalaninamide (35)

The title compound was prepared in 58% yield from intermediate 34 following the procedure described for the step 8 in scheme I corresponding to the synthesis of example 1 but using 1,3-benzothiazole-6-sulfonyl chloride instead of 4-nitrobenzene sulfonyl chloride MS: m/z=898.3 (MH+).

Step 7: N-{2-[(3S)-3-[(1,3-benzothiazol-6-ylsulfonyl)(isoxazol-4-ylmethyl)amino]-4-{[tert-butyl(diphenyl)silyl]oxy}butyl]phenyl}-Nα-(methoxycarbonyl)-β-phenyl-L-phenylalaninamide (36)

The title compound was prepared in 99% yield from intermediate 35 following the procedure described for the step 9 in scheme 1 corresponding to the synthesis of example 1 but using isoxazol-4-ylmethanol instead isoamyl alcohol. MS: m/z=979.3 (MH+).

Step 8: N-(2-{(3S)-3-[(1,3-benzothiazol-6-ylsulfonyl)(isoxazol-4-ylmethyl)amino]-4-hydroxybutyl}pyridin-3-yl)-Nα-(methoxycarbonyl)-β-phenyl-L-phenylalaninamide (37)

The title compound was prepared in 48% yield from intermediate 36 following the procedure described for the step 10 in scheme 1 corresponding to the synthesis of example 1. MS: m/z=741.1 (MH+).

H-NMR (400 MHz, CH₃CN-d3), δ: 9.32 (1 H, s), 8.64 (1 H, s), 8.56 (1 H, s), 8.45 (1 H, s), 8.23-8.12 (3 H, m), 7.91 (1 H, d, J=8.72 Hz), 7.61-7.13 (10 H, m), 7.10-6.99 (2 H, m), 6.13 (1 H, d, J=8.67 Hz), 5.12 (1 H, t, J=8.72 Hz), 4.52-4.42 (3 H, m), 4.36 (1 H, m), 4.00-3.87 (1 H, m), 3.58 (3 H, 3.56-3.50 (4 H, m), 2.01-1.85 (1 H, m), 1.73-1.62 (1 H, m).

TABLE 2

Examples made following synthetic procedures analogous to those described for example 18

| Example number | Compound number | Structure | Characterization data MS : m/z |
|---|---|---|---|
| 19 | 38 | N-[2[(3S)-3-{(1,3-benzothiazol-6-ylsulfonyl)[(4-methylpyrimidin-5-yl)methyl]amino)-4-hydroxybutyl]pyridin-3-yl]-Nα-(methoxycarbonyl)-β-phenyl-L-phenylalaninamide | 766.2 (MH+) |

TABLE 2-continued

Examples made following synthetic procedures analogous to those described for example 18

| Example number | Compound number | Structure | Characterization data MS : m/z |
|---|---|---|---|
| 20 | 39 | N-{4-[(3S)-3-{(1,3-benzothiazol-6-ylsulfonyl)[(4-methylpyrimidin-5-yl)methyl]amino}-4-hydroxybutyl]pyridin-3-yl}-Nα-(methoxycarbonyl)-β-phenyl-L-phenylalaninamide | 766.3 (MH+) |
| 21 | 40 | N-(2-{(3S)-3-[(1,3-benzothiazol-6-ylsulfonyl)(2-methylpropyl)amino]-1-d2-2-d2-4-hydroxybutyl}phenyl)-Nα-(methoxycarbonyl)-β-phenyl-L-phenylalaninamide | 719.2 (MH+) |
| 22 | 41 | N-(2-{(3S)-3-[(1,3-benzothiazol-6-ylsulfonyl)(2-methylpropyl-d7)amino]-1-d2-2-d2-4-hydroxybutyl}phenyl)-Nα-(methoxycarbonyl)-β-phenyl-L-phenylalaninamide | 728.3 (MH+) |

Compounds of the present invention can also be prepared according to Scheme 3, as indicated below. Thus the carboxylic acid group of a suitable N-protected L-cystein can be reduced to an alcohol. The resulting mercapto alcohol can then be used as a nucleophile for regioselective S-arylation using an activated aryl group, such as an ortho-nitro-aryl halide suitably fuctionalized. The free alcohol can be then protected using a silyl ester and the following reduction of the nitro group can be made by treatment with SnCl₂ or iron. The resulting free amine can be subjected to the sequence of reactions described in scheme 1 (starting with coupling to a carboxylic acid using different coupling agents such as PyBOP, HBTU or HATU) to provide the compounds of the invention.

Scheme 3
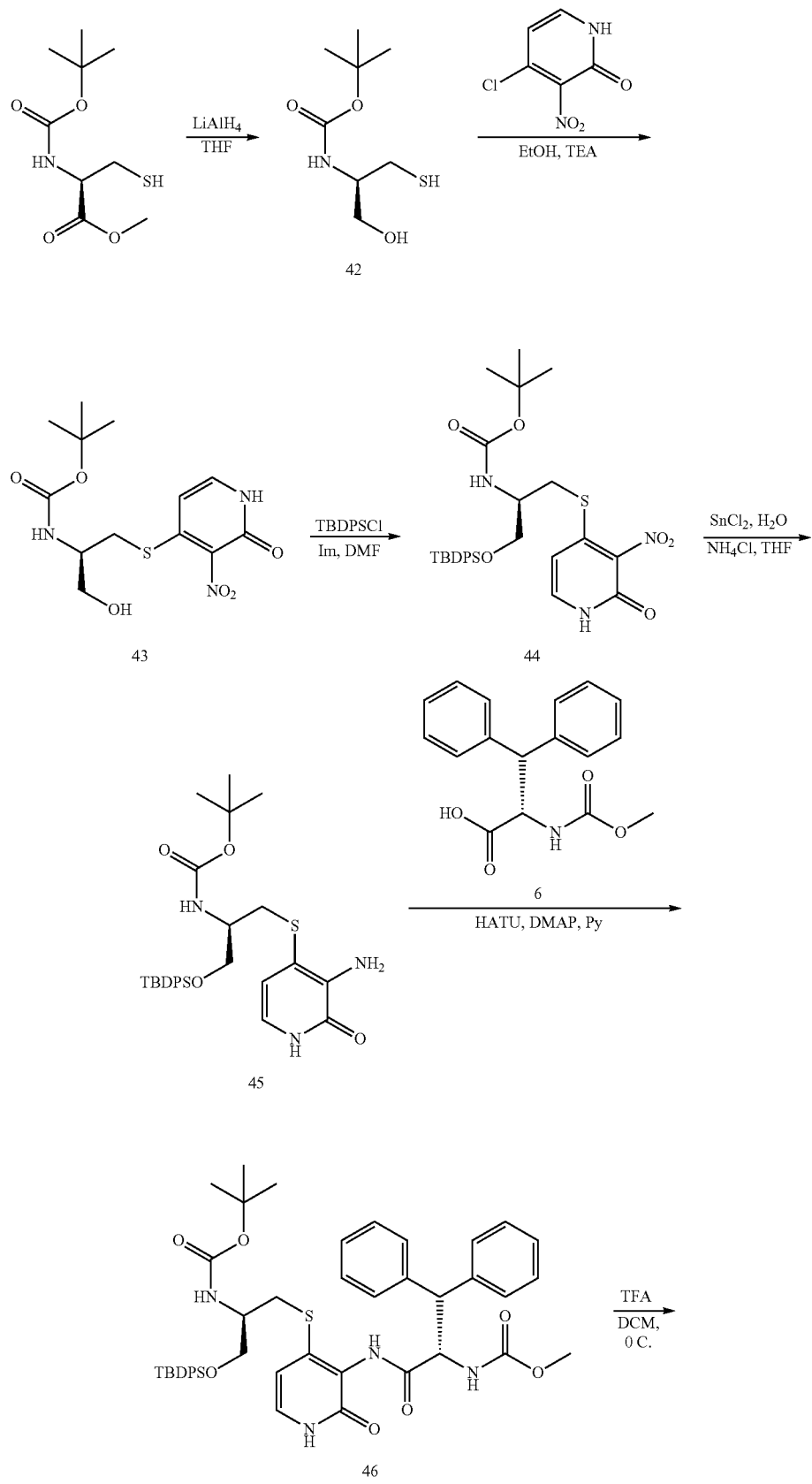

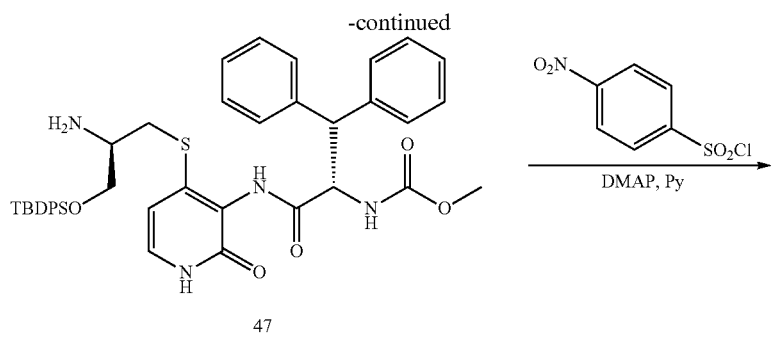
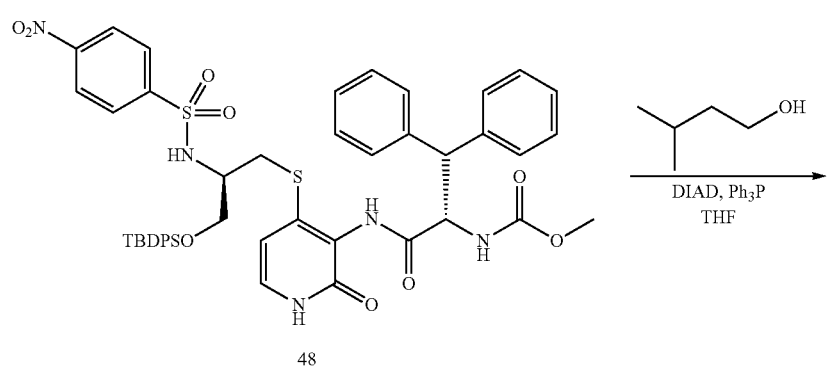
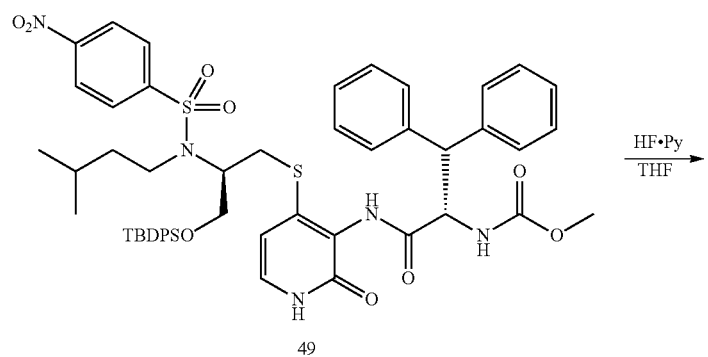
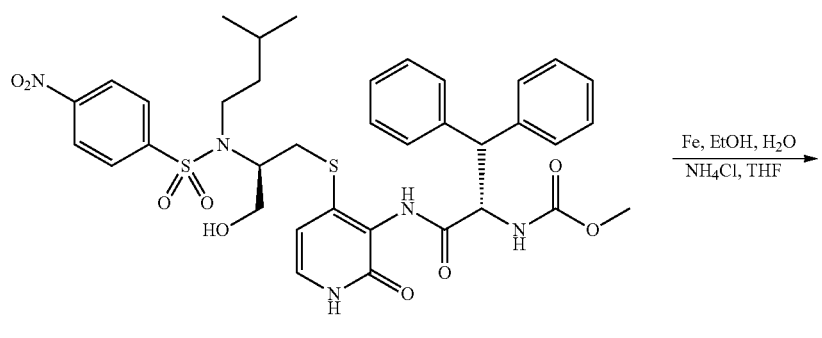

-continued

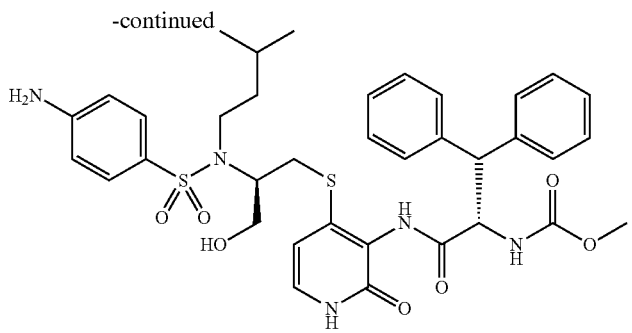

51

Example 23

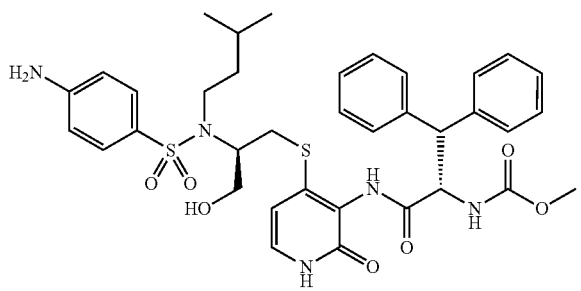 [SMILES: COC(=O)N[C@H](C(=O)Nc1c(SC[C@@H](CO)N(CCC(C)C)S(=O)(=O)c2ccc(N)cc2)cc[nH]c1=O)C(c1ccccc1)c1ccccc1]

N-(4-{[(2R)-2-{[(4-aminophenyl)sulfonyl](3-methylbutyl)amino}-3-hydroxypropyl]sulfanyl}-2-oxo-1,2-dihydropyridin-3-yl)-Nα-(methoxycarbonyl)-β-phenyl-L-phenyl alaninamide (51)

Step 1: tert-butyl[(2R)-1-hydroxy-3-sulfanylpropan-2-yl]carbamate (42)

A solution of methyl N-(tert-butoxycarbonyl)-L-cysteinate (2.6 g, 11.0 mmol) in THF (10 ml) stirred at 0° C. under $N_2$ was treated with slow addition of a 1M solution of $LiAlH_4$ in THF (20 mL, 20 mmol). The reaction mixture was slowly warmed up to room temperature and further stirred for 2 h, cooled to 0° C. and quenched with slow addition of water, then poured on a 15% solution of $K_2CO_3$ in water (25 mL), shaken well and extracted with DCM (3×100 mL), the organic layers were combined and dried over $MgSO_4$, filtered and concentrated to afford the title compound as colorless oil, kept under $N_2$ atmosphere all the times and used fresh without further purification. Assumed quantitative yield. MS: m/z=230.1 (MNa+).

Step 2: tert-butyl{(2R)-1-hydroxy-3-[(3-nitro-2-oxo-1,2-dihydropyridin-4-yl)sulfanyl]propan-2-yl}carbamate (43)

A solution of 4-chloro-3-nitropyridin-2(1H)-one (1.61 g, 9.2 mmol) (or any other suitable activated aromatic compound) and TEA (2 ml, 14.4 mmol) in ethanol (15 mL) stirred at 0° C., was treated with a solution of tert-butyl[(2R)-1-hydroxy-3-sulfanylpropan-2-yl]carbamate (42, 2.073 g, 10 mmol) in ethanol (10 mL+5 ml rinse) added from syringe. The final mixture was stirred at room temperature for 22 h (became a thick yellow suspension). Filtered, the cake washed with pentane and dried under vacuum, to afford the title compound (2.20 g, 69% yield) as a yellow solid, MS: m/z=368.1 (MNa+).

Step 3: tert-butyl {(2R)-1-{[tert-butyl(diphenyl)silyl]oxy}-3-[(3-nitro-2-oxo-1,2-dihydropyridin-4-yl)sulfanyl]propan-2-yl}carbamate (44)

The title compound was prepared in 88% yield from intermediate 43 following the procedure described for the step 2 in scheme 1 corresponding to the synthesis of example 1. MS: m/z=606.2 (MNa+).

Step 4: tert-butyl[(2R)-1-[(3-amino-2-oxo-1,2-dihydropyridin-4-yl)sulfanyl]-3-{[tert-butyl(diphenyl)silyl]oxy)propan-2-yl]carbamate (45)

A solution of tert-butyl{(2R)-1-{[tert-butyl(diphenyl)silyl]oxy}-3-[(3-nitro-2-oxo-1,2-dihydropyridin-4-yl)sulfanyl]propan-2-yl}carbamate (44, 507 mg, 0.87 mmol) and ammonium acetate (1.1 g, 14.0 mmol) in THF (12 ml) and water (3 ml) was treated with anhydrous tin(II) chloride (1.04 g, 5.5 mmol) and the mixture stirred at +65° C. for 22 h. The reaction mixture was diluted with DCM, washed with saturated $NaHCO_3$, dried over $MgSO_4$, filtered and concentrated. Purification was performed in a chromatographic column on silicagel, eluted with 30% to 100% EtOAc in hexane to afford title compound (303 mg, 63% yield) as a light green solid. MS: m/z=576.2 (MNa+).

Step 5: N-(4-{[(2R)-2-[(tert-butoxycarbonyl)amino]-3-{tert-butyl(diphenyl)silyl]oxy}propyl]sulfanyl}-2-oxo-1,2-dihydropyridin-3-yl)-Nα-(methoxycarbonyl)-β-phenyl-L-phenylalaninamide (46)

The title compound was prepared in 100% yield from intermediate 45 following the procedure described for the step 6 in scheme 1 corresponding to the synthesis of example 1. MS: m/z=835.2 (MH+)

Step 6: N-(4-{[(2R)-2-amino-3-{[tert-butyl(diphenyl)silyl]oxy}propyl]sulfanyl}-2-oxo-1,2-dihydropyridin-3-yl)-Nα-(methoxycarbonyl)-β-phenyl-L-phenylalaninamide (47)

The title compound was prepared in 86% yield from intermediate 46 following the procedure described for the step 7 in scheme 1 corresponding to the synthesis of example 1. MS: m/z=735.3 (MH+).

Step 7: N-(4-{[(2R)-3-{[tert-butyl(diphenyl)silyl]oxy}-2-{[(4-nitrophenyl)sulfonyl]amino}propyl]sulfanyl}-2-oxo-1,2-dihydropyridin-3-yl)-Nα-(methoxycarbonyl)-β-phenyl-L-phenylalaninamide (48)

The title compound was prepared in 100% yield from intermediate 47 following the procedure described for the step 8 in scheme 1 corresponding to the synthesis of example 1. MS: m/z=920.05 (MH+).

Step 8: N-(4-{[(2R)-3-{[tert-butyl(diphenyl)silyl]oxy}-2-{(3-methylbutyl)[(4-nitro phenyl)sulfonyl]amino}propyl]sulfanyl}-2-oxo-1,2-dihydropyridin-3-yl)-Nα-(methoxycarbonyl)-β-phenyl-L-phenylalaninamide (49)

The title compound was prepared in 50% yield from intermediate 48 following the procedure described for the step 9 in scheme 1 corresponding to the synthesis of example 1. MS: m/z=990.25 (MH+).

Step 9: N-(4-{[(2R)-3-hydroxy-2-{(3-methylbutyl)[(4-nitrophenyl)sulfonyl]amino}propyl]sulfanyl}-2-oxo-1,2-dihydropyridin-3-yl)-Nα-(methoxycarbonyl)-β-phenyl-L-phenylalaninamide (50)

The title compound-was prepared in 30% yield from intermediate 49 following the procedure described for the step 10 in scheme 1 corresponding to the synthesis of example 1. MS: m/z=752.2 (MH+).

Step 10: N-(4-{[(2R)-2-{[(4-aminophenyl)sulfonyl](3-methylbutyl)amino}-3-hydroxypropyl]sulfanyl}-2-oxo-1,2-dihydropyridin-3-yl)-Nα-(methoxycarbonyl)-β-phenyl-L-phenylalaninamide (51)

A solution of N-(4-{[(2R)-3-hydroxy-2-{(3-methylbutyl)[(4-nitrophenyl)sulfonyl]amino}propyl]sulfanyl}-2-oxo-1,2-dihydropyridin-3-yl)-Nα-(methoxycarbonyl)-β-phenyl-L-phenylalaninamide (50, 61.3 mg, 0.082 mmol) in ethanol (3 ml), THF (1.5 ml) and water (0.8 mL) was treated with saturated solution of ammonium chloride (298 mg, 5.57 mmol) in water (0.8 mL) followed by addition of powdered iron (80 mg, 1.433 mmol). The mixture was degassed and stirred under $N_2$ at external temperature of 74° C. for 90 min. Diluted with DCM, washed with saturated $NaHCO_3$, dried over $MgSO_4$, filtered and concentrated. Purification performed in a column of silicagel eluted with 5% to 35% MeOH in DCM to afford the title compound (27 mg, 45% yield) as pale yellow foam. MS: m/z=722.2 (MH+).

H-NMR (400 MHz, DMSO-d6), δ: 11.56 (1 H, s), 9.12 (1 H, d, J=13.86 Hz), 7.52-7.31 (6H, m), 7.23-7.05 (8 H, m), 6.61 (2 H, d, J=8.33 Hz), 6.09 (1 H, d, J=7.11 Hz), 5.97 (2 H, s), 5.19 (1 H, t, J=10.00 Hz), 4.83 (1 H, d, J=5.21 Hz), 4.42 (1 H, d, J=10.82 Hz), 3.60 (1 H, s), 3.42 (3 H, s), 3.01-2,88 (2 H, m), 2.91 (1 H, t, J=8.7 Hz), 2.77-2.65 (1H, m) 1.50-1.37 (3 H, m), 1.24 (2 H, s), 0.85 (6 H, d, J=6.15 Hz)

TABLE 3

Examples made following synthetic procedures analogous to those described for example 23

| Example number | Compound number | Structure | Characterization data MS : m/z |
|---|---|---|---|
| 24 | 52 | N-[4-({(2R)-2-[(1,3-benzothiazol-6-ylsulfonyl)(2-methylpropyl)amino]-3-hydroxypropyl}sulfanyl)pyridin-3-yl]-Nα-(methoxycarbonyl)-β-phenyl-L-phenylalaninamide | 734.2 (MH+) |
| 25 | 53 | N-[4-({(2R)-2-[(1,3-benzothiazol-6-ylsulfonyl)(2-methylpropyl d7)amino)-3-hydroxypropyl}sulfanyl)pyridin-3-yl]-Nα-(methoxycarbonyl)-β-phenyl-L-phenylalaninamide | 743.2 (MH+) |

TABLE 3-continued

Examples made following synthetic procedures analogous to those described for example 23

| Example number | Compound number | Structure | Characterization data MS : m/z |
|---|---|---|---|
| 26 | 54 | N-(4-{[(2R)-2-{(1,3-benzothiazol-6-ylsulfonyl)[(1,3-dimethyl-1H-pyrazol-4-yl)methyl]amino}-3-hydroxypropyl)sulfanyl}pyridin-3-yl)-Nα-(methoxycarbonyl)-β-phenyl-L-phenylalaninamide | 786.1 (MH+) |
| 27 | 55 | N-[4-({(2R)-2-[(1,3-benzothiazol-6-ylsulfonyl)(isoxazol-4-ylmethyl)amino]-3-hydroxypropyl}sulfanyl)pyridin-3-yl]-Nα-(methoxycarbonyl)-β-phenyl-L-phenylalaninamide | 759.1 (MH+) |

Compounds of the present invention can also be prepared according to Scheme 4, as indicated below. Thus the primary alcohol of a suitable substituted L-serine derivative can be converted into an appropriate leaving group, such as a chloride. The resulting chloride can then be used as electrophile for S-alkylation using a thiol, such as an 2-aminobenzenethiol. The resulting aniline can be subjected to the sequence of reactions described in scheme 1 (starting with coupling to a carboxylic acid using different coupling agents such as PyBOP, HBTU or HATU) to provide the compounds of the invention.

Scheme 4

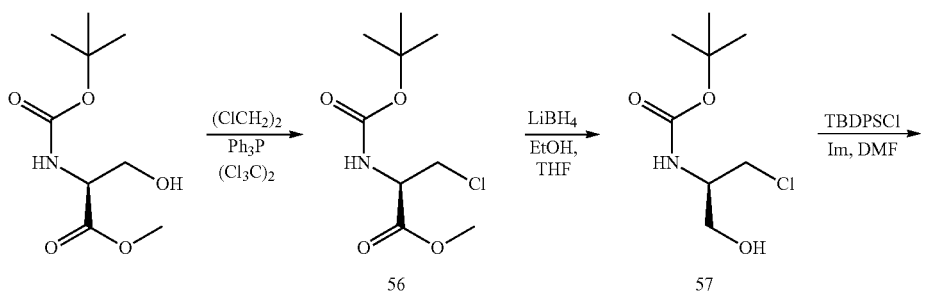

-continued
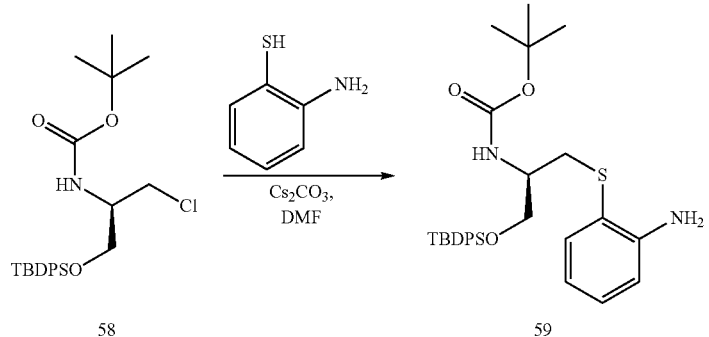
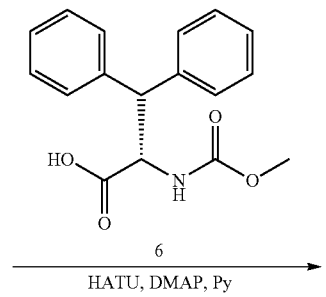
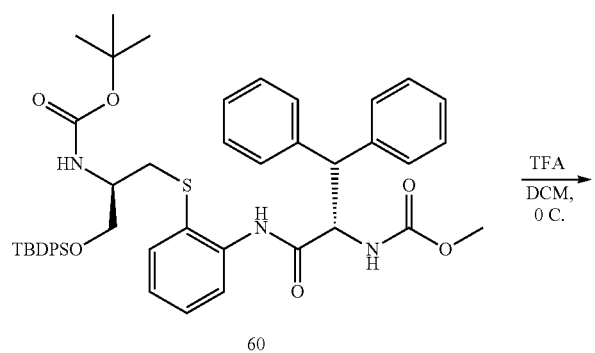
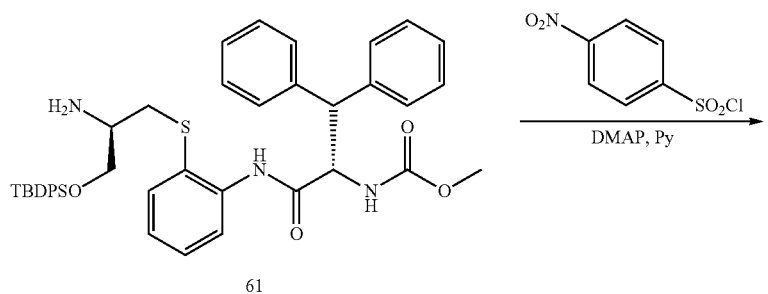
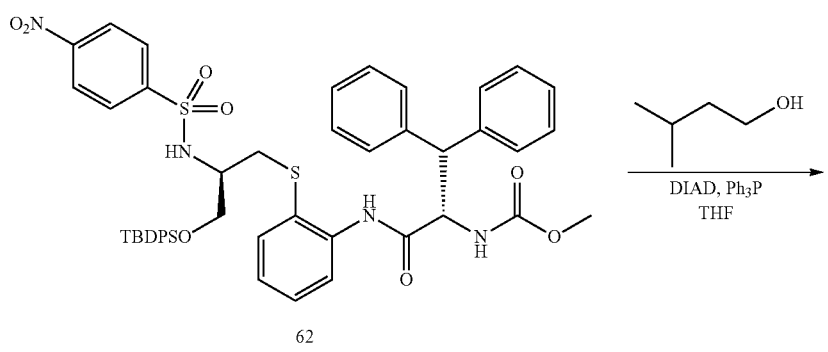

-continued
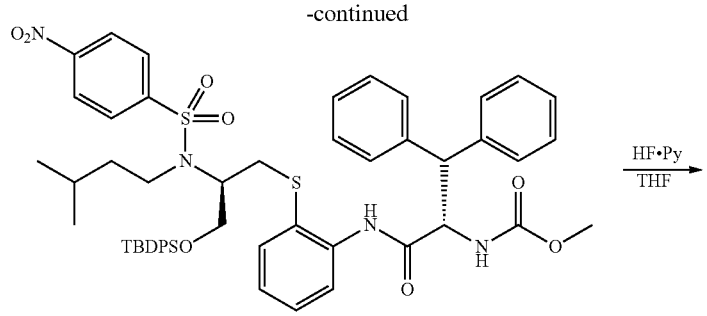
63
HF·Py
THF →
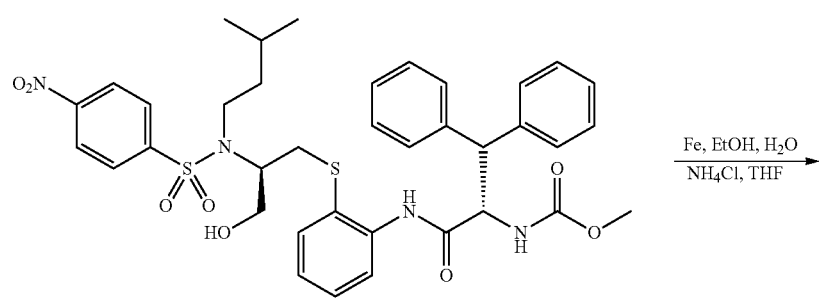
64
Fe, EtOH, H₂O
NH₄Cl, THF →
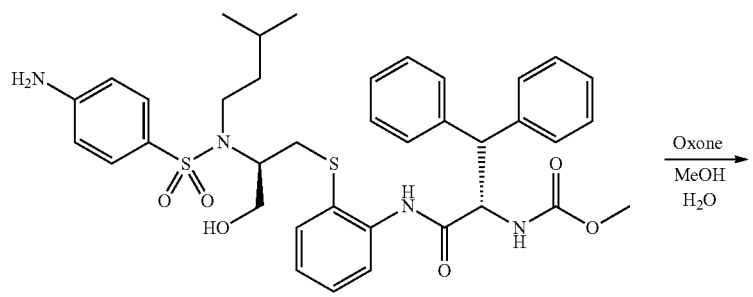
65
Oxone
MeOH
H₂O →
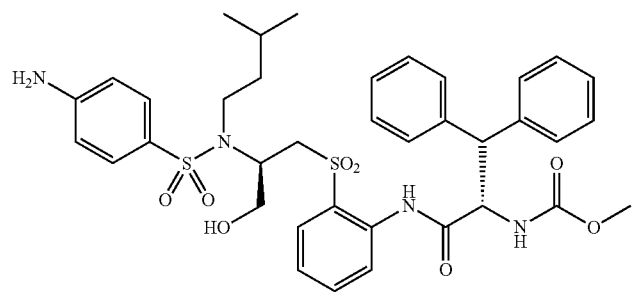
66

Example 28

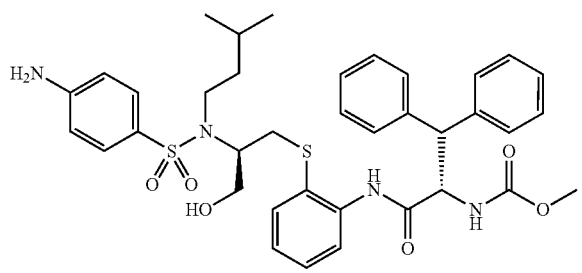 [SMILES: COC(=O)N[C@H](C(=O)Nc1ccccc1SC[C@@H](CO)N(CCC(C)C)S(=O)(=O)c1ccc(N)cc1)C(c1ccccc1)c1ccccc1]

N-(2-{[(2R)-2-{[(4-aminophenyl)sulfonyl](3-methylbutyl)amino}-3-hydroxypropyl]sulfanyl}phenyl)-Nα-(methoxycarbonyl)-β-phenyl-L-phenylalaninamide (65)

Step 1: methyl N-(tert-butoxycarbonyl)-3-chloro-L-alaninate (56)

A solution of triphenylphosphine (4.55 g, 17.4 mmol) and hexachloroethane (3.9 g, 16.5 mmol) in 1,2-dichloroethane (18 mL) prepared at 0° C. was added via cannula into a flask containing a solution of methyl N-(tert-butoxycarbonyl)-L-serinate (3.2 g, 14.6 mmol) in 1,2-dichloroethane DCE (40 mL), kept at 0° C. under $N_2$ atmosphere. After the addition was completed, the reaction mixture was further stirred at room temperature for 2 h, diluted with DCM, washed with sat NaHCO$_3$, dried over MgSO$_4$, filtered and concentrated. Purification made through chromatographic column of silicagel eluted with 10% to 50% EtOAc in hexane for 30 min, to afford 2.13 g (61% yield) of title compound as white crystals. MS: m/z=260.0 (MNa+).

Step 2: tert-butyl[(2R)-1-chloro-3-hydroxypropan-2-yl]carbamate (57)

A solution of methyl N-(tert-butoxycarbonyl)-3-chloro-L-alaninate (56, 2.13 g, 9.0 mmol) in ethanol (41 ml) stirred at 0° C. under $N_2$ atmosphere was treated with a 2M solution of LiBH$_4$ in THF (5 mL, 10 mmol) (slow addition). The reaction mixture was slowly warmed up to room temperature and further stirred for 4 h, cooled to 0° C., treated with saturated NaHCO$_3$ (5 mL) followed by acetone (5 mL), stirred for 10 minutes, diluted with DCM and washed with brine, dried over MgSO$_4$ filtered and concentrated to afford 1.94 (100% yield) of title compound as a white solid. MS: m/z=232.0 (MNa+).

Step 3: tert-butyl[(2R)-1-{[tert-butyl(diphenyl)silyl]oxy}-3-chloropropan-2-yl]carbamate (58)

The title compound was prepared in 92% yield from intermediate 57 following the procedure described for the step 2 in scheme 1 corresponding to the synthesis of example 1. MS: m/z=470.2 (MNa+).

Step 4: tert-butyl[(2R)-1-[(2-aminophenyl)sulfanyl]-3-{[tert-butyl(diphenyl)silyl]oxy}propan-2-yl]carbamate (59)

A solution of tert-butyl[(2R)-1-{[tert-butyl(diphenyl)silyl]oxy}-3-chloropropan-2-yl]carbamate (58, 390 mg, 0.87 mmol) in dry DMF (2.5 ml) was treated with neat 2-aminobenzenethiol (351 mg, 2.8 mmol) followed by cesium carbonate (560 mg, 1.72 mmol). The mixture was stirred at room temperature for 3 h, diluted with DCM and washed with 1M NaOH followed by saturated NaHCO$_3$, dried over MgSO$_4$, filtered and concentrated to afford the title compound (482 mg) as an oil, which was submitted without further purification to the next synthetic step. MS: m/z=537.2 (MH+).

Step 5: methyl{(2S)-1-[(2-{[(2R)-2-[(tert-butoxycarbonyl)amino]-3-{[tert-butyl(diphenyl)silyl]oxy}propyl]sulfanyl}phenyl)amino]-1-oxo-3,3-diphenylpropan-2-yl}carbamate (60)

The title compound was prepared in 79% yield from intermediate 59 following the procedure described for the step 6 in scheme 1 corresponding to the synthesis of example 1. MS: m/z=840.2 (MNa+).

Step 6: N-(2-{[(2R)-2-amino-3-{[tert-butyl(diphenyl)silyl]oxy}propyl]sulfanyl}phenyl)-Nα-methoxycarbonyl)-β-phenyl-L-phenylalaninamide (61)

The title compound was prepared in 97% yield from intermediate 60 following the procedure described for the step 7 in scheme 1 corresponding to the synthesis of example 1. MS: m/z=718.3 (MH+).

Step 7: N-(2-{[(2R)-3-{[tert-butyl(diphenyl)silyl]oxy}-2-{[(4-nitrophenyl)sulfonyl]amino}propyl]sulfanyl}phenyl)-Nα-(methoxycarbonyl)-β-phenyl-L-phenyl alaninamide (62)

The title compound was prepared in quantitative yield from intermediate 61 following the procedure described for the step 8 in scheme 1 corresponding to the synthesis of example 1. MS: m/z=903.10 (MH+).

Step 8: N-(2-{[(2R)-3-{[tert-butyl(diphenyl)silyl]oxy}-2-{(3-methylbutyl)[(4-nitro phenyl)sulfonyl]amino}propyl]sulfanyl}phenyl)-Nα-(methoxycarbonyl)-β-phenyl-L-phenylalaninamide (63)

The title compound was prepared in 45% yield from intermediate 62 following the procedure described for the step 9 in scheme 1 corresponding to the synthesis of example 1. MS: m/z=9952 (MNa+).

Step 9: N-(2-{[(2R)-3-hydroxy-2-[(3-methylbutyl)[(4-nitrophenyl)sulfonyl]amino}propyl]sulfanyl}phenyl)-Nα-(methoxycarbonyl)-β-phenyl-L-phenylalaninamide (64)

The title compound was prepared in 42% yield from intermediate 63 following the procedure described for the step 10 in scheme 1 corresponding to the synthesis of example 1. MS: m/z=735.25 (MH+).

Step 10: Example 28. N-(2-{[(2R)-2-{[(4-aminophenyl)sulfonyl](3-methylbutyl)amino}-3-hydroxy propyl]sulfanyl}phenyl)-Nα-(methoxycarbonyl)-β-phenyl-L-phenylalaninamide (65)

The title compound was prepared in 99% yield from intermediate 64 following the procedure described for the step 10 in scheme 3 corresponding to the synthesis of example 23. MS: m/z=705.3 (MH+).

¹H-NMR (400 MHz, DMSO-d6), δ: 9.36 (1 H, s), 7.65 (1 H, d, J=8.81 Hz), 7.43 (4 H, m), 7.38-7.06 (12 H, m), 6.59 (2 H, d, J=8.27 Hz), 5.96 (2 H, s), 5.25 (1 H, t, J=10.09 Hz), 4.84 (1 H, s), 4.44-4.32 (2 H, m), 3.75 (1 H, s), 3.46 (4 H, s), 3.07 (3 H, m), 3.02 (1 H, s), 1.55-1.36 (3 H, m), 1.36-1.15 (3 H, m), 0.83 (6 H, t, J=6.10 Hz).

Step 11: Example 29. N-(2-{[(2R)-2-{[(4-aminophenyl)sulfonyl](3-methylbutyl)amino}-3-hydroxy propyl]sulfonyl}phenyl)-Nα-(methoxycarbonyl)-β-phenyl-L-phenyl alaninamide (66)

A solution of N-(2-{[(2R)-2-{[(4-aminophenyl)sulfonyl](3-methylbutyl)amino}-3-hydroxy propyl]sulfanyl}phenyl)-Nα-(methoxycarbonyl)-β-phenyl-L-phenylalaninamide (65, 7.5 mg, 10.6 μmol) in MeOH (2 mL), stirred at 0° C., was treated with a solution of oxone (19.7 mg, 32 μmol) in water (0.3 mL) and the final mixture stirred at 0° C. for 45 min, diluted with DCM (60 mL) and washed with saturated NaHCO₃, dried over MgSO₄, filtered and concentrated to afford 5.8 mg (76% yield) of the title compound. MS: m/z=737.2 MH+).

H-NMR (400 MHz, DMSO-d6): δ: 9.69 (1 H, s), 7.80 (2 H, t, J=7.46 Hz), 7.66-7.52 (2 H, m), 7.43-7.08 (11 H, m), 6.59 (2 H, d, J=8.36 Hz), 6.01 (2 H, s), 5.05 (1 H, t, J=10.09 Hz), 4.96 (1 H, s), 4.47 (1 H, d, J=11.30 Hz), 4.15 (1 H, t, J=6.81 Hz), 3.65-43.52 (1 H, m), 3.47 (3 H, s), 3.25-3.10 (1 H, m), 2.95-2.76 (2 H, m), 1.40-1.28 (2 H, m), 1.28-1.12 (4H, m), 1.10-1.02 (1 H, m), 0.76 (6 H, d, J=6.62 Hz).

TABLE 4

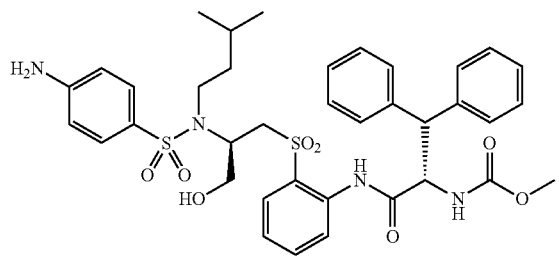 [SMILES: COC(=O)N[C@H](C(=O)Nc1ccccc1S(=O)(=O)C[C@@H](CO)N(CCC(C)C)S(=O)(=O)c1ccc(N)cc1)C(c1ccccc1)c1ccccc1]

Example 29

Examples made following synthetic procedures analogous to those described for example 28

| Example number | Compound number | Structure | Characterization data MS : m/z |
|---|---|---|---|
| 29 | 66 | N-(2-{[(2R)-2-{[(4-aminophenyl)sulfonyl](3-methylbutyl) amino}-3-hydroxy propyl]sulfonyl}phenyl)-Nα-(methoxycarbonyl)-β-phenyl-L-phenyl alaninamide | 737.20 (MH+) |
| 30 | 67 | N-(2-{[(2R)-2-{[(4-aminophenyl)sulfonyl](3-methylbutyl) amino}-3-hydroxy propyl]sulfinyl}phenyl)-Nα-(methoxycarbonyl)-β-phenyl-L-phenyl alaninamide | 721.2 (MH+) |

Compounds of the present invention can also be prepared according to Scheme 5, as indicated below. Thus the carboxylic acid group of a suitable N-protected (S)-2-amino-3-(3-nitrophenyl)propanoic acid can be reduced to an alcohol. The resulting free alcohol can be then protected using a silyl ester and the nitro group can be then hydrogenated in the presence of a palladium catalyst and hydrogen or by treatment with $SnCl_2$ or iron. The resulting free amine can be subjected to the sequence of reactions described in scheme 1 (starting with coupling to a carboxylic acid using different coupling agents such as PyBOP, HBTU or HATU) to provide the compounds of the invention.

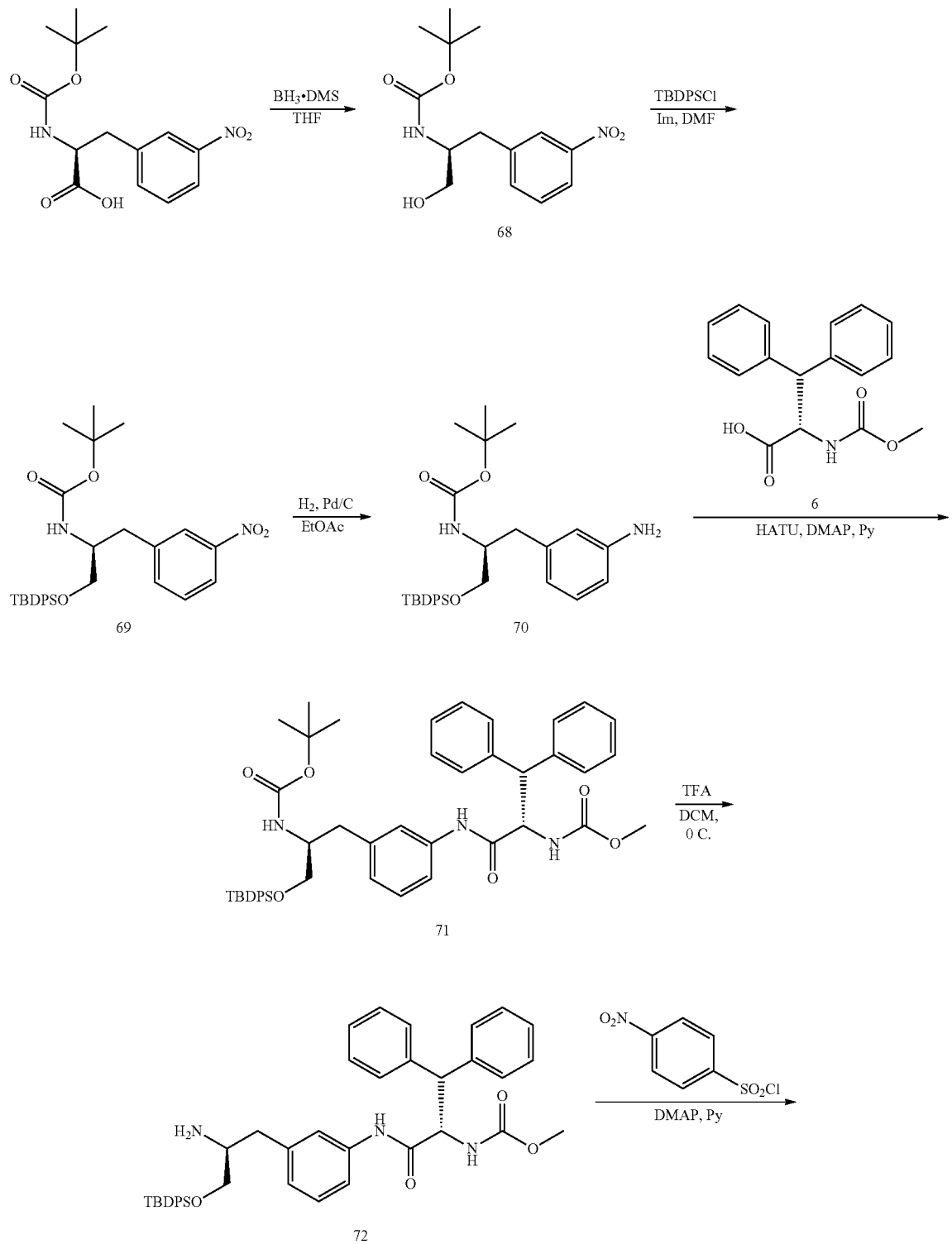

Scheme 5

-continued

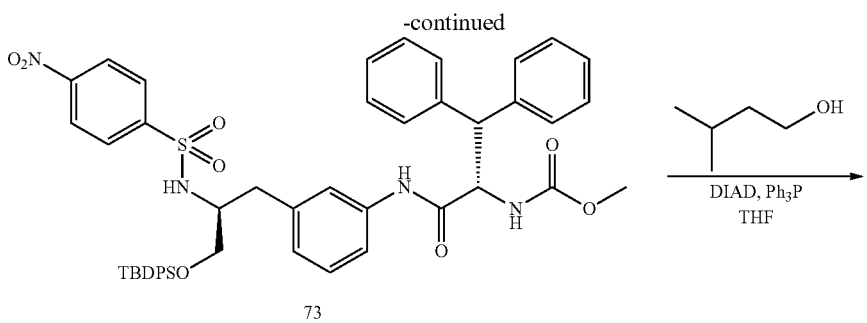

73

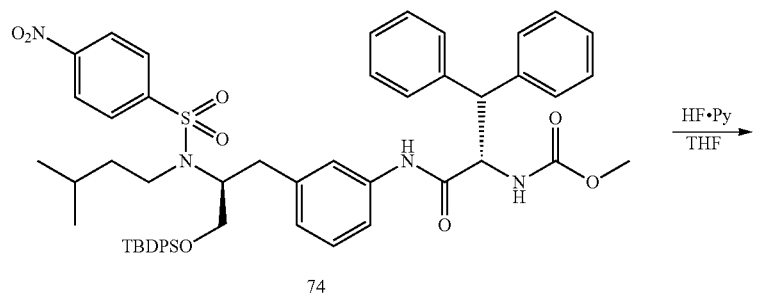

74

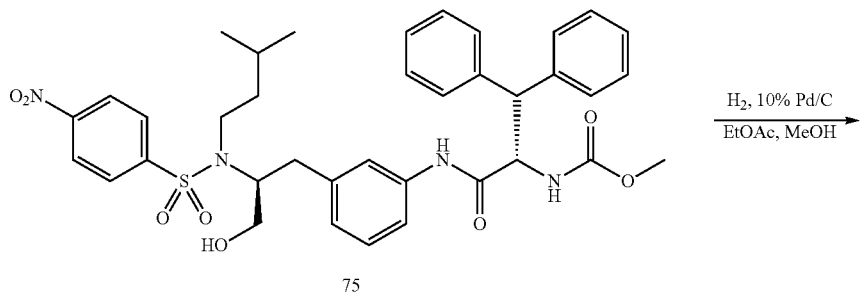

75

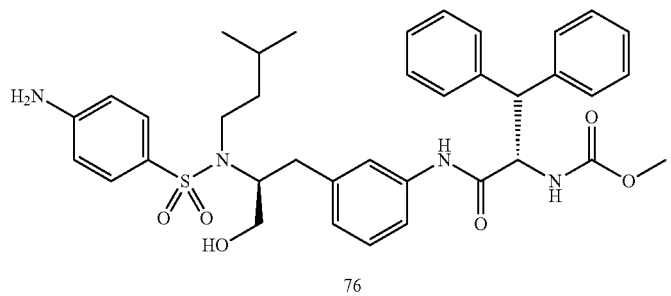

76

Example 31

N-{3-[(2S)-2-{[(4-aminophenyl)sulfonyl](3-methyl-butyl)amino}-3-hydroxypropyl]phenyl}-Nα-(methoxycarbonyl)-β-phenyl-L-phenylalaninamide (76)

Step 1: tert-butyl[(2S)-1-hydroxy-3-(3-nitrophenyl)propan-2-yl]carbamate (68)

To a solution of (S)-2-(tert-butoxycarbonylamino)-3-(3-nitrophenyl)propanoic acid (562 mg, 1.8 mmol) in THF (9 ml) stirred at 0° C. under $N_2$ atmosphere, 10 M solution of $BH_3$·DMS (0.5 ml, 5.27 mmol) was slowly added, after addition was completed the final mixture was warmed to room temperature and stirred for further 6 h. Cooled down to 0° C., quenched with water, diluted with DCM and washed with

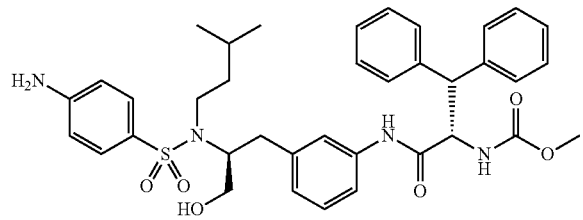 [SMILES: COC(=O)N[C@H](C(=O)Nc1cccc(C[C@@H](CO)N(CCC(C)C)S(=O)(=O)c2ccc(N)cc2)c1)C(c1ccccc1)c1ccccc1]

10% K₂CO₃ solution in water; dried over MgSO₄, filtered and concentrated to afford 432 mg (80% yield) of an oil which was submitted to the next step without further purification. MS: m/z=319.1 (MH+)

Step 2: tert-butyl[(2S)-1-{[tert-butyl(diphenyl)silyl]oxy}-3-(3-nitrophenyl)propan-2-yl]carbamate (69)

The title compound was prepared in 68% yield from intermediate 68 following the procedure described for the step 2 in scheme 1 corresponding to the synthesis of example 1. MS: m/z=557.2 (MNa+).

Step 3: tert-butyl[(2S)-1-(3-aminophenyl)-3-{[tert-butyl(diphenyl)silyl]oxy}propan-2-yl]carbamate (70)

The title compound was prepared in quantitative yield from intermediate 69 following the procedure described for the step 5 in scheme 1 corresponding to the synthesis of example 1. MS: m/z=5283 (MNa+).

Step 4: methyl[(2S)-1-({3-[(2S)-2-[(tert-butoxycarbonyl)amino]-3-{[tert-butyl(diphenyl)silyl]oxy}propyl]phenyl}amino)-1-oxo-3,3-diphenylpropan-2-yl]carbamate (71)

The title compound was prepared in quantitative yield from intermediate 70 following the procedure described for the step 6 in scheme 1 corresponding to the synthesis of example 1. MS: m/z=686.3 ((M-BOC)H+).

Step 5: N-{3-[(2S)-2-amino-3-{[tert-butyl(diphenyl)silyl]oxy}propyl]phenyl}-Nα-(methoxycarbonyl)-β-phenyl-L-phenylalaninamide (72)

The title compound was prepared in quantitative yield from intermediate 71 following the procedure described for the step 7 in scheme 1 corresponding to the synthesis of example 1. MS: m/z=686.3 (MH+).

Step 6: N-{3-[(2S)-3-{[tert-butyl(diphenyl)silyl]oxy}-2-{[(4-nitrophenyl)sulfonyl]amino)propyl]phenyl}-Nα-(methoxycarbonyl)-β-phenyl-L-phenylalaninamide (73)

The title compound was prepared in 51% yield from intermediate 72 following the procedure described for the step 8 in scheme 1 corresponding to the synthesis of example 1. MS: m/z=871.15 (MH+).

Step 7: N-{3-[(2S)-3-{[tert-butyl(dimethyl)silyl]oxy}-2-{(3-methylbutyl)[(4-nitrophenyl)sulfonyl]amino}propyl]phenyl}-Nα-(methoxycarbonyl)-β-phenyl-L-phenylalaninamide (74)

The title compound was prepared in 57% yield from intermediate 73 following the procedure described for the step 9 in scheme 1 corresponding to the synthesis of example 1. MS: m/z=941.2 (MH+).

Step 8: N-{3-[(2S)-3-hydroxy-2-{(3-methylbutyl)[(4-nitrophenyl)sulfonyl]amino}propyl]phenyl}-Nα-(methoxycarbonyl)-β-phenyl-L-phenylalaninamide (75)

The title compound was prepared in 62% yield from intermediate 74 following the procedure described for the step 10 in scheme 1 corresponding to the synthesis of example 1. MS: m/z=703.3 (MH+).

Step 9: N-{3-[(2S)-2-{[(4-aminophenyl)sulfonyl](3-methylbutyl)amino}-3-hydroxypropyl]phenyl}-Nα-(methoxycarbonyl)-β-phenyl-L-phenylalaninamide (76)

The title compound was prepared in 61% yield from intermediate 75 following the procedure described for the step 11 in scheme 1 corresponding to the synthesis of example 1. MS: m/z=673.3 (MH+).

H-NMR (400 MHz, DMSO-d6) δ: 9.99 (1 H, s), 7.67 (1 H, d, J=8.92 Hz), 7.39 (6 H, m), 7.29 (2 H, t, J=7.5 Hz), 7.25-7.14 (5 H, m), 7.11-7.01 (2 H, m), 6.76 (1 H, d, J=7.55 Hz), 6.56 (2 H, d, J=8.38 Hz), 5.89 (2 H, s), 5.14 (1 H, t, J=10,25 Hz), 4.67 (1 H, s), 4.37 (1 H, d, J=11.59 Hz), 3.79 (1 H, s), 3.44 (3 H, s), 3.30-3.25 (2 H, m), 3.20-2.96 (2 H, m), 2.78-2.66 (1 H, m), 2.50-2.46 (1 H, m), 1.53-1.38 (3 H, m), 0.84 (6 H, d, J=6.24 Hz).

TABLE 5

Examples made following synthetic procedures analogous to those described for example 31

| Example number | Compound number | Structure | Characterization data MS : m/z |
|---|---|---|---|
| 32 | 77 | N-(3-{(2S)-3-hydroxy-2-[{[4-(hydroxymethyl)phenyl]sulfonyl}(3-methylbutyl)amino]propyl}phenyl)-Nα-(methoxycarbonyl)-β-phenyl-L-phenylalaninamide | 688.2 (MH+) |

TABLE 5-continued

Examples made following synthetic procedures analogous to those described for example 31

| Example number | Compound number | Structure | Characterization data MS : m/z |
|---|---|---|---|
| 33 | 78 | 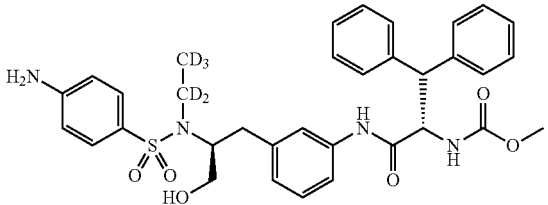<br>N-{3-[(2S)-2-{[(4-aminophenyl)sulfonyl](ethyl-d5)amino}-3-hydroxypropyl]phenyl}-Nα-(methoxycarbonyl)-β-phenyl-L-phenylalaninamide | 636.2 (MH+) |
| 34 | 79 | 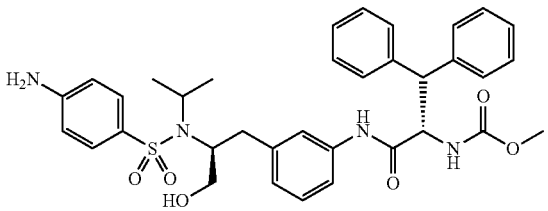 [SMILES: COC(=O)N[C@H](C(=O)Nc1cccc(C[C@@H](CO)N(C(C)C)S(=O)(=O)c2ccc(N)cc2)c1)C(c1ccccc1)c1ccccc1]<br>N-{3-[(2S)-2-{[(4-aminophenyl)sulfonyl](propan-2-yl)amino}-3-hydroxypropyl]phenyl}-Nα-(methoxycarbonyl)-β-phenyl-L-phenylalaninamide | 645.3 (MH+) |
| 35 | 80 | 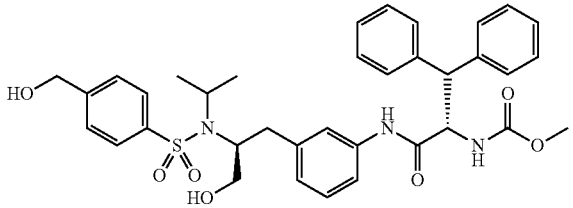 [SMILES: COC(=O)N[C@H](C(=O)Nc1cccc(C[C@@H](CO)N(C(C)C)S(=O)(=O)c2ccc(CO)cc2)c1)C(c1ccccc1)c1ccccc1]<br>N-(3-{(2S)-3-hydroxy-2[{[4-(hydroxymethyl)phenyl]sulfonyl}(propan-2-yl)amino]propyl}phenyl)-Nα-(methoxycarbonyl)-β-phenyl-L-phenylalaninamide | 660.3 (MH+) |

Assay for Inhibition of Microbial Expressed HIV Protease

Inhibition studies of the reaction of the protease (which was expressed in *Eschericia coli*) with a peptide substrate [Val-Ser-Gln-Asn-(betanaphtyl)Ala-Pro-Ile-Val]. The inhibitor is first preincubated with the HIV-1 protease (wild type) enzyme in assay buffer (50 mM sodium acetate, pH 5.5, 100 mM NaCl, and 0.1% BSA) for 30 minutes at room temperature. Substrate is added to 400 micromolar in a total volume of 80 microliters containing 10 picomolar HIV-1 protease and the reaction is incubated for 1 hour at 30° C. The reaction is quenched with the addition of 120 microliters of 10% phosphoric acid. The product formation is determined after separation of product and substrate on a Zorbax Eclipse XDB-C18 column connected to an Agilent 1100 high performance liquid chromatography system with fluorescence detection (excitation 270 nanometer and emission 330 nanometer). Alternatively, the inhibitor is preincubated with enzyme and substrate as described above, but in a total volume of 20 microliters containing 20 picomolar HIV-1 protease and the reaction is incubated for 1 hour at 30° C. The reaction is quenched with the addition of 30 microliters of 1 micromolar indinavir (indinavir is also used as an internal standard), and the product formation is determined after separation of product and substrate on a Zorbax Eclipse XDB-C18 column connected to an API 4000 mass spectrometer (Applied Biosystems) with multiple reaction monitoring (transitions were 644.5/428.9 and 615.4/422.2 (M1/M3) for product and indinavir respectively). The extent of inhibition of the reaction is determined from the peak area of the products. HPLC of the products, independently synthesized, provided quantitation standards and confirmation of the product composition. Representative compounds of the present invention exhibit inhibition of HIV-1 protease in this assay.

Protease Inhibition Assay ("Pepcleave") data were collected based on the wild-type HIV-1 protease enzyme. The assay monitors the cleavage of a 8-mer peptide (VSQN[β-Nal]PIV) where the tyrosine at P1 position is replaced by β-Naphthyl-alanine. Upon cleavage of the peptide by HIV-1 protease, the product is separated from substrate by HPLC column and detected at Ex.=270 nm/Em=330 nm.

Acute Infection Assay ("Spread") data were generated in 10% FBS, and according to the methods disclosed by J. P. Vacca et al, "L-735,524: An orally bioavailable human immunodeficiency virus type 1 protease inhibitor," Proc. Nati. Acad. Sci. USA, Vol. 91, pp. 4096-4100 (April 1994).

Table 6 displays data regarding Pepcleave and Spread data for each of the example compounds. Both columns of data in the table reflect the mean of at least two independent experiments.

TABLE 6

Data from Assays

| Example | Pepcleave Enzyme inhibition IC$_{50}$ (nM) | Spread IC$_{95}$ (nM) |
|---|---|---|
| 1 | 0.02 | 74 |
| 2 | 1.2 | 919 |
| 3 | 0.2 | 307 |
| 4 | 0.2 | 838 |
| 5 | 0.7 | 1194 |
| 6 | 0.07 | 2342 |
| 7 | 1.6 | N.D. |
| 8 | 1.7 | 1548 |
| 9 | 0.3 | 957 |
| 10 | 0.7 | 1186 |
| 11 | 0.05 | 683 |
| 12 | 0.9 | 1528 |
| 13 | 1.9 | 1183 |
| 14 | 1.2 | 1177 |
| 15 | 1.8 | 2443 |
| 16 | 8.1 | N.D. |
| 17 | 10.0 | N.D. |
| 18 | 2.3 | 755 |
| 19 | 4.2 | 766 |
| 20 | 3.5 | 2198 |
| 21 | 3.7 | N.D. |
| 22 | 1.7 | N.D. |
| 23 | 0.06 | 2500 |
| 24 | 4.2 | 1120 |
| 25 | 4.8 | 1153 |
| 26 | 0.4 | 1256 |
| 27 | 6.9 | 1498 |
| 28 | 0.1 | 194 |
| 29 | 2.9 | 1252 |
| 30 | 2.1 | 1778 |
| 31 | 3.7 | 1258 |
| 32 | 2.4 | 1735 |
| 33 | 50.2 | N.D. |
| 34 | 41.6 | N.D. |
| 35 | 18.9 | N.D. |

Compounds displaying pepcleave enzyme inhibition levels of 20 nM or less are considered active, and are thus preferred compounds, while those displaying levels of 1 nM or less are considered highly active, and are thus more preferred compounds.

Certain compounds of the present invention including certain of the exemplified compounds (e.g., certain compounds encompassed by Formula III) having substitution at the epsilon position (i.e., one or both of R$^5$ and R$^{5A}$ in Compound I are other than H) have exhibited better potency in the foregoing assays and/or a better PK profile in animal models than structurally similar compounds that have no branching in the beta, gamma, delta, and epsilon positions (i.e., R$^3$=R$^4$=R$^5$=R$^{5A}$=H), and are thus preferred compounds.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:
1. A compound of Formula I:

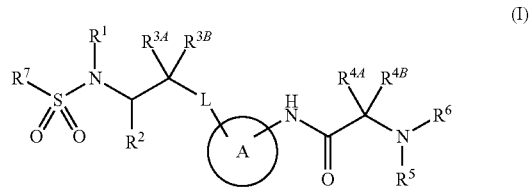

or a pharmaceutically acceptable salt thereof, wherein:
R$^1$ is selected from the group consisting of C$_{1-6}$ alkyl, C$_{1-6}$ fluoroalkyl, CycA, C$_{1-6}$ alkyl substituted with CycA, HetA and C$_{1-6}$ alkyl substituted with HetA;
R$^2$ is selected from the group consisting of C(O)OH, C(O)NH$_2$ and CH(R$^J$)—Z, wherein:
  Z is OH, NH$_2$ or OR$^P$;
  R$^J$ is selected from the group consisting of H, methyl unsubstituted or substituted with F, and C$_1$ fluoroalkyl
  R$^P$ is selected from the group consisting of PO(OH)O—.M$^+$; PO(O—)$_2$.2M$^+$; PO(O—) 2.M$^{2+}$ and C(O)R$^Q$;
  M$^+$ is a pharmaceutically acceptable monovalent counterion;
  M$^{2+}$ is a pharmaceutically acceptable divalent counterion; and
  R$^Q$ is selected from the group consisting of:
    (1) C$_{1-6}$ alkyl,
    (2) C$_{3-6}$ cycloalkyl,
    (3) C$_{1-6}$ alkyl substituted with C$_{3-6}$ cycloalkyl,
    (4) O—C$_{1-6}$ alkyl,
    (5) O—C$_{1-6}$ alkyl substituted with O—C$_{1-6}$ alkyl,
    (6) O—C$_{1-6}$ fluoroalkyl,
    (7) C(O)—C$_{1-6}$ alkylene-N(H)—C$_{1-6}$ alkyl,
    (8) C(O)—C$_{1-6}$ alkylene-N(-C$_{1-6}$ alkyl)$_2$,
    (9) C$_{1-6}$ alkyl substituted with C(O)O-C$_{1-6}$ alkyl,
    (10) C$_{1-6}$ alkyl substituted with C(O)OH,
    (11) C$_{1-6}$ alkyl substituted with C(O)—C$_{1-6}$ alkyl,
    (12) N(H)—C$_{1-6}$ alkyl,
    (13) N(—C$_{1-6}$ alkyl)$_2$,
    (14) C$_{1-6}$ alkyl substituted with NH$_2$, N(H)—C$_{1-6}$ alkyl, or N(—C$_{1-6}$ alkyl)$_2$,
    (15) AryA,
    (16) C$_{1-6}$ alkyl substituted with AryA,
    (17) O—C$_{1-6}$ alkyl substituted with AryA,
    (18) HetA,
    (19) C$_{1-6}$ alkyl substituted with HetA,
    (20) O—C$_{1-6}$ alkyl substituted with HetA,
    (21) HetB and
    (22) O-HetB;
R$^{3A}$ and R$^{3B}$ are each independently selected from the group consisting of H, F and C$_{1-6}$ alkyl;
L is selected from the group consisting of CH(R$^E$), N(R$^E$), O, S, S(O), S(O)$_2$ and a single bond;
RE is selected from the group consisting of H, F and C$_{1-6}$ alkyl;
Ring A is:
  (i) a carbocyclic aromatic ring selected from the group consisting of benzene and naphthalene, wherein, in addition to the two moieties attached to the ring as shown in Formula I, the ring is unsubstituted, or substituted with from 1 to 3 X$^A$ each of which is independently selected from the group consisting of:
    (1) C$_{1-6}$ alkyl,
    (2) C$_{3-6}$ cycloalkyl, (3) $C_{1-6}$ haloalkyl,
(4) OH
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) $SO_2H$,
(25) $SO_2$—$C_{1-6}$ alkyl and
(26) $C_{1-6}$ alkyl substituted with a moiety selected from the group consisting of:
(a) $C_{3-6}$ cycloalkyl,
(b) $C_{1-6}$ haloalkyl,
(c) OH
(d) O—$C_{1-6}$ alkyl,
(e) O—$C_{1-6}$ haloalkyl,
(f) O—$C_{3-6}$ cycloalkyl,
(g) SH,
(h) S—$C_{1-6}$ alkyl,
(i) S—$C_{1-6}$ haloalkyl,
(j) S—$C_{3-6}$ cycloalkyl,
(k) halo,
(l) CN,
(m) $NO_2$,
(n) $NH_2$,
(o) N(H)—$C_{1-6}$ alkyl,
(p) N(—$C_{1-6}$ alkyl)$_2$,
(q) N(H)C(O)—$C_{1-6}$ alkyl,
(r) N(H)CH(O),
(s) CH(O),
(t) C(O)—$C_{1-6}$ alkyl,
(u) C(O)OH,
(v) C(O)O—$C_{1-6}$ alkyl,
(w) $SO_2H$ and
(x) $SO_2$—$C_{1-6}$ alkyl;
or
(ii) a 6-membered heteroaromatic ring containing a total of from 1 to 3 heteroatoms selected from 1 to 3 N, zero or 1 O, and zero or 1 S, wherein, in addition to the two moieties attached to the ring as shown in Formula I, the ring is unsubstituted, or substituted with from 1 to 3 independently selected substituents $X^A$;
$R^{4A}$ is selected from the group consisting of:

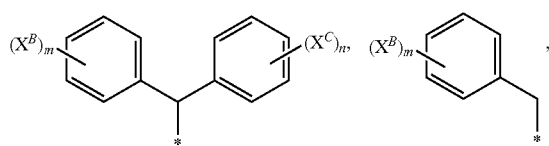

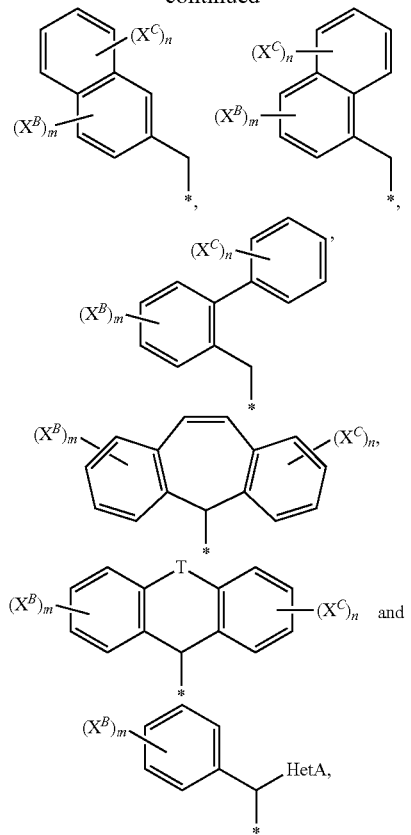

wherein the asterisk (*) denotes the point of attachment to the rest of the compound;
$R^{4B}$ is H or $C_{1-6}$ alkyl;
alternatively, $R^{4A}$ and $R^{4B}$ together with the carbon to which they are attached form a $C_{3-6}$ cycloalkyl which is unsubstituted, or substituted with phenyl, wherein the phenyl is unsubstituted, or substituted with from 1 to 3 $X^B$;
each $X^B$ and each $X^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)–$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,

(24) $SO_2H$,
(25) $SO_2$—$C_{1-6}$ alkyl; and
(26) $C_{1-6}$ alkyl substituted with a moiety selected from the group consisting of:
  (a) $C_{1-6}$ haloalkyl,
  (b) OH
  (c) O—$C_{1-6}$ alkyl,
  (d) O—$C_{1-6}$ haloalkyl,
  (e) O—$C_{3-6}$ cycloalkyl,
  (f) SH,
  (g) S—$C_{1-6}$ alkyl,
  (h) halo,
  (i) CN,
  (j) $NO_2$,
  (k) $NH_2$,
  (l) N(H)—$C_{1-6}$ alkyl,
  (m) N(—$C_{1-6}$ alkyl)$_2$,
  (n) C(O)—$C_{1-6}$ alkyl,
  (o) C(O)OH,
  (p) C(O)O—$C_{1-6}$ alkyl and
  (q) $SO_2$—$C_{1-6}$ alkyl;

T is selected from the group consisting of O, S, S(O) and $SO_2$;

m is an integer equal to 0, 1, 2, or 3;

n is an integer equal to 0, 1, 2, or 3;

$R^5$ is selected from the group consisting of H, $C_{1-6}$ alkyl, $C_{3-6}$ cycloalkyl and $C_{1-6}$ alkyl substituted with $C_{3-6}$ cycloalkyl, or C(O)—$R^K$;

$R^6$ is H or $C_{1-6}$ alkyl;

$R^K$ is selected from the group consisting of:
  (1) H
  (2) $C_{1-6}$ alkyl,
  (3) $C_{3-6}$ cycloalkyl,
  (4) $C_{1-6}$ alkyl substituted with $C_{3-6}$ cycloalkyl,
  (5) O—$C_{1-6}$ alkyl,
  (6) O—$C_{1-6}$ alkyl substituted with O—$C_{1-6}$ alkyl,
  (7) O—$C_{1-6}$ fluoroalkyl,
  (8) $C_{1-6}$ alkyl substituted with C(O)O—$C_{1-6}$ alkyl,
  (9) $C_{1-6}$ alkyl substituted with C(O)OH,
  (10) $C_{1-6}$ alkyl substituted with C(O)—$C_{1-6}$ alkyl,
  (11) N(H)—$C_{1-6}$ alkyl,
  (12) N(—$C_{1-6}$ alkyl)$_2$,
  (13) $C_{1-6}$ alkyl substituted with $NH_2$, N(H)—$C_{1-6}$ alkyl, or N(—$C_{1-6}$ alkyl)$_2$,
  (14) AryA,
  (15) $C_{1-6}$ alkyl substituted with AryA,
  (16) O—$C_{1-6}$ alkyl substituted with AryA,
  (17) HetA,
  (18) $C_{1-6}$ alkyl substituted with HetA,
  (19) O—$C_{1-6}$ alkyl substituted with HetA,
  (20) HetB,
  (21) O-HetB and
  (22) O—$C_{1-6}$ alkyl substituted with HetB;

$R^7$ is AryQ or HetQ;

AryQ is an aryl which is independently phenyl or naphthyl, wherein the phenyl or naphthyl is unsubstituted, or substituted with from 1 to 4 $X^A$ each of which is independently selected from the group consisting of:
  (1) $C_{1-6}$ alkyl,
  (2) $C_{3-6}$ cycloalkyl,
  (3) $C_{1-6}$ haloalkyl,
  (4) OH,
  (5) O—$C_{1-6}$ alkyl,
  (6) O—$C_{1-6}$ haloalkyl,
  (7) O—$C_{3-6}$ cycloalkyl,
  (8) SH,
  (9) S—$C_{1-6}$ alkyl,
  (10) S—$C_{1-6}$ haloalkyl,
  (11) S—$C_{3-6}$ cycloalkyl,
  (12) halo,
  (13) CN,
  (14) $NO_2$,
  (15) $NH_2$,
  (16) N(H)—$C_{1-6}$ alkyl,
  (17) N(—$C_{1-6}$ alkyl)$_2$,
  (18) N(H)C(O)—$C_{1-6}$ alkyl,
  (19) N(H)CH(O),
  (20) CH(O),
  (21) C(O)—$C_{1-6}$ alkyl,
  (22) C(O)OH,
  (23) C(O)O—$C_{1-6}$ alkyl,
  (24) $SO_2H$,
  (25) $SO_2$—$C_{1-6}$ alkyl and
  (26) $C_{1-6}$ alkyl substituted with a moiety selected from the group consisting of:
    (a) $C_{3-6}$ cycloalkyl,
    (b) $C_{1-6}$ haloalkyl,
    (c) OH
    (d) O—$C_{1-6}$ alkyl,
    (e) O—$C_{1-6}$ haloalkyl,
    (f) O—$C_{3-6}$ cycloalkyl,
    (g) SH,
    (h) S—$C_{1-6}$ alkyl,
    (i) S—$C_{1-6}$ haloalkyl,
    (j) S—$C_{3-6}$ cycloalkyl,
    (k) halo,
    (l) CN,
    (m) $NO_2$,
    (n) $NH_2$,
    (o) N(H)—$C_{1-6}$ alkyl,
    (p) N(—$C_{1-6}$ alkyl)$_2$,
    (q) N(H)C(O)—$C_{1-6}$ alkyl,
    (r) N(H)CH(O),
    (s) CH(O),
    (t) C(O)—$C_{1-6}$ alkyl,
    (u) C(O)OH,
    (v) C(O)O—$C_{1-6}$ alkyl,
    (w) $SO_2H$ and
    (x) $SO_2$—$C_{1-6}$ alkyl;

HetQ is a heteroaryl which is independently (i) a 5- or 6-membered heteroaromatic ring containing from 1 to 4 heteroatoms independently selected from N, O and S, wherein each N is optionally in the form of an oxide or (ii) a 9- or 10-membered bicyclic, fused ring system containing from 1 to 4 heteroatoms independently selected from N, O and S, and wherein at least one of the rings is aromatic, each N in a ring is optionally in the form of an oxide, and each S is optionally S(O) or S(O)$_2$; and wherein the heteroaryl is unsubstituted, or substituted with from 1 to 4 independently selected $X^A$;

CycA is a C3_7 cycloalkyl which is unsubstituted, or substituted with from 1 to 4 substituents each of which is independently halo or $C_{1-6}$ alkyl;

each AryA is an aryl which is independently phenyl or naphthyl, wherein the phenyl or naphthyl is unsubstituted, or substituted with from 1 to 4 $Y^B$ wherein each $Y^B$ is independently selected from the group consisting of:
  (1) $C_{1-6}$ alkyl,
  (2) $C_{3-6}$ cycloalkyl,
  (3) $C_{1-6}$ haloalkyl,
  (4) OH,
  (5) O—$C_{1-6}$ alkyl,
  (6) O—$C_{1-6}$ haloalkyl, (7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) $SO_2$H,
(25) $SO_2$—$C_{1-6}$ alkyl; and
(26) $C_{1-6}$ alkyl substituted with a moiety selected from the group consisting of:
  (a) $C_{1-6}$ haloalkyl,
  (b) OH
  (c) O—$C_{1-6}$ alkyl,
  (d) O—$C_{1-6}$ haloalkyl,
  (e) O—$C_{3-6}$ cycloalkyl,
  (f) SH,
  (g) S—$C_{1-6}$ alkyl,
  (h) halo,
  (i) CN,
  (j) $NO_2$,
  (k) $NH_2$,
  (l) N(H)—$C_{1-6}$ alkyl,
  (m) N(—$C_{1-6}$ alkyl)$_2$,
  (n) C(O)—$C_{1-6}$ alkyl,
  (o) C(O)OH,
  (p) C(O)O—$C_{16}$ alkyl and
  (q) $SO_2$—$C_{1-6}$ alkyl;

each HetA is a heteroaryl which is independently (i) a 5- or 6-membered heteroaromatic ring containing from 1 to 4 heteroatoms independently selected from N, O and S, or (ii) is a fused, 9- or 10-membered heterobicyclic ring containing from 1 to 4 heteroatoms independently selected from N, O and S, and wherein at least one of the rings is aromatic, each N in a ring is optionally in the form of an oxide, and each S is optionally S(O) or S(O)$_2$; wherein the heteroaromatic ring (i) or the heterobicyclic ring (ii) is unsubstituted, or substituted with from 1 to 4 $Y^C$ wherein each $Y^C$ is independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) $SO_2$H,
(25) $SO_2$—$C_{1-6}$ alkyl; and
(26) $C_{1-6}$ alkyl substituted with a moiety selected from the group consisting of:
  (a) $C_{1-6}$ haloalkyl,
  (b) OH
  (c) O—$C_{1-6}$ alkyl,
  (d) O—$C_{1-6}$ haloalkyl,
  (e) O—$C_{3-6}$ cycloalkyl,
  (f) SH,
  (g) S—$C_{1-6}$ alkyl,
  (h) halo,
  (i) CN,
  (j) $NO_2$,
  (k) $NH_2$,
  (l) N(H)—$C_{1-6}$ alkyl,
  (m) N(—$C_{1-6}$ alkyl)$_2$,
  (n) C(O)—$C_{1-6}$ alkyl,
  (o) C(O)OH,
  (p) C(O)O—$C_{1-6}$ alkyl and
  (q) $SO_2$—$C_{1-6}$ alkyl;

each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is unsubstituted, or substituted with from 1 to 4 substituents each of which is independently selected from the group consisting of halogen, CN, $C_{1-6}$ alkyl, OH, oxo, O—$C_{1-6}$ alkyl, $C_{1-6}$ haloalkyl, O—$C_{1-6}$ haloalkyl, C(O)$NH_2$, C(O)N(H)—$C_{1-6}$ alkyl, C(O)N(—$C_{1-6}$ alkyl)$_2$, C(O)H, C(O)—$C_{1-6}$ alkyl, $CO_2$H, $CO_2$—$C_{1-6}$ alkyl, $SO_2$H and $SO_2$—$C_{1-6}$ alkyl.

2. A compound according to claim 1, and pharmaceutically acceptable salts thereof, wherein $R^7$ is:
(i) AryQ, wherein AryQ is phenyl which is unsubstituted, or substituted with from 1 to 4 $X^A$; or
(ii) HetQ, wherein HetQ is a 9- or 10-membered bicyclic, fused ring system which is phenyl with a 5- or 6-membered, saturated or unsaturated heterocycle fused thereto, wherein the heterocycle contains from 1 to 2 heteroatoms independently selected from N, O and S, and wherein the fused ring system is unsubstituted, or substituted with from 1 to 4 $X^A$.

3. A compound according to claim 2, and pharmaceutically acceptable salts thereof, wherein
$R^1$ is selected from the group consisting of $C_{1-6}$ alkyl, $C_{1-6}$ fluoroalkyl, CycA, $CH_2$-CycA and $CH_2$-HetA;
$R^2$ is selected form the group consisting of C(O)OH, C(O)$NH_2$, CH($CH_3$)—Z and CH($CF_3$)—Z; wherein Z is OH, $NH_2$, or $OR^P$; and wherein $R^P$ is selected from the group consisting of P(O)(OH)$_2$, P(O)(ONa)$_2$, P(O)(OK)$_2$, C(O)—$C_{1-6}$ alkyl, C(O)O—$C_{1-6}$ alkyl, C(O)N(—$C_{1-6}$ alkyl)$_2$, C(O)-pyridyl and C(O)—$C_{1-6}$ alkylene-$NH_2$;
$R^{3A}$ is H, or $C_{1-4}$ alkyl;
$R^{3B}$ is H;
L is selected from the group consisting of $CH_2$, NH, O, S, S(O), S(O)$_2$ and a single bond;

Ring A is:

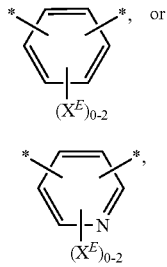

wherein the asterisks (*) denote the points of attachment to the rest of the compound;

each $X^E$ is independently selected from the group consisting of:
(1) $C_{1-3}$ alkyl,
(2) cyclopropyl,
(3) $CF_3$,
(4) OH,
(5) O—$C_{1-3}$ alkyl,
(6) $OCF_3$,
(7) Cl,
(8) Br,
(9) F,
(10) CN,
(11) $NO_2$,
(12) $NH_2$,
(13) N(H)—$C_{1-3}$ alkyl,
(14) N(—$C_{1-3}$ alkyl)$_2$,
(15) C(O)—$C_{1-3}$ alkyl,
(16) $CO_2H$,
(17) C(O)O—$C_{1-3}$ alkyl and
(18) $C_{1-3}$ alkyl substituted with
    (a) cyclopropyl,
    (b) $CF_3$,
    (c) OH,
    (d) O—$C_{1-3}$ alkyl,
    (e) $OCF_3$,
    (f) Cl,
    (g) Br,
    (h) F,
    (i) CN,
    (j) $NO_2$,
    (k) $NH_2$,
    (l) N(H)—$C_{1-3}$ alkyl,
    (m) N(—$C_{1-3}$ alkyl)$_2$,
    (n) C(O)—$C_{1-3}$ alkyl,
    (o) $CO_2H$ or
    (p) C(O)O—$C_{1-3}$ alkyl;

$R^{4A}$ is selected from the group consisting of:

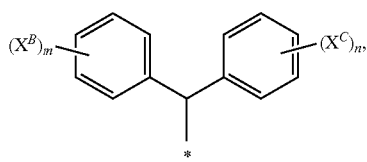

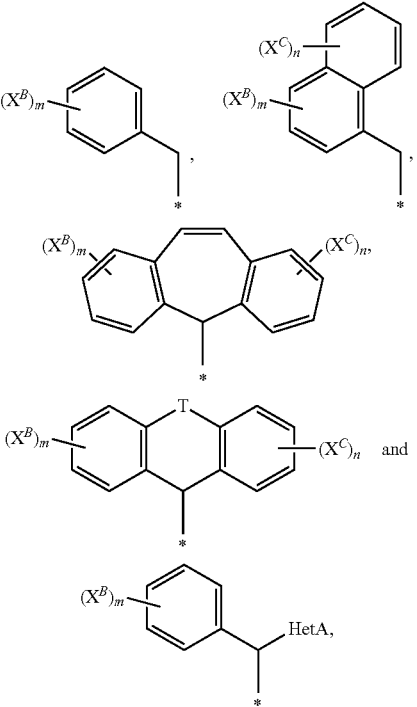

wherein the asterisk (*) denotes the point of attachment to the rest of the compound;

$R^{4B}$ is H or $C_{1-4}$ alkyl;

alternatively, $R^{4A}$ and $R^{4B}$ together with the carbon to which they are attached form a $C_{3-5}$ cycloalkyl which is unsubstituted, or substituted with phenyl, wherein the phenyl is unsubstituted, or substituted with from 1 to 2 $X^B$;

each $X^B$ and each $X^C$ are independently selected from the group consisting of:
(1) $C_{1-3}$ alkyl,
(2) cyclopropyl,
(3) $CF_3$,
(4) OH,
(5) O—$C_{1-3}$ alkyl,
(6) $OCF_3$,
(7) Cl,
(8) Br,
(9) F,
(10) CN,
(11) $NO_2$,
(12) $NH_2$,
(13) N(H)—$C_{1-3}$ alkyl,
(14) N(—$C_{1-3}$ alkyl)$_2$,
(15) C(O)—$C_{1-3}$ alkyl,
(16) $CO_2H$,
(17) C(O)O—$C_{1-3}$ alkyl,
(18) $CH_2OH$ and
(19) $CH_2O$—$C_{1-3}$ alkyl;

wherein m is an integer equal to 0, 1, or 2;
wherein n is an integer equal to 0, 1, or 2;

$R^5$ is selected form the group consisting of H, $C_{1-6}$ alkyl, C(O)—$C_{1-6}$ alkyl, C(O)O—$C_{1-6}$ alkyl, C(O)N(—$C_{1-6}$ alkyl)$_2$, C(O)-HetA, C(O)OCH$_2$-HetA, C(O)-HetB and C(O)OCH$_2$-HetB;

$R^6$ is H or $C_{1-4}$ alkyl;

R[7] is phenyl or benzothiazolyl, either of which is unsubstituted, or substituted with 1 or 2 $X^A$, each of which is independently selected from the group consisting of:
(1) $C_{1-3}$ alkyl,
(2) cyclopropyl,
(3) $CF_3$,
(4) OH,
(5) O—$C_{1-3}$ alkyl,
(6) $OCF_3$,
(7) Cl,
(8) Br,
(9) F,
(10) CN,
(11) $NO_2$,
(12) $NH_2$,
(13) N(H)—$C_{1-3}$ alkyl,
(14) N(—$C_{1-3}$ alkyl)$_2$,
(15) C(O)—$C_{1-3}$ alkyl,
(16) $CO_2H$,
(17) C(O)O—$C_{1-3}$ alkyl and
(18) $C_{1-3}$ alkyl substituted with
  (a) cyclopropyl,
  (b) $CF_3$,
  (c) OH,
  (d) O—$C_{1-3}$ alkyl,
  (e) $OCF_3$,
  (f) Cl,
  (g) Br,
  (h) F,
  (i) CN,
  (j) $NO_2$,
  (k) $NH_2$,
  (l) N(H)—$C_{1-3}$ alkyl,
  (m) N(—$C_{1-3}$ alkyl)$_2$,
  (n) C(O)—$C_{1-3}$ alkyl,
  (o) $CO_2H$ or
  (p) C(O)O—$C_{1-3}$ alkyl;

CycA is a $C_{3-6}$ cycloalkyl which is unsubstituted, or substituted with from 1 to 3 substituents each of which is independently F or $C_{1-4}$ alkyl;

each HetA is independently a heteroaryl selected from the group consisting of pyrrolyl, pyrazolyl, imidazolyl, triazolyl, tetrazolyl, pyridyl, pyrazinyl, quinolyl, isoquinolyl, isoxazolyl and quinoxalinyl, wherein the heteroaryl is unsubstituted, or substituted with from 1 to 3 substituents each of which is independently selected from the group consisting of $CH_3$, $CF_3$, OH, $OCH_3$, $OCF_3$, Cl, Br, F, CN, $NH_2$, N(H)$CH_3$, N($CH_3$)$_2$, l C(O)$CH_3$, $CO_2CH_3$ and $SO_2CH_3$; and HetB is a saturated heterocyclic ring selected from the group consisting of tetrahydrofuranyl, pyrrolidinyl, piperidinyl, piperazinyl, morpholinyl and thiomorpholinyl in which the S is optionally oxidized to S(O) or S(O)$_2$, and wherein the ring is unsubstituted, or substituted with 1 or 2 substituents each of which is independently selected from the group consisting of $CH_3$, $CH_2CH_3$, oxo, C(O)N($CH_3$)$_2$, C(O)$CH_3$, $CO_2CH_3$, and S(O)$_2CH_3$.

4. The compound according to claim 3, and pharmaceutically acceptable salts thereof, wherein:

R[1] is selected from the group consisting of $CH_3$, $CH_2CH_3$, CH($CH_3$)$_2$, $CH_2CH_2CH_3$, $CH_2CH_2CH_2CH_3$, $CH_2CH(CH_3)_2$, $CH_2CH_2CH(CH_3)_2$, $CH_2CH_2CH_2F$, CycA, $CH_2$-CycA and $CH_2$-HetA;

R[2] is selected from the group consisting of $CH_2OH$, CH($CH_3$)OH, $CH_2NH_2$, CH($CH_3$)$NH_2$, $CH_2OR^P$ and CH($CH_3$)—$OR^P$, wherein $R^P$ is selected from the group consisting of P(O)(OH)$_2$, P(O)(ONa)$_2$ and C(O)$CH_3$;

$R^{3A}$ is H;

L is selected from the group consisting of $CH_2$, NH, O, S and a single bond;

Ring A is selected from the group consisting of:

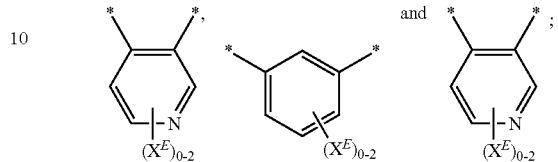

each $X^E$ is independently selected from the group consisting of:
(1) $CH_3$,
(2) $CH_2CH_3$,
(3) $CF_3$,
(4) OH,
(5) $OCH_3$,
(6) $OCF_3$,
(7) Cl,
(8) Br,
(9) F and
(10) CN;

$R^{4A}$ is selected from the group consisting of:

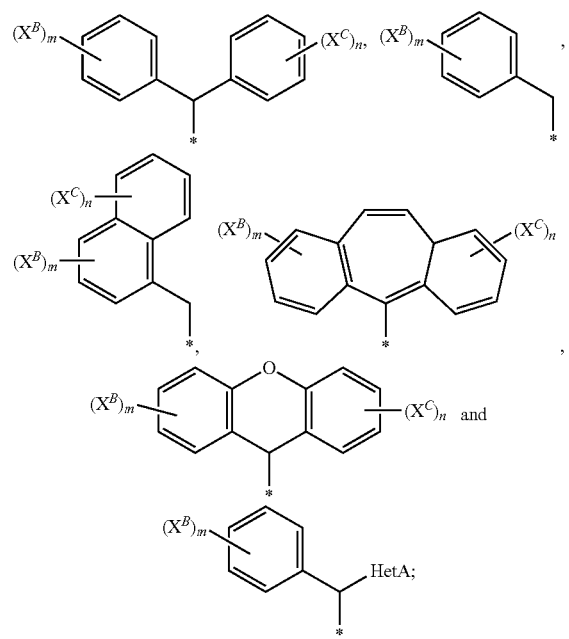

$R^{4B}$ is H;

each $X^B$ and each $X^C$ are independently selected from the group consisting of:
(1) $CH_3$,
(2) $CH_2CH_3$,
(3) $CF_3$,
(4) OH,
(5) $OCH_3$,
(6) $OCF_3$,
(7) Cl,
(8) Br, (9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH, and
(17) CH$_2$OCH$_3$;

R$^5$ is selected from the group consisting of H, CH$_3$, C(O)CH$_3$, C(O)OCH$_3$, C(O)OC(CH$_3$)$_3$, C(O)N(CH$_3$)$_2$, C(O)-morpholinyl, C(O)-pyridyl and C(O)O—CH$_2$-pyridyl;

R$^6$ is H or CH$_3$;

R$^7$ is phenyl or benzothiazolyl, wherein the benzothiazolyl is unsubstituted and the phenyl is unsubstituted, or substituted with 1 or 2 X$^A$, each of which is independently selected from the group consisting of:
(1) CH$_3$,
(2) CH$_2$CH$_3$,
(3) CF$_3$,
(4) OH,
(5) OCH$_3$,
(6) OCF$_3$,
(7) Cl,
(8) Br,
(9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH,
(17) CH$_2$OCH$_3$,
(18) CH$_2$NH$_2$,
(19) CH$_2$N(H)CH$_3$,
(20) CH$_2$N(CH$_3$)$_2$,
(21) CH(CH$_3$)OH,
(22) CH(CH$_3$)OCH$_3$,
(23) CH(CH$_3$)NH$_2$,
(24) CH(CH$_3$)N(H)CH$_3$ and
(25) CH(CH$_3$)N(CH$_3$)$_2$;

CycA is cyclopropyl or cyclobutyl, wherein the cyclopropyl or cyclobutyl is unsubstituted, or substituted with 1 or 2 F; and, HetA is a heteroaryl selected from the group consisting of pyrrolyl, pyrazolyl, imidazolyl, isoxazolyl and pyridyl, wherein the heteroaryl is unsubstituted, or substituted with from 1 or 2 substituents each of which is independently selected from the group consisting of CH$_3$, CF$_3$, OH, OCH$_3$, OCF$_3$, Cl, Br, F and CN.

5. The compound according to claim 4, and pharmaceutically acceptable salts thereof, wherein:

R$^1$ is selected from the group consisting of CH$_3$, CH$_2$CH$_3$, CH(CH$_3$)$_2$, CH$_2$CH$_2$CH$_3$, CH$_2$CH$_2$CH$_2$CH$_3$, CH$_2$CH(CH$_3$)$_2$, CH$_2$CH$_2$CH(CH$_3$)$_2$, CH$_2$CH$_2$CH$_2$F, cyclobutyl, CH$_2$-cyclopropyl, CH$_2$-cyclobutyl in which the cyclobutyl is substituted with 1 or 2 F, CH2-pyrazolyl in which the pyrazolyl is substituted with 0-2 CH$_3$; and CH$_2$-isoxazolyl;

R$^2$ is selected from the group consisting of CH$_2$OH, CH(CH$_3$)OH, and CH$_2$NH$_2$;

L is selected from the group consisting of CH$_2$, S and a single bond;

Ring A is selected from the group consisting of:

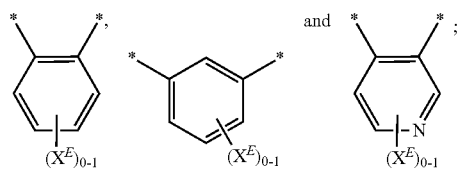

X$^E$ is selected from the group consisting of:
(1) CH$_3$,
(2) CF$_3$,
(4) OH,
(5) OCH$_3$,
(6) OCF$_3$, and
(7) F;

R$^{4A}$ is selected from the group consisting of:

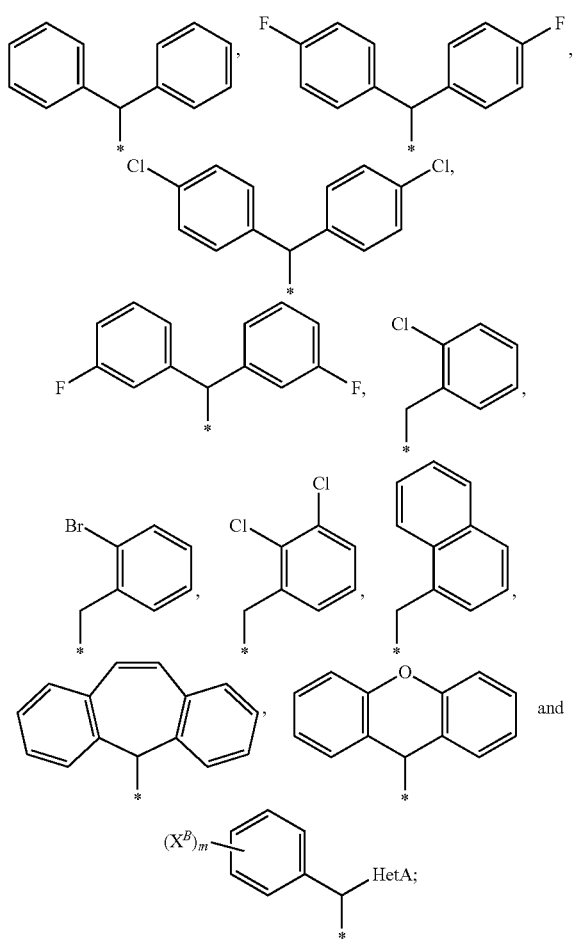

R$^5$ is selected from the group consisting of H, CH$_3$, C(O)OCH$_3$, C(O)OC(CH$_3$)$_3$ and C(O)O—CH$_2$-pyridyl; and R$^6$ is H or CH$_3$; and R$^7$ is:
(i) phenyl substituted with 1 or 2 X$^A$, wherein one X$^A$ is in the para position on the phenyl ring and is CH$_3$, Cl, Br, F, NH$_2$, C(O)CH$_3$, CH$_2$OH, or CH(CH$_3$)OH; and the other, optional X$^A$ is in the meta position on the phenyl ring and is Cl, Br, or F; or

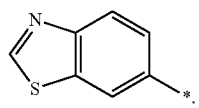

(ii)

6. The compound according to claims 1, and pharmaceutically acceptable salts thereof, wherein:
$R^2$ is $CH_2OH$;
$R^5$ is $C(O)OCH_3$ and
$R^6$ is H.

7. The compound according to claim 1, which is a compound of Formula II:

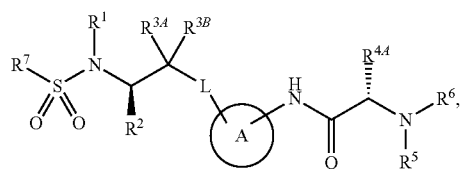

(II)

or a pharmaceutically acceptable salt thereof.

8. The compound according to claim 1, which is a compound of Formula III:

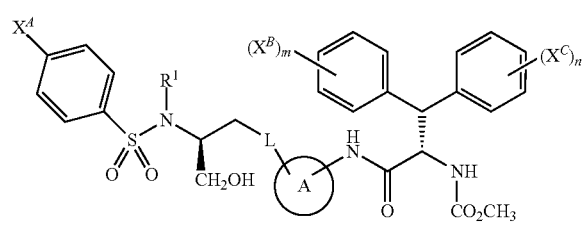

(III)

and pharmaceutically acceptable salts thereof, wherein:
$R^1$ is selected from the group consisting of $CH_3$, $CH_2CH_3$, $CH(CH_3)_2$, $CH_2CH_2CH_3$, $CH_2CH_2CH_2CH_3$, $CH_2CH(CH_3)_2$, $CH_2CH_2CH(CH_3)_2$, $CH_2CH_2CH_2F$, cyclobutyl, $CH_2$-cyclopropyl, $CH_2$-cyclobutyl in which the cyclobutyl is substituted with 1 or 2 F, CH2-pyrazolyl in which the pyrazolyl is substituted with 0-2 $CH_3$ and $CH_2$-isoxazolyl substituted with 1 or 2 $CH_3$;
L is selected from the group consisting of $CH_2$, S and a single bond;
Ring A is selected from the group consisting of:

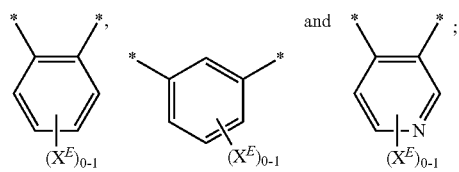

wherein the asterisks (*) denote the points of attachment to the rest of the compound;
$X^E$ is selected from the group consisting of:
(1) $CH_3$;
(2) $CF_3$;
(4) OH;
(5) $OCH_3$;
(6) $OCF_3$; and,
(7) F;
$X^A$ is selected from the group consisting of $NH_2$, $C(O)CH_3$, $CH_2OH$ and $CH(CH_3)OH$;
each $X^B$ and each $X^C$ are independently selected from the group consisting of:
(1) $CH_3$;
(2) $CH_2CH_3$;
(3) $CF_3$;
(4) OH;
(5) $OCH_3$;
(6) $OCF_3$;
(7) Cl;
(8) Br;
(9) F;
(10) CN;
(11) $NH_2$;
(12) $N(H)CH_3$;
(13) $N(CH_3)_2$;
(14) $C(O)CH_3$;
(15) $C(O)OCH_3$;
(16) $CH_2OH$; and,
(17) $CH_2OCH_3$;
wherein m is an integer equal to 0, 1, or 2; and
n is an integer equal to 0, 1, or 2.

9. The compound according to claim 8, and pharmaceutically acceptable salts thereof, wherein
$R^1$ is selected from the group consisting of $CH_2CH(CH_3)_2$ and $CH_2CH_2CH(CH_3)_2$; and
Ring A is selected from the group consisting of:

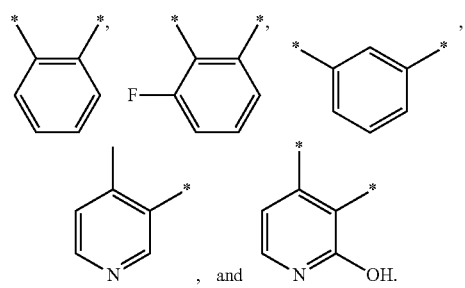

10. The compound according to claim 1, and pharmaceutically acceptable salts thereof, wherein m and n are either both 0 or both 1; and $X^B$ and $X^C$ are (i) both F and both para substituents, (ii) both F and both meta substituents, or (iii) both Cl and both para substituents.

11. The compound according to claim 1, wherein
$R^1$ is selected from the group consisting of propyl-d9; isopropyl; isobutyl; isobutyl-d9; cyclopropylmethyl; isoamyl; (3,3-difluorocyclobutyl)methyl; (1,3-dimethyl-1H-pyrazol-4-yl)methyl; (1H-pyrazol-4-yl)methyl; (isoxazol-4-yl)methyl and (4-methylpyrimidin-5-yl)methyl;
$R^2$ is $CH_2OH$;
$R^{3A}$ and $R^{3B}$ are independently selected from the group consisting of H and D;
L is selected from the group consisting of —$CH_2$—; —$CD_2$-; —S—; —S(O)—; and —$S(O)_2$—;

101

A is selected from the group consisting of

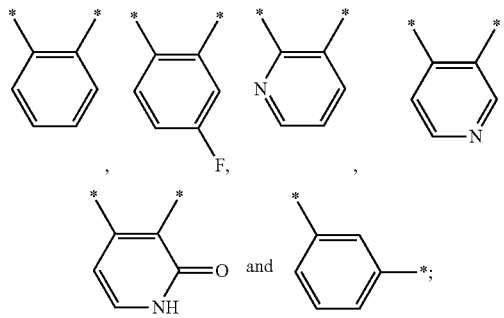

and $R^{4A}$ is selected from the group consisting of

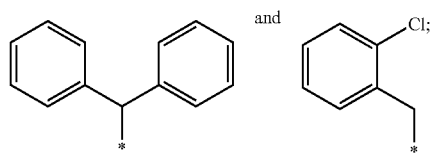 [SMILES: "and" ; *C(c1ccccc1)c1ccccc1 ; *Cc1ccccc1Cl]

$R^{4B}$ is H;
$R^5$ is —C(O)OCH$_3$,
$R^6$ is H; and,
$R^7$ is selected from the group consisting of

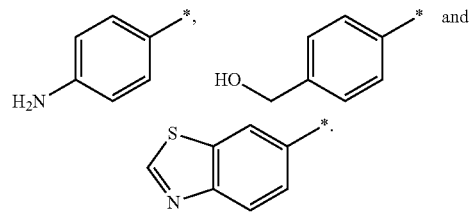

12. The compound according to claim 1, wherein $R^1$ is selected from the group consisting of isobutyl, isoamyl, (3,3-difluorocyclobutyl)methyl, (1,3-dimethyl-1H-pyrazol-4-yl)methyl, (1H-pyrazol-4-yl)methyl and (isoxazol-4-yl)methyl;
$R^2$ is CH$_2$OH;
$R^{3A}$ and $R^{3B}$ are H;
L is —CH$_2$—;
A is

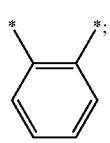

$R^{4B}$ is H;
$R^5$ is —C(O)OCH$_3$;
$R^6$ is H; and,

102

$R^7$ is

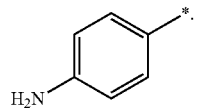

13. A compound according to claim 1 selected from the group consisting of:

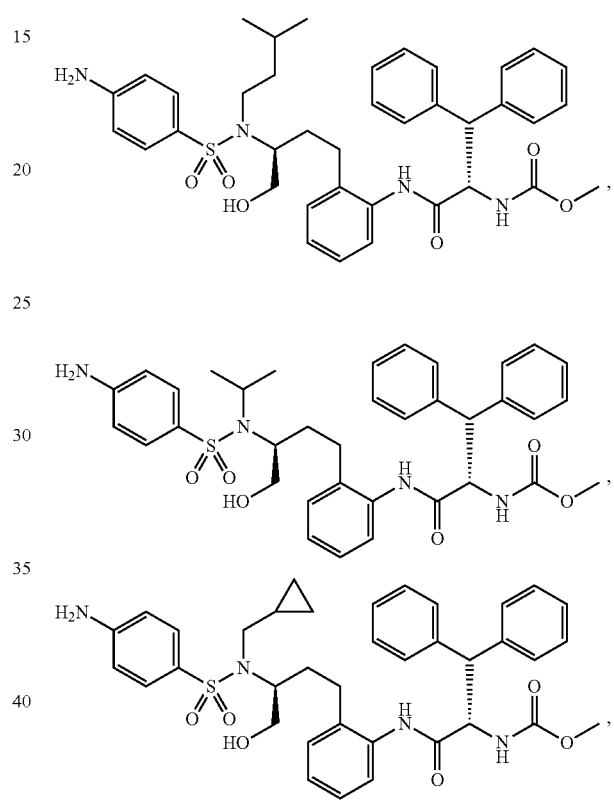

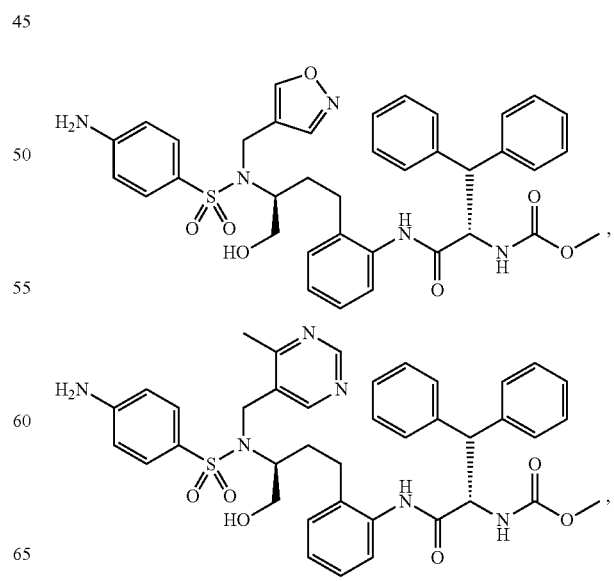

103
-continued
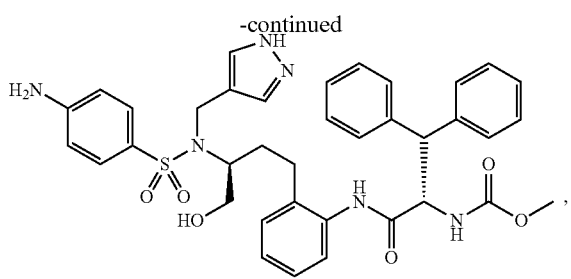
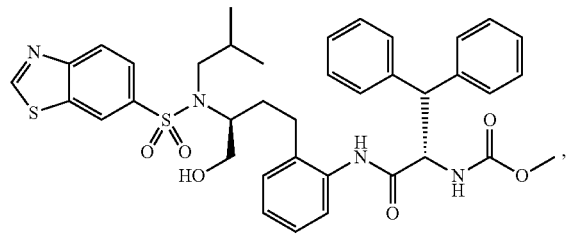
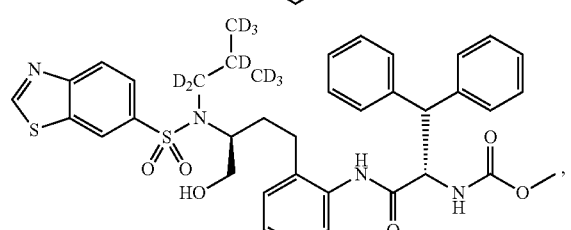
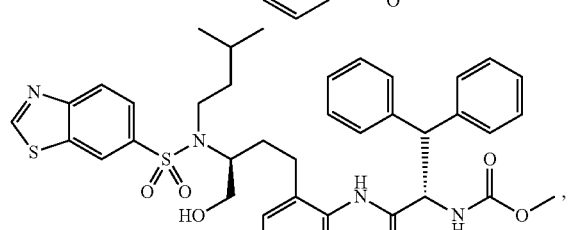
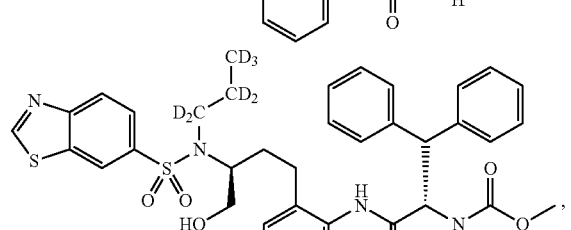
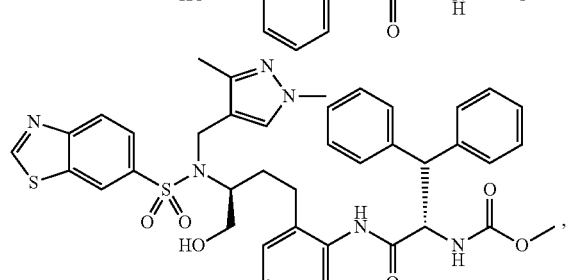
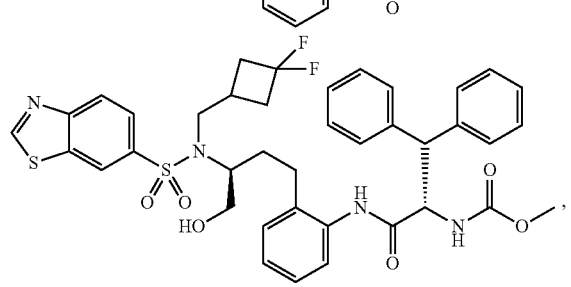
104
-continued
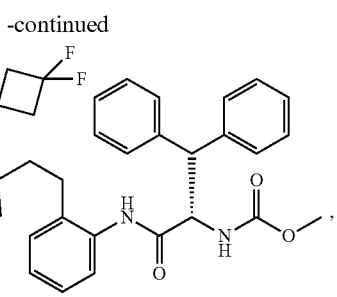
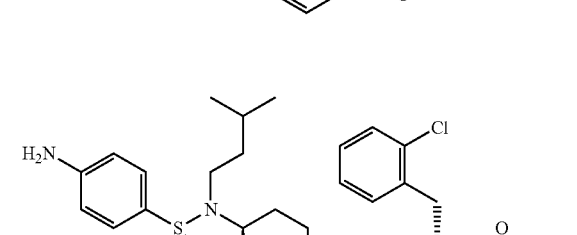
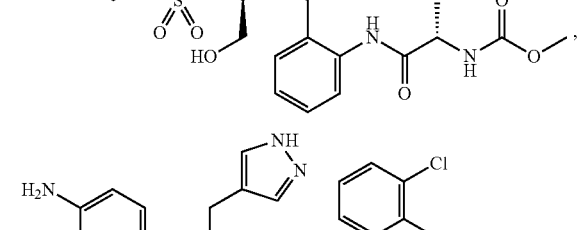
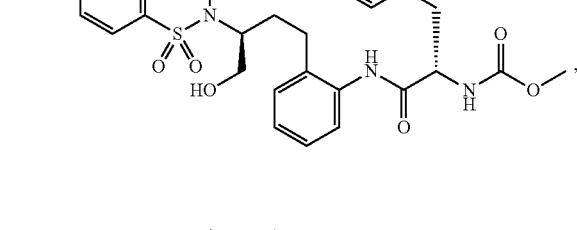
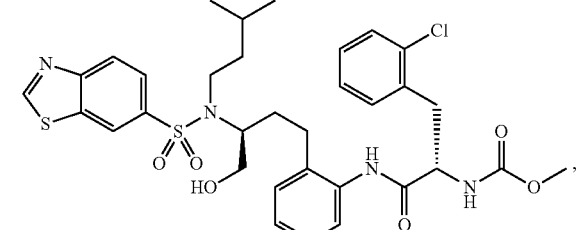
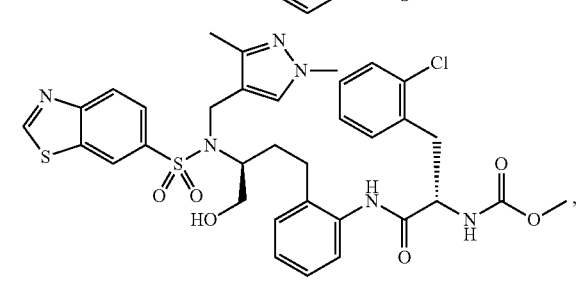
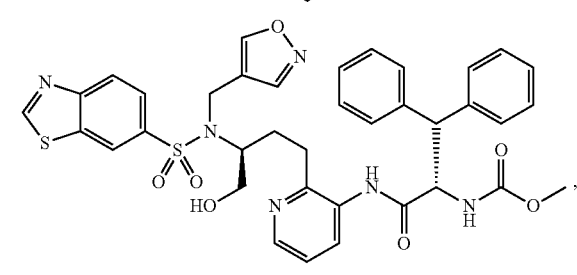

105
-continued
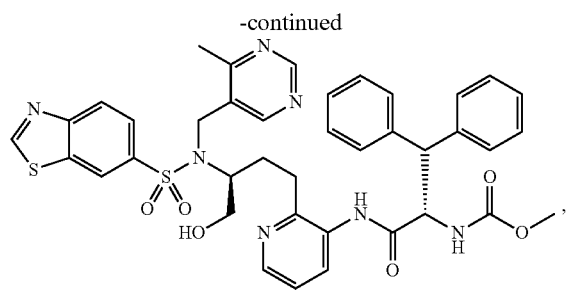
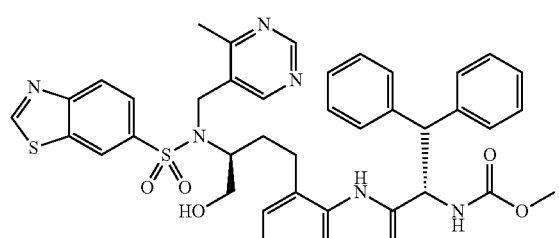
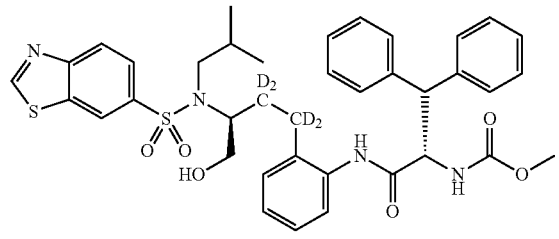
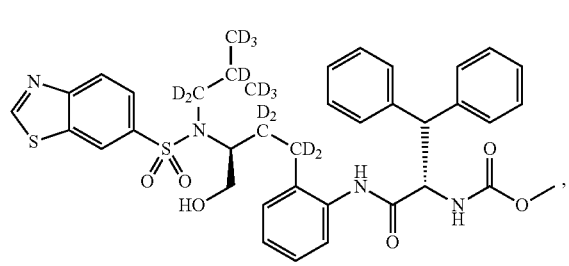
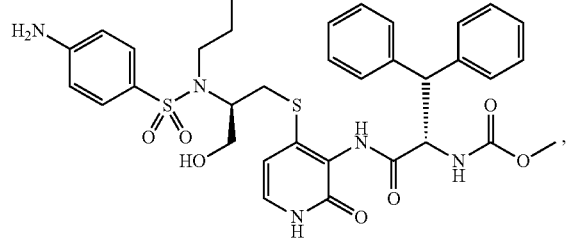
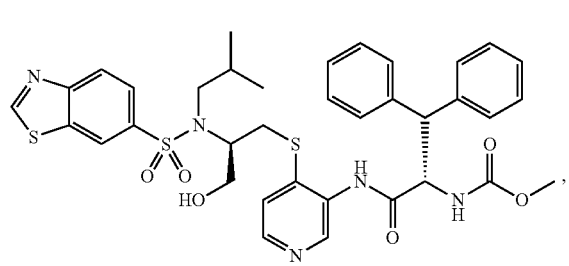
106
-continued
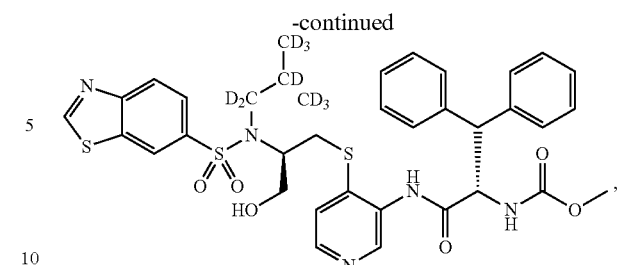
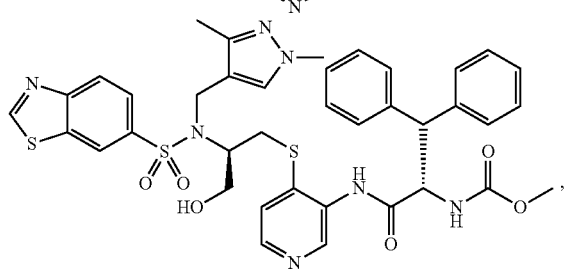
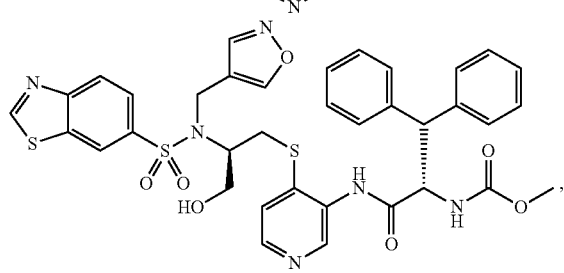
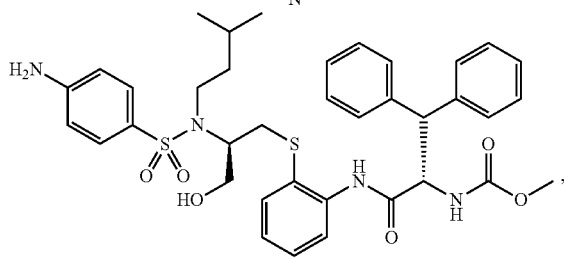
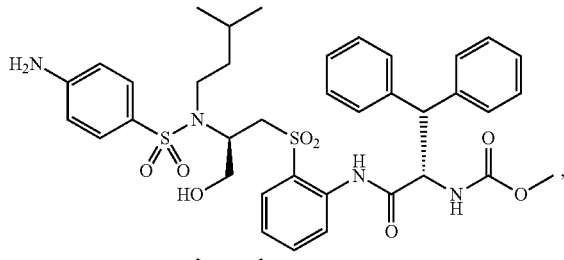
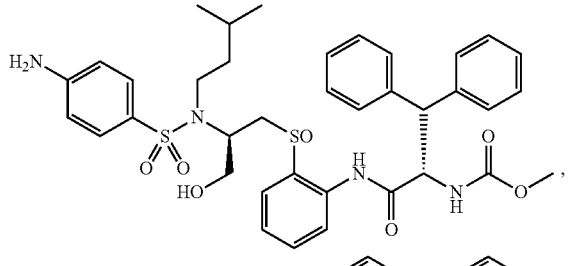
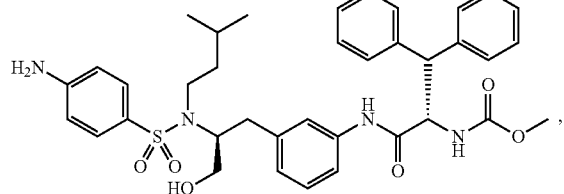

-continued

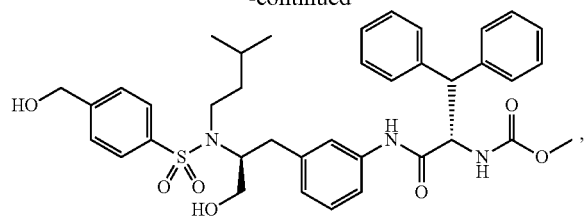

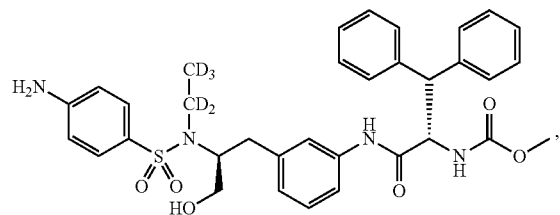

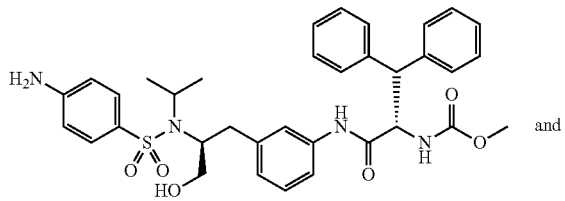

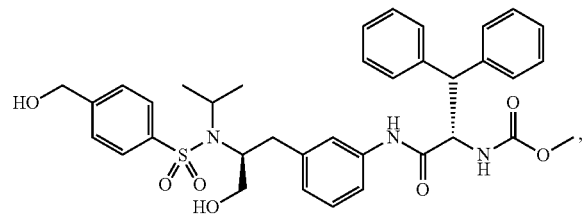

and pharmaceutically acceptable salts thereof.

14. A compound according to claim 1, selected from the group consisting of:

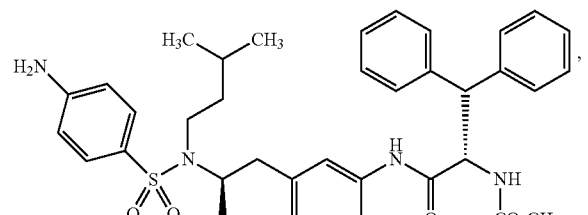

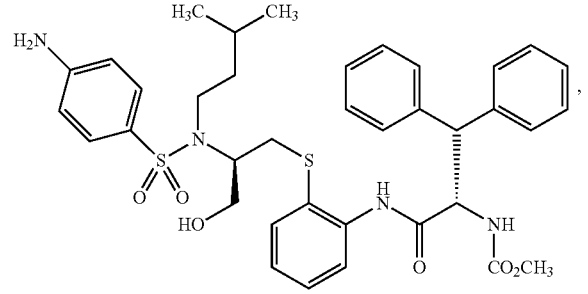

-continued

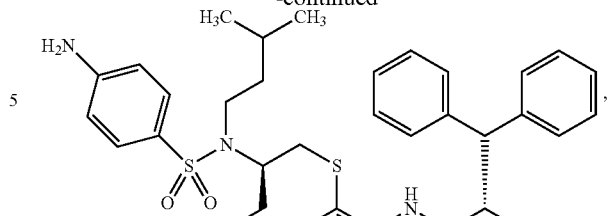

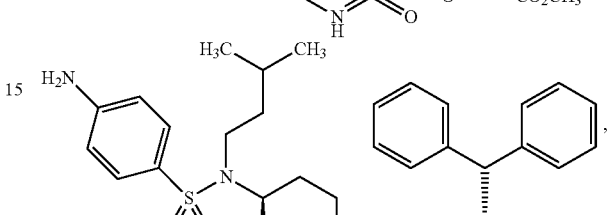

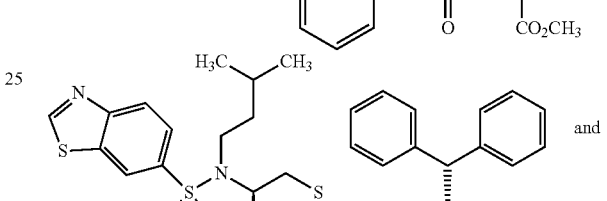

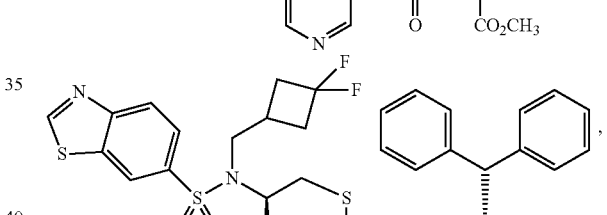

and pharmaceutically acceptable salts thereof.

15. A pharmaceutical composition comprising an effective amount of a compound according to claim 1 or a pharmaceutically acceptable salt thereof, and a pharmaceutically acceptable carrier.

16. A method for the treatment or prophylaxis of infection by HIV or for the treatment, prophylaxis, or delay in the onset of AIDS in a subject in need thereof, which comprises administering to the subject an effective amount of a compound according to claim 1 or a pharmaceutically acceptable salt thereof.

17. A pharmaceutical composition comprising an effective amount of a compound according to claim 1 or a pharmaceutically acceptable salt thereof, and one or more HIV antivirals selected from those listed in Table A:

TABLE A

| Name | Type |
|---|---|
| abacavir, ABC, Ziagen ® | nRTI |
| abacavir + lamivudine, Epzicom ® | nRTI |

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI. |

18. A method for the inhibition of HIV protease, which comprises administering to the subject an effective amount of the compound according to claim 1 or a pharmaceutically acceptable salt thereof.

19. The method according to claim 18 further comprising administering to the subject an effective amount of one or more HIV antivirals selected from those listed in Table A:

20. A method for the treatment or prophylaxis of infection by HIV or for the treatment, prophylaxis, or delay in the onset of AIDS in a subject in need thereof, which comprises administering to the subject an effective amount of the pharmaceutical composition according to claim 17.

* * * * *